(12) United States Patent
Froestl et al.

(10) Patent No.: US 8,673,940 B2
(45) Date of Patent: Mar. 18, 2014

(54) COMPOUNDS FOR THE TREATMENT OF DISEASES ASSOCIATED WITH AMYLOID OR AMYLOID-LIKE PROTEINS

(75) Inventors: Wolfgang Froestl, Ecublens (CH); Nampally Sreenivasachary, Ecublens (CH); Sophie Lohmann, Ecublens (CH); Maria Pilar Lopez Deber, Ecublens (CH); Andreas Muhs, Pully (CH); Maria Pihlgren Bosch, St. Sulpice (CH)

(73) Assignee: AC Immune SA, Lausanne (CH)

( * ) Notice: Subject to any disclaimer, the term of this patent is extended or adjusted under 35 U.S.C. 154(b) by 0 days.

(21) Appl. No.: 13/557,770

(22) Filed: Jul. 25, 2012

(65) Prior Publication Data
US 2012/0309791 A1 Dec. 6, 2012

Related U.S. Application Data

(63) Continuation of application No. 12/516,151, filed as application No. PCT/EP2007/010219 on Nov. 23, 2007, now abandoned.

(30) Foreign Application Priority Data

Nov. 24, 2006 (EP) .................................... 06024427

(51) Int. Cl.
*A61K 31/44* (2006.01)
(52) U.S. Cl.
USPC ........ 514/332; 514/277; 546/276.4; 546/255; 546/264

(58) Field of Classification Search
None
See application file for complete search history.

(56) References Cited

U.S. PATENT DOCUMENTS

| 3,212,892 | A | 10/1965 | von Konig et al. |
| 3,651,023 | A | 3/1972 | Ottenheym et al. |
| 4,545,809 | A | 10/1985 | Seki et al. |
| 7,105,503 | B2 | 9/2006 | Zhang |

FOREIGN PATENT DOCUMENTS

| EP | 0129830 A2 | 1/1985 |
| RU | 99117921 | 6/2004 |
| SU | 181121 | 4/1966 |
| SU | 400583 A1 | 10/1973 |
| WO | WO 96/14843 | 5/1996 |
| WO | WO 03/013523 A1 | 2/2003 |
| WO | WO 03/045949 A1 | 6/2003 |
| WO | WO 03/080616 | 10/2003 |
| WO | WO 03/095429 A1 | 11/2003 |
| WO | WO 2004/029050 A1 | 4/2004 |
| WO | WO 2004/058258 | 7/2004 |
| WO | WO 2004/110350 | 12/2004 |
| WO | WO 2005/000798 A1 | 1/2005 |
| WO | WO 2005/082856 A2 | 9/2005 |
| WO | WO 2006/039327 A2 | 4/2006 |
| WO | WO 2006/065204 A1 | 6/2006 |
| WO | WO 2007/068411 | 6/2007 |
| WO | WO 2007/098967 | 9/2007 |
| WO | WO 2008/011348 A2 | 1/2008 |
| WO | WO 2008/061795 A2 | 5/2008 |

OTHER PUBLICATIONS

English-language translation of Office Action dated Nov. 23, 2011 for Russian Patent Application No. 2009123647.
English-language translation of Office Action dated Feb. 28, 2011 for Chinese Patent Application No. 2007800496221.
Citron, "Alzheimer's Disease: Strategies for Disease Modification," Nature Rev. Drug Discov., vol. 9, 2010, pp. 387-398.
Citron, "Alzheimer's Disease: Treatments in Discovery and Development," Nature Neurosci. (Suppl.) 5, 2002, pp. 1055-1057.
Dorgan et al., "N-Alkyl and N-Acyl Derivatives of 3(5)-Aminopyrazole," Journal of Chemical Research, vol. 6, 1979, p. 198.
Gever, "Beta-Amyloid Inhibitor Fails in Alzheimer's Trial," retrieved from www.MedPageToday.com, Dec. 15, 2009.
Graubaum, "Acylwanderungen am 3(5)-Amino-Pyrazol," J. Prakt. Chem, vol. 335, 1993, pp. 585-588.
Grohol, "Alzheimer's Drug Fails Clinical Trials," retrieved from psychocentral.com, Aug. 18, 2010.
Hergenrother, "Poly-1,2,4-Triazoles and Poly-1,3,4-Oxadiazoles from Precursor Poly-N-Acylhydrazines," Macromolecules, vol. 3, No. 1, Jan.-Feb. 1970, pp. 10-15.
Hill, "Flurizan Hopes Flattened by Failure in Latest Clinical Trial," retrieved from About.com, Jun. 30, 2008.
Moustafa, "Synthesis and Some Reactions of Quinoxalinecarboazides," J. Chin. Chem. Soc., vol. 47, No. 2, 2000, pp. 351-357.
Pahnke, "Alzheimer's Disease and Blood-Brain Barrier Function: Why Have Anti-β-Amyloid Therapies Failed to Prevent Dementia Progression?" Neurosci. Biobehav. Rev., vol. 33, 2009, pp. 1099-1108.
Pajouhesh, J. Am. Soc. Exp. Neurother., 2005, vol. 2, p. 541.
Pfeiffer et al., "Effect of Butyllithium on 6H-1,3,4-Thiadiazines," vol. 22, No. 4, 1982, pp. 137-138.
Pfeiffer et al., "The Ring Contraction of 6H-1,3,4-Thiadiazines to Pyrazoles under the Effects of Triphenylphosphine and Triethylphosphite," vol. 7, Feb. 17, 1977, pp. 485-487.
Rzepecki et al., "Prevention of Alzheimer's Disease-associated AB Aggregation by Rationally Designed Nonpeptidic B-Sheet Ligands", The Journal of Biological Chemistry, vol. 279, No. 46, Issue of Nov. 12, pp. 47497-47505 2004.

(Continued)

*Primary Examiner* — Brandon Fetterolf
*Assistant Examiner* — Theodore R West
(74) *Attorney, Agent, or Firm* — Ian J. Griswold; Johnson, Marcou & Isaacs, LLC

(57) ABSTRACT

The present invention relates to novel compounds of formula (II) that can be employed in the treatment of a group of disorders and abnormalities associated with amyloid protein, such as Alzheimer's disease, and of diseases or conditions associated with amyloid-like proteins. The compounds of the present invention can also be used in the treatment of ocular diseases associated with pathological abnormalities/changes in the tissues of the visual system. The present invention further relates to pharmaceutical compositions comprising these compounds and to the use of these compounds for the preparation of medicaments for treating, or preventing diseases or conditions associated with amyloid and/or amyloid-like proteins. A method of treating or preventing diseases or conditions associated with amyloid and/or amyloid-like proteins is also disclosed.

7 Claims, No Drawings

(56) References Cited

OTHER PUBLICATIONS

Stoicescu-Crivat et al., "Poly-1,3,4-Oxadiazoles III, Polycondensation of 5-Aminotetrazole with Diacid Chlorides," Inst. Macromol. Chem. May 25, 2009.
Uversky, "Mysterious Oligomerization of the Amyloidogenic Proteins," Febs J., vol. 277, 2010, pp. 2940-2953.
Database Beilstein Beilstein Institute for Organic Chemistry, Frankfurt-Main, DE; 1988, Database accession No. BRN: 4961227.
Database Beilstein Beilstein Institute for Organic Chemistry, Frankfurt-Main, DE; 1985, Database accession No. BRN: 5954121.
Database Beilstein Beilstein Institute for Organic Chemistry, Frankfurt-Main, DE; 1982, Database accession No. BRN: 5739402.
Database Beilstein Beilstein Institute for Organic Chemistry, Frankfurt-Main, DE; 1979, Database accession No. BRN: 779646.
Database Beilstein Beilstein Institute for Organic Chemistry, Frankfurt-Main, DE; 1979, Database accession No. BRN: 1099195.
Database Beilstein Beilstein Institute for Organic Chemistry, Frankfurt-Main, DE; 1970, Database accession No. BRN: 744195.
Office Action dated Oct. 26, 2011 for U.S. Appl. No. 12/516,151, pp. 1-18.
Office Action dated Jun. 22, 2011 for U.S. Appl. No. 12/516,151, pp. 1-18.
Office Action dated Oct. 25, 2012 for U.S. Appl. No. 12/905,356, pp. 1-17.
Final Office Action dated May 2, 2013 for U.S. Appl. No. 12/905,356, pp. 1-12.
English-language translation of Office Action dated Feb. 4, 2013 for Japanese Patent Application No. 2009-537556, pp. 1-11.
International Search Report and Written Opinion for PCT/EP2010/065439 dated Apr. 26, 2011, pp. 1-14.
European Extended Search Report for European Patent Application No. 09173184.4 dated Apr. 14, 2010, pp. 1-6.
Dorwald et al., "Side Reactions in Organic Synthesis: A Guide to Successful Synthesis Design," 2005, Wiley, VCH Weinheim Preface, pp. 1-15 & Chapter 8, pp. 279-308.
Huc et al., "Hydroxy-Substituted Oligopyridine Dicarboxamide Helical Foldamers," Chem. Cornmun., 2002, No. 6, pp. 578-579.
Rzepecki et al., "Aminopyrazole Oligomers for a-SheetStabilization of Peptides," Synthesis, Sep. 2, 2003, No. 12, pp. 1815-1826.
Huc et al., "Hydroxy-Substituted Oligopyridine Dicarboxamide Helical Foldamers," Chem. Commun., 2002, No. 6, pp. 578-579.

COMPOUNDS FOR THE TREATMENT OF DISEASES ASSOCIATED WITH AMYLOID OR AMYLOID-LIKE PROTEINS

RELATED PRIORITY APPLICATIONS

This application is a continuation of U.S. patent application Ser. No. 12/516,151, filed May 22, 2009, which is the U.S. National Stage patent application filed under 35 U.S.C. §371 of International Patent Application No. PCT/EP2007/010219, filed Nov. 23, 2007, which designated the United States of America, and which claims the benefit of European Patent Application No. 06024427.4, filed Nov. 24, 2006. The disclosure of each of the above-identified related applications is hereby fully incorporated herein by reference.

The present invention relates to novel compounds that can be employed in the treatment of a group of disorders and abnormalities associated with amyloid protein, such as Alzheimer's disease, and of diseases or conditions associated with amyloid-like proteins. The present invention further relates to pharmaceutical compositions comprising these compounds and to the use of these compounds for the preparation of medicaments for the treatment of diseases or conditions associated with amyloid or amyloid-like proteins. A method of treating diseases or conditions associated with amyloid or amyloid-like proteins is also disclosed.

The compounds of the present invention can also be used in the treatment of ocular diseases associated with pathological abnormalities/changes in the tissues of the visual system, particularly associated with amyloid-beta-related pathological abnormalities/changes in the tissues of the visual system, such as neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidoses; the retina leading to primary retinal degeneration and macular degeneration, for example age-related macular degeneration; the optic nerve leading to optic nerve drusen, optic neuropathy and optic neuritis; and the cornea leading to lattice dystrophy.

Many diseases of aging are based on or associated with amyloid or amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidoses; the retina, including primary retinal degenerations and macular degeneration, in particular age-related macular degeneration; the optic nerve, including optic nerve drusen, optic neuropathy and optic neuritis; and the cornea, including lattice dystrophy.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators.

Alzheimer's Disease (AD) is a neurological disorder primarily thought to be caused by amyloid plaques, an accumulation of abnormal deposit of proteins in the brain. The most frequent type of amyloid found in the brain of affected individuals is composed primarily of Aβ fibrils. Scientific evidence demonstrates that an increase in the production and accumulation of beta-amyloid protein in plaques leads to nerve cell death, which contributes to the development and progression of AD. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP), which is constitutively expressed and catabolized in most cells, by the enzymes β and γ secretase leads to the release of a 39 to 43 amino acid Aβ peptide. The degradation of APPs likely increases their propensity to aggregate in plaques. It is especially the Aβ(1-42) fragment that has a high propensity of building aggregates due to two very hydrophobic amino acid residues at its C-terminus. The Aβ(1-42) fragment is therefore believed to be mainly involved and responsible for the initiation of neuritic plaque formation in AD and to have, therefore, a high pathological potential. There is therefore a need for specific molecules that can target and diffuse-amyloid plaque formation.

The symptoms of AD manifest slowly and the first symptom may only be mild forgetfulness. In this stage, individuals may forget recent events, activities, the names of familiar people or things and may not be able to solve simple math problems. As the disease progresses, symptoms are more easily noticed and become serious enough to cause people with AD or their family members to seek medical help. Mid-stage symptoms of AD include forgetting how to do simple tasks such as grooming, and problems develop with speaking, understanding, reading, or writing. Later stage AD patients may become anxious or aggressive, may wander away from home and ultimately need total care.

Presently, the only definite way to diagnose AD is to identify plaques and tangles in brain tissue in an autopsy after death of the individual. Therefore, doctors can only make a diagnosis of "possible" or "probable" AD while the person is still alive. Using current methods, physicians can diagnose AD correctly up to 90 percent of the time using several tools to diagnose "probable" AD. Physicians ask questions about the person's general health, past medical problems, and the history of any difficulties the person has carrying out daily activities. Behavioral tests of memory, problem solving, attention, counting, and language provide information on cognitive degeneration and medical tests such as tests of blood, urine, or spinal fluid, and brain scans can provide some further information.

The management of AD consists of medication-based and non-medication based treatments. Treatments aimed at changing the underlying course of the disease (delaying or reversing the progression) have so far been largely unsuccessful. Medicines that restore the deficit (defect), or malfunctioning, in the chemical messengers of the nerve cells (neurotransmitters), in particular the cholinesterase inhibitors (ChEIs) such as tacrine and rivastigmine, have been shown to improve symptoms. ChEIs impede the enzymatic degradation of neurotransmitters thereby increasing the amount of chemical messengers available to transmit the nerve signals in the brain.

For some people in the early and middle stages of the disease, the drugs tacrine (COGNEX®, Morris Plains, N.J.), donepezil (ARICEPT®, Tokyo, JP), rivastigmine (EXELON®, East Hanover, N.J.), or galantamine (REMINYL®, New Brunswick, N.J.) may help prevent some symptoms from becoming worse for a limited time. Another drug, memantine (NAMENDA®, New York, N.Y.), has been approved for treatment of moderate to severe AD. Medications are also available to address the psychiatric manifestations of AD. Also, some medicines may help control behavioral symptoms of AD such as sleeplessness, agitation, wandering, anxiety, and depression. Treating these symptoms often makes patients more comfortable and makes their care easier for caregivers. Unfortunately, despite significant treatment advances showing that this class of agents is consistently better than a placebo, the disease continues to progress, and the average effect on mental functioning has only been modest. Many of the drugs used in AD medication such as, for example, ChEIs also have side effects that include gastrointestinal dysfunction, liver toxicity and weight loss.

Other diseases that are based on or associated with the accumulation and deposit of amyloid-like protein are mild cognitive impairment, Lewy body dementia (LBD), amyotrophic lateral sclerosis (ALS), inclusion-body myositis (IBM) and macular degeneration, in particular age-related macular degeneration (AMD).

Mild cognitive impairment (MCI) is a general term most commonly defined as a subtle but measurable memory disorder. A person with MCI experiences memory problems greater than normally expected with aging, but does not show other symptoms of dementia, such as impaired judgment or reasoning.

Lewy body dementia (LBD) is a neurodegenerative disorder that can occur in persons older than 65 years of age, which typically causes symptoms of cognitive (thinking) impairment and abnormal behavioral changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-1 protein were found to be increased inside the muscle cells of patients with this most common, progressive muscle disease of older people, in which amyloid-13 is also increased.

Macular degeneration is a common eye disease that causes deterioration of the macula, which is the central area of the retina (the paper-thin tissue at the back of the eye where light-sensitive cells send visual signals to the brain). Sharp, clear, 'straight ahead' vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contains amyloid beta. (Experimental Eye Research 78 (2004) 243-256).

Prions cause neurodegenerative diseases such as scrapie in sheep, bovine spongiform encephalopathy in cattle and Creutzfeldt-Jacob disease in humans. The only known component of the particle is the scrapie isoform of the protein, PrPSc. Although prions multiply, there is no evidence that they contain nucleic acid. PrPSc is derived from the non-infectious, cellular protein PrPC by a posttranslational process during which PrPC undergoes a profound conformational change.

The scrapie protein PrPSc has a critical role in neuronal degeneration and during disease development undergoes a three stage transition as follows: PrPC (normal cellular isoform of protein)—PrPSc: infectious form (scrapie isoform of protein)—protein PrP27-30.

Such a cascade of events occurs during the development of Creutzfeldt-Jacob disease (CJD), Kuru, Gerstmann-Straussler-Scheinker Syndrome (GSS), fatal familial insomnia in man, scrapie in sheep and goats, encephalopathy in mink and bovine spongiform encephalopathy in cattle.

The cellular non-toxic protein (PrPC) is a sialoglycoprotein of molecular weight 33000 to 35000 that is expressed predominantly in neurons. In the diseases mentioned above, PrPC is converted into an altered form (PrPSc), which is distinguishable from its normal homologue by its relative resistance to protease digestion. PrPSc accumulates in the central nervous system of affected animals and individuals and its protease-resistant core aggregates extracellularly.

Amyloidosis is not a single disease entity but rather a diverse group of progressive disease processes characterized by extracellular tissue deposits of a waxy, starch-like protein called amyloid, which accumulates in one or more organs or body systems. As the amyloid deposits build up, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs in people who have a chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Glaucoma is a group of diseases of the optic nerve involving loss of retinal ganglion cells (RGCs) in a characteristic pattern of optic neuropathy. Glaucoma is often, but not always, accompanied by an increased eye pressure, which may be a result of blockage of the circulation of aqueous, or its drainage.

Although raised intraocular pressure is a significant risk factor for developing glaucoma, no threshold of intraocular pressure can be defined which would be determinative for causing glaucoma.

The damage may also be caused by poor blood supply to the vital optic nerve fibers, a weakness in the structure of the nerve, and/or a problem in the health of the nerve fibers themselves.

Untreated glaucoma leads to permanent damage of the optic nerve and resultant visual field loss, which can progress to blindness.

RGCs are the nerve cells that transmit visual signals from the eye to the brain. Caspase-3 and Caspase-8, two major enzymes in the apoptotic process, are activated in the process leading to apoptosis of RGCs. Caspase-3 cleaves amyloid precursor protein (APP) to produce neurotoxic fragments, including Amyloid β. Without the protective effect of APP, Amyloid β accumulation in the retinal ganglion cell layer results in the death of RGCs and irreversible loss of vision.

The different types of glaucomas are classified as open-angle glaucomas, if the condition is chronic, or closed-angle glaucomas, if acute glaucoma occurs suddenly. Glaucoma usually affects both eyes, but the disease can progress more rapidly in one eye than in the other.

Chronic open-angle glaucoma (COAG), also known as primary open angle glaucoma (POAG), is the most common type of glaucoma. COAG is caused by microscopic blockage in the trabecular meshwork, which decreases the drainage of the aqueous outflow into the Schlemm's canal and raises the intraocular pressure (IOP). POAG usually affects both eyes and is strongly associated with age and a positive family history. Its frequency increases in elderly people as the eye drainage mechanism may gradually become clogged with aging. The increase in intraocular pressure in subjects affected by chronic open-angle glaucoma is not accompanied by any symptoms until the loss is felt on the central visual area.

Acute Angle Closure Glaucoma (AACG) or closed-angle glaucoma is a relatively rare type of glaucoma characterized by a sudden increase in intraocular pressure to 35 to 80 mmHg, leading to severe pain and irreversible loss of vision. The sudden pressure increase is caused by the closing of the filtering angle and blockage of the drainage channels. Individuals with narrow angles have an increased risk for a sudden closure of the angle. AACG usually occurs monocularly, but the risk exists in both eyes. Age, cataract and pseudoexfoliation are also risk factors since they are associated with enlargement of the lens and crowding or narrowing of the angle. A sudden glaucoma attack may be associated with severe eye pain and headache, inflamed eye, nausea, vomiting, and blurry vision.

Mixed or Combined Mechanism Glaucoma is a mixture or combination of open and closed angle glaucoma. It affects patients with acute ACG whose angle opens after laser iridotomy, but who continue to require medications for IOP control, as well as patients with POAG or pseudoexfoliative glaucoma who gradually develop narrowing of the angle.

Normal tension glaucoma (NTG), also known as low tension glaucoma (LTG), is characterized by progressive optic nerve damage and loss of peripheral vision similar to that seen in other types of glaucoma; however, the intraocular pressure is the normal range or even below normal.

Congenital (infantile) glaucoma is a relatively rare, inherited type of open-angle glaucoma. Insufficient development of the drainage area results in increased pressure in the eye that can lead to the loss of vision from optic nerve damage and to an enlarged eye. Early diagnosis and treatment are critical to preserve vision in infants and children affected by the disease.

Secondary glaucoma may result from an ocular injury, inflammation in the iris of the eye (iritis), diabetes, cataract, or use of steroids in steroid-susceptible individuals. Secondary glaucoma may also be associated with retinal detachment or retinal vein occlusion or blockage.

Pigmentary glaucoma is characterized by the detachment of granules of pigment from the iris. The granules cause blockage of the drainage system of the eye, leading to elevated intraocular pressure and damage to the optic nerve.

Exfoliative glaucoma (pseudoexfoliation) is characterized by deposits of flaky material on the anterior capsule and in the angle of the eye. Accumulation of the flaky material blocks the drainage system and raises the eye pressure.

Diagnosis of glaucoma may be made using various tests. Tonometry determines the pressure in the eye by measuring the tone or firmness of its surface. Several types of tonometers are available for this test, the most common being the applanation tonometer. Pachymetry determines the thickness of the cornea which, in turn, measures intraocular pressure. Gonioscopy allows examination of the filtering angle and drainage area of the eye. Gonioscopy can also determine if abnormal blood vessels may be blocking the drainage of the aqueous fluid out of the eye. Ophthalmoscopy allows examination of the optic nerve and can detect nerve fiber layer drop or changes in the optic disc, or indentation (cupping) of this structure, which may be caused by increased intraocular pressure or axonal drop out. Gonioscopy is also useful in assessing damage to the nerve from poor blood flow or increased intraocular pressure. Visual Field testing maps the field of vision, subjectively, which may detect signs of glaucomatous damage to the optic nerve. This is represented by specific patterns of visual field loss. Ocular coherence tomography, an objective measure of nerve fiber layer loss, is carried out by looking at the thickness of the optic nerve fiber layer (altered in glaucoma) via a differential in light transmission through damaged axonal tissue.

Optic nerve drusen are globular concretions of protein and calcium salts which are felt to represent secretions through congenitally altered vascular structures affecting the axonal nerve fiber layer. These accumulations occur in the peripapillary nerve fiber layer and are felt to damage the nerve fiber layer either directly by compression or indirectly through disruptions of the vascular supply to the nerve fiber layer. They usually become visible after the first decade of life in affected individuals. They occur most often in both eyes but may also affect one eye, and may cause mild loss of peripheral vision over many years.

Optic neuropathy is a disease characterized by damage to the optic nerve caused by demyelination, blockage of blood supply, nutritional deficiencies, or toxins. Demyelinating optic neuropathies (see optic neuritis below) are typically caused by an underlying demyelinating process such as multiple sclerosis. Blockage of the blood supply, known as ischemic optic neuropathy, can lead to death or dysfunction of optic nerve cells. Non-arteritic ischemic optic neuropathy usually occurs in middle-age people. Risk factors include high blood pressure, diabetes and atherosclerosis. Arteritic ischemic optic neuropathy usually occurs in older people following inflammation of the arteries (arteritis), particularly the temporal artery (temporal arteritis). Loss of vision may be rapid or develop gradually over 2 to 7 days and the damage may be to one or both eyes. In people with optic neuropathy caused by exposure to a toxin or to a nutritional deficiency, both eyes are usually affected.

About 40% of people with non-arteritic ischemic optic neuropathy experience spontaneous improvement over time. Non-arteritic ischemic optic neuropathy is treated by controlling blood pressure, diabetes and cholesterol levels. Arteritic ischemic optic neuropathy is treated with high doses of corticosteroids to prevent loss of vision in the second eye.

Optic neuritis is associated with mild or severe vision loss in one or both eyes and may be caused by a systemic demyelinating process (see above), viral infection, vaccination, meningitis, syphilis, multiple sclerosis and intraocular inflammation (uveitis). Eye movement may be painful and vision may deteriorate with repeat episodes. Diagnosis involves examination of the reactions of the pupils and determining whether the optic disk is swollen. Magnetic resonance imaging (MRI) may show evidence of multiple sclerosis or, rarely, a tumor pressing on the optic nerve, in which case vision improves once the tumor pressure is relieved. Most cases of optic neuritis improve over a few months without treatment. In some cases, treatment with intravenous corticosteroids may be necessary.

A cataract is an opacity that develops in the crystalline lens of the eye or in its envelope. Cataracts typically cause progressive vision loss and may cause blindness if left untreated. In the Morgagnian Cataract, the cataract cortex progressively liquefies to form a milky white fluid and may cause severe inflammation if the lens capsule ruptures and leaks. If left untreated, the cataract may also cause phacomorphic glaucoma. Cataracts may be congenital in nature or caused by genetic factors, advanced age, long-term ultraviolet exposure, exposure to radiation, diabetes, eye injury or physical trauma.

Extra-capsular (ECCE) surgery is the most effective treatment to treat cataract. In the surgery, the lens is removed, but the majority of the lens capsule is left intact. Phacoemulsification, a small incision on the side of the cornea, is typically used to break up the lens before extraction.

Ocular amyloidosis is a hereditary disorder associated with Type I Familial Amyloidotic Polyneuropathy (FAP) and characterized by abnormal conjunctival vessels, keratoconjunctivitis sicca, pupillary abnormalities and, in some cases, vitreous opacities and secondary glaucoma. Type I FAP is associated with mutations in transthyretin (TTR), a tetrameric plasma protein (prealbumin) synthesized in the liver, the retinal pigment epithelium 2 and thechoroid plexus of the brain. Different mutations cause transthyretin to polymerize into a pleated structure of amyloid fibril, leading to hereditary amyloidosis. The most frequent mutation is TTR-met303, in which methionine replaces valine at position 30 in transthyretin.

Type IV FAP is associated with lattice corneal dystrophy (LCD). Lattice corneal dystrophy is an inherited, primary, usually bilateral corneal amyloidosis characterized by the presence of refractile lattice lines with a double contour in the corneal stroma. LCD type I (Biber-Haab-Dimmer) is an autosomal dominant, bilaterally symmetrical corneal disorder characterized by the presence of numerous translucent fine lattice lines with white dots and faint haze in the superficial and middle layers of the central stroma. The symptoms start during the first or second decades of life, causing a progressive loss of vision. Most patients require a corneal transplant by 40 years of age. LCD type II is associated with systemic amyloidosis (Meretoja's syndrome) and is characterized by the presence of thick lattice lines in the limbus, central cornea and stroma. Vision is not affected until later in life. LCD type III affect middle-age people and is characterized by the presence of thick lattice lines that extend from limbus to limbus. LCD type III A is characterized by the accumulation of amyloid deposits in the stroma and the presence of ribbons of amyloid between the stroma and Bowman's layer, LCD type III A differs from LCD type III because of the presence of corneal erosions, the occurrence in whites and the autosomal dominant inheritance pattern.

Down's Syndrome (DS) or trisomy 21 is the most common genetic disorder with an incidence of about 1:700 live births, and is often associated with various congenital anomalies. The disorder, which is caused by the presence of an extra chromosome 21, is associated with premature deposits of the plaque-forming protein amyloid-beta and development of Alzheimer's disease by middle age. Furthermore, many people affected by DS suffer from cataracts beginning in childhood and many suffer from congenital glaucoma. Since the gene for amyloid precursor protein, which is cleaved to form amyloid beta, is located on the long arm of chromosome 21 in humans, overexpression of this gene may lead to increased levels of amyloid precursor protein and amyloid deposition in Down's syndrome.

There is no cure for glaucoma. Medications for the treatment of glaucoma include agents that decrease production of the aqueous humor in the eye, such as beta blockers (Timoptic, Betoptic), carbonic anhydrase inhibitors (Trusopt, Azopt), and alpha agonists (Alphagan, Iopidine), and agents that redirect drainage of the aqueous humor through a different pathway at the back of the eye, such as prostaglandin (Xalatan). Laser surgeries include trabeculoplasty, a procedure that helps the aqueous humor leave the eye more efficiently. According to the Glaucoma Foundation, nearly 80% of patients respond well enough to the procedure to delay or avoid further surgery. However, pressure increases again in the eyes of half of all patients within two years after laser surgery, according to the National Eye Institute. Incisional surgery is performed if medication and initial laser treatments are unsuccessful in reducing pressure within the eye. One type of surgery, a trabeculectomy, creates an opening in the wall of the eye so that aqueous humor can drain. However, about one-third of trabeculectomy patients develop cataracts within five years, according to the Glaucoma Foundation. If the trabeculectomy fails, additional incisional procedures include placing a drainage tube into the eye between the cornea and iris and the use of a laser or freezing treatment to destroy tissue in the eye that makes aqueous humor. Surgery may save the remaining vision in the patient, but it does not improve sight. Vision may actually be worse following surgery.

Age-related macular degeneration (AMD) is a major cause of blindness among Caucasians over age 65. Although much progress has been made recently in macular degeneration research, there are no treatments that rescue neuronal cell death that occurs during the course of the disease. There are also no definitive treatments for other ocular diseases associated with amyloid beta-related neuronal degradation, such as cortical visual deficits, optic nerve drusen, optic neuropathy, optic neuritis, ocular amyloidosis and lattice dystrophy.

Amyloid deposits typically contain three components. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein. In addition, amyloid deposits are closely associated with the amyloid P (pentagonal) component (AP), a glycoprotein related to normal serum amyloid P (SAP), and with sulphated glycosaminoglycans (GAG), complex carbohydrates of connective tissue.

One development towards the treatment of Alzheimer's disease and prion diseases has been the design of molecules that bind the abnormal β-sheet conformation of Aβ and PrP, respectively, thereby preventing aggregation of these molecules. The β-sheet conformation of peptides is characterized in that hydrogen bonds are formed in a regular pattern between neighboring amino acid strands. This arrangement leads to a stable three dimensional structure. H-bond acceptors (C=O group) and H-bond donors (NH group) alternate in naturally occurring β-sheet peptides with the atoms to be bonded being roughly in one line. Within each amino acid strand, the distances between neighboring H-bond donors and H-bond acceptors fall within specific ranges. In particular, the distance between the H-bond donor (NH group) and the H-bond acceptor (C=O group) within one amino acid residue is from 3.5 to 4.0 Å. The distance between the H-bond acceptor (C=O group) of one amino acid residue and the H-bond donor (NH group) of the following amino acid residue participating in the inter-strand bonding is from 2.6 to 2.9 Å. In other words, the distances between neighboring H-bond donors and H-bond acceptors within one amino acid strand alternate between the following ranges:

H-bond donor(amino acid 1)–H-bond acceptor(amino acid 1)=3.5 to 4.0 Å;

H-bond acceptor(amino acid 1)–H-bond donor 2(amino acid 2)=2.6 to 2.9 Å.

Ligands that are designed to bind β-sheets ideally have an order of H-bond donors and H-bond acceptors that is complementary to the order of H-bond donors and H-bond acceptors in the amino acid strands of the β-sheet.

In WO 03/095429 and Rzepecki et al., Synthesis (2003) 12, 1815-1826 synthetic molecules are described which are said to bind the β-conformation of Aβ or PrP, thereby preventing their aggregation. To this end, certain molecules were synthesized containing two or more amino pyrazole moieties linked by carbonyl group-containing linkers, e.g. "AmpOx" and "Trimer".

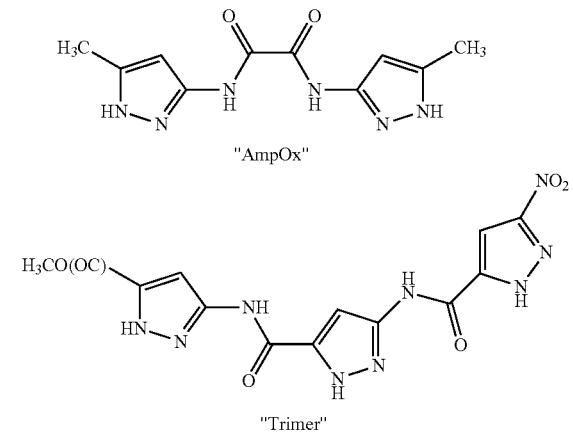

Some of the molecules described in WO 03/095429 are said to have an inhibiting effect on the formation of aggregates of Aβ in two biophysical assays. According to Rzepecki et al., Synthesis (2003) 12, 1815-1826 one of the molecules described therein was able to reduce the aggregation of a recombinant PrP$^c$ in solution. Physicochemical properties, however, were not investigated in these studies.

Physicochemical properties play a key role in the penetration of the blood-brain barrier by neurotherapeutics. Factors relevant to the success of CNS drugs have been reviewed (H. Pajouhesh and G. R. Lenz, NeuroRx®: J. Am. Soc. Exp. Neurother. (2005) Vol. 2, 541). These include the partition coefficient between water and n-octanol (LogP), i.e. basically the lipophilicity of the compound. Some of the compounds described in WO 03/095429 and Rzepecki et al., Synthesis (2003) 12, 1815-1826 have an unfavorable calculated LogP and are, therefore, not expected to pass the blood-brain barrier. In particular, "AmpOx" has a calculated LogP below zero.

Other compounds described in the above documents have properties that make them unsuitable for administration to a patient due to their deleterious side-effects. For example, "Trimer" is mutagenic, carcinogenic and metabolically unstable.

It was an object of the present invention to provide compounds that can be employed in the treatment of diseases or conditions associated with amyloid or amyloid-like proteins, including amyloidosis. The compounds should be able to pass the blood-brain barrier. Furthermore, they should be pharmaceutically acceptable, in particular, they should not have mutagenic or carcinogenic properties or be metabolically unstable.

A further object of the invention is to provide improved treatment options for subjects affected by ocular diseases associated with pathological abnormalities/changes in the tissues of the visual system, particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidoses; the retina leading to primary retinal degeneration and macular degeneration, for example age-related macular degeneration; the optic nerve leading to optic nerve drusen, optic neuropathy and optic neuritis; and the cornea leading to lattice dystrophy.

The present inventors have surprisingly found that these objects can be achieved by the compounds of the general formula (II) as described hereinafter.

Accordingly, the present invention relates to a compound of general formula (II).

In a further aspect, the present invention relates to a pharmaceutical composition comprising a compound of general formula (II).

Yet another aspect of the present invention relates to the use of a compound of general formula (II) for the preparation of a medicament for the treatment of diseases or conditions associated with amyloid or amyloid-like proteins, including amyloidosis.

Also disclosed herein is a method of treating diseases or conditions associated with amyloid or amyloid-like proteins, comprising administering to a subject in need of such treatment an effective amount of a compound of general formula (II).

Yet another aspect of the present invention relates to the use of a compound of general formula (I) for the preparation of a medicament for treating or alleviating the effects of ocular diseases associated with pathological abnormalities/changes in the tissues of the visual system.

Also disclosed herein is a method of treating or alleviating the effects of ocular diseases associated with pathological abnormalities/changes in the tissues of the visual system comprising administering to a subject in need of such treatment an effective amount of a compound of general formula (I).

The ocular diseases associated with pathological abnormalities/changes in the tissues of the visual system are particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidoses; the retina leading to primary retinal degeneration and macular degeneration, for example age-related macular degeneration; the optic nerve leading to optic nerve drusen, optic neuropathy and optic neuritis; and the cornea leading to lattice dystrophy.

In a further aspect the invention relates to a mixture (such as a pharmaceutical composition) comprising a compound according to the present invention and optionally at least one further biologically active compound and/or a pharmaceutically acceptable carrier and/or a diluent and/or an excipient. The further biologically active substance can be a known compound used in the medication of diseases and disorders which are caused by or associated with amyloid or amyloid-like proteins including amyloidosis, a group of diseases and disorders associated with amyloid or amyloid-like protein such as the Aβ protein involved in Alzheimer's disease.

The further biologically active substance or compound may exert its biological effect by the same or a similar mechanism as the compound according to the invention or by an unrelated mechanism of action or by a multiplicity of related and/or unrelated mechanisms of action.

A method of collecting data for the diagnosis of an amyloid-associated disease or condition in a sample or a patient is also disclosed which comprises:
(a) bringing a sample or a specific body part or body area suspected to contain an amyloid protein into contact with a compound according to the present invention;
(b) allowing the compound to bind to the amyloid protein;
(c) detecting the compound bound to the protein; and
(d) optionally correlating the presence or absence of compound binding with the amyloid protein with the presence or absence of amyloid protein in the sample or specific body part or area.

Another embodiment of the present invention is a method of determining the extent of amyloidogenic plaque burden in a tissue and/or a body fluid comprising:
(a) providing a sample representative of the tissue and/or body fluid under investigation;
(b) testing the sample for the presence of amyloid protein with a compound according to the present invention;
(c) determining the amount of compound bound to the amyloid protein; and
(d) calculating the plaque burden in the tissue and/or body fluid.

A further aspect relates to a method of collecting data for determining a predisposition to an amyloid-associated disease or condition in a patient comprising detecting the specific binding of a compound according to the present invention to an amyloid protein in a sample or in situ which comprises the steps of:
(a) bringing the sample or a specific body part or body area suspected to contain the amyloid protein into contact with a compound according to the present invention, which compound specifically binds to the amyloid protein;
(b) allowing the compound to bind to the amyloid protein to form a compound/protein complex;
(c) detecting the formation of the compound/protein complex;
(d) optionally correlating the presence or absence of the compound/protein complex with the presence or absence of amyloid protein in the sample or specific body part or area; and
(e) optionally comparing the amount of the compound/protein complex to a normal control value.

Yet another aspect of the present invention is a method of collecting data for monitoring minimal residual disease in a patient following treatment with an antibody or a vaccine composition, wherein the method comprises:
(a) bringing a sample or a specific body part or body area suspected to contain an amyloid protein into contact with a compound according to the present invention, which compound specifically binds to the amyloid protein;
(b) allowing the compound to bind to the amyloid protein to form a compound/protein complex;

(c) detecting the formation of the compound/protein complex;
(d) optionally correlating the presence or absence of the compound/protein complex with the presence or absence of amyloid protein in the sample or specific body part or body area; and
(e) optionally comparing the amount of the compound/protein complex to a normal control value.

A method of collecting data for predicting responsiveness of a patient being treated with an antibody or a vaccine composition is also described which comprises:
(a) bringing a sample or a specific body part or body area suspected to contain an amyloid protein into contact with a compound according to the present invention, which compound specifically binds to the amyloid protein;
(b) allowing the compound to bind to the amyloid protein to form a compound/protein complex;
(c) detecting the formation of the compound/protein complex;
(d) optionally correlating the presence or absence of the compound/protein complex with the presence or absence of amyloid protein in the sample or specific body part or body area; and
(e) optionally comparing the amount of the compound/protein complex to a normal control value.

A further aspect of the present invention is a test kit for detection and diagnosis of an amyloid-associated disease or condition comprising a compound according to the present invention.

In a first embodiment the present invention relates to a compound of the general formula (II)

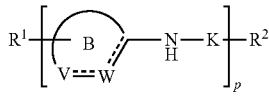
(II)

═ independently represents a single bond or a double bond. It is evident that the selection of the two ═ should lead to a compound having sufficient stability for pharmaceutical applications. Therefore, in a first preferred alternative one ═ is a double bond and the other ═ is a single bond or in a second preferred alternative both ═ are a single bond. It will be understood that the first preferred alternative, wherein one ═ is a double bond and the other ═ is a single bond, includes embodiments, wherein the two ═ are part of an aromatic system.

p is 1, 2 or 3.

Each linker K is independently $C_{1-3}$ alkylene which is optionally substituted by one or more $C_{1-4}$ alkyl groups. Preferably, each linker K is —$CH_2$—, —$CH_2CH_2$— or —$CH_2CH_2CH_2$—.

Each B is independently a 5- or 6-membered saturated or unsaturated heterocyclic ring, wherein the heterocyclic ring B is optionally substituted by one or more, preferably one or two, substituents selected from $C_{1-4}$ alkyl, $C_{1-4}$ alkoxy, mono- and di-$C_{1-4}$ alkyl amino, $C_{3-7}$ cycloalkyl amino, and 5- or 6-membered saturated heterocyclyl, or two substituents may be joined to form a saturated, unsaturated or aromatic 5- to 7-membered ring which is fused with the heterocyclic ring B, and wherein the heterocyclic ring B may contain in addition to the units V and W one or more, preferably one or two, heteroatoms, selected from N, NR, S and O, wherein R is selected from H and $C_{1-4}$ alkyl.

The 5- or 6-membered saturated heterocyclyl group contains carbon atoms and 1 or more, preferably 1 or 2, heteroatoms selected from N, NH, O and S. The nitrogen and sulfur atoms may optionally be oxidized. The 5- or 6-membered saturated heterocyclyl group may be attached to its pendant group at any heteroatom or carbon atom. Examples of the 5- or 6-membered saturated heterocyclyl group include, but are not limited to, pyrrolidinyl, piperidinyl and morpholinyl.

Preferably, each heterocyclic ring B is independently selected from optionally substituted indoline, optionally substituted pyrazolylene, optionally substituted pyridinylene, optionally substituted 2-pyridinonylene, optionally substituted 2-piperidonylene, optionally substituted thiazolylene and optionally substituted isothiazolylene. More preferably, each heterocyclic ring B is independently selected from the following groups:

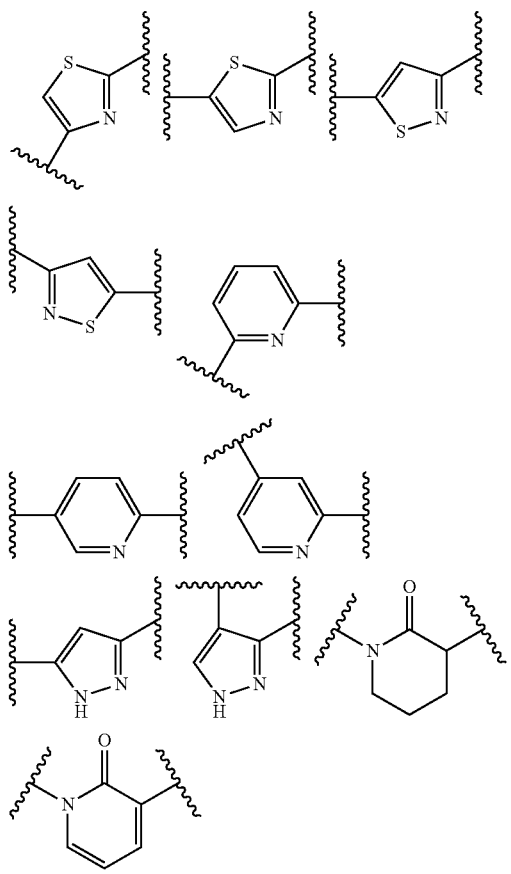

These groups need not be incorporated in the indicated direction but can also be incorporated in the opposite direction. E.g.,

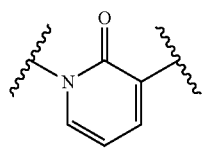 [SMILES: *c1cccn(*)c1=O]

can also be incorporated as

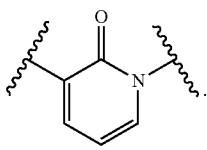 [SMILES: *c1cccn(*)c1=O]

Preferably, however, they are incorporated in the given direction.

$R^1$ is selected from —H, -halogen, —$C_{1-4}$ alkyl, —$NH_2$, —NH—$C_{1-4}$ alkyl, —$C_{1-4}$ alkylene-$NH_2$, —$C_{1-4}$ alkylene-NH—$C_{1-4}$ alkyl, -aryl, -aryl-$R^3$, —$C_{1-4}$ alkylene-aryl, —$C_{1-4}$ alkylene-aryl-$R^3$, -heteroaryl, -heteroaryl-$R^3$, —NH—$C_{1-4}$ alkylene-aryl, —NH—$C_{1-4}$ alkylene-aryl-$R^3$, —OH and —O—$C_{1-4}$ alkyl. $R^1$ is preferably —H, —$CH_3$, —NH—$C_{1-4}$ alkyl or —$CH_2$—NH—$CH_3$.

$R^3$ is $C_{1-4}$ alkyl, halogen, OH or O—$C_{1-4}$ alkyl.

$R^2$ is —H, -aryl, —$C_{1-4}$ alkyl or a group of the formula

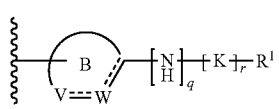

(II)

wherein B, V, W and K are as defined above, q is 0 or 1 and r is 0 or 1. Preferably, $R^2$ is H or aryl.

Each unit W is independently a H-bond acceptor. Preferably, each unit W is independently N or C=O.

Each unit V is independently optional and, if present, is independently a H-bond donor. Each unit V is preferably NH.

Aryl is preferably a 5- to 7-membered aryl such as phenyl.

Heteroaryl is preferably a 5- to 7-membered heteroaryl (preferably a 5-membered heteroaryl), which includes at least one heteroatom selected from O, S or N. Examples are

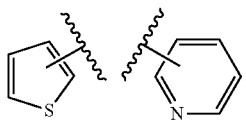

Halogen is preferably F or Cl.

In one embodiment the compounds of the formula (II) have the formula (II')

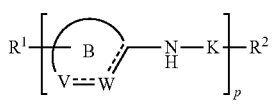

(II')

≡ independently represents a single bond or a double bond. It is evident that the selection of the two ≡ should lead to a compound having sufficient stability for pharmaceutical applications. Therefore, in a first preferred alternative one ≡ is a double bond and the other ≡ is a single bond or in a second preferred alternative both ≡ are a single bond. It will be understood that the first preferred alternative wherein one ≡ is a double bond and the other ≡ is a single bond, includes embodiments, wherein the two ≡ are part of an aromatic system.

p is 2 or 3.

Each linker K is independently $C_{1-3}$ alkylene which is optionally substituted by one or more $C_{1-4}$ alkyl groups. Preferably, each linker K is —$CH_2$— or —$CH_2CH_2$—.

Each B is independently a 5- or 6-membered heterocyclic ring, wherein the heterocyclic ring B is optionally substituted by one or more, preferably one or two, substituents selected from $C_{1-4}$ alkyl, $C_{1-4}$ alkoxy, mono and di $C_{1-4}$ alkyl amino, $C_{3-7}$ cycloalkyl amino, and 5- or 6-membered saturated heterocyclyl, or two substituents may be joined to form a saturated, unsaturated or aromatic 5- to 7-membered ring which is fused with the heterocyclic ring B, and wherein the heterocyclic ring B may contain in addition to the units V and W one or more, preferably one or two, heteroatoms, selected from N, NR, S and O, wherein R is selected from H and $C_{1-4}$ alkyl. The 5- or 6-membered saturated heterocyclyl group contains carbon atoms and 1 or more, preferably 1 or 2, heteroatoms selected from N, NH, O and S. The nitrogen and sulfur atoms may optionally be oxidized. The 5- or 6-membered saturated heterocyclyl group may be attached to its pendant group at any heteroatom or carbon atom. Examples of the 5- or 6-membered saturated heterocyclyl group include, but are not limited to, pyrrolidinyl, piperidinyl and morpholinyl.

Preferably, each heterocyclic ring B is independently selected from optionally substituted pyrazolylene, optionally substituted pyridinylene, optionally substituted 2-pyridinonylene, optionally substituted 2-piperidonylene, optionally substituted thiazolylene and optionally substituted isothiazolylene. More preferably, each heterocyclic ring B is independently selected from the following groups:

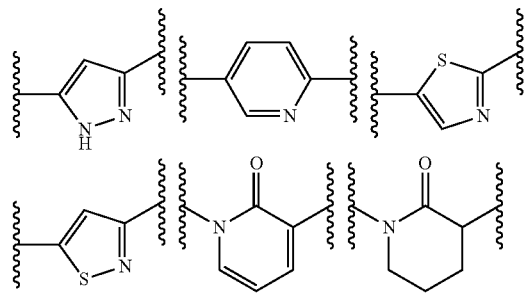

$R^1$ is selected from H, $C_{1-4}$ alkyl, $NH_2$, NH—$C_{1-4}$ alkyl, $C_{1-4}$ alkylene-$NH_2$, $C_{1-4}$ alkylene-NH—$C_{1-4}$ alkyl, OH and O—$C_{1-4}$ alkyl. $R^1$ is preferably H, $CH_3$, NH—$CH_3$ or $CH_2$—NH—$CH_3$.

$R^2$ is H, or a group of the formula

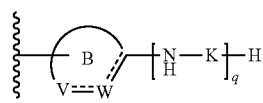

wherein B, V, W and K are as defined above and q is 0 or 1.

Preferably, $R^2$ is H.

Each unit W is independently a H-bond acceptor. Preferably, each unit W is independently N or C=O.

Each unit V is independently optional and, if present, is independently a H-bond donor. Each unit V is preferably NH.

Preferred compounds are summarized in the following table.

| | |
|---|---|
| 2a | 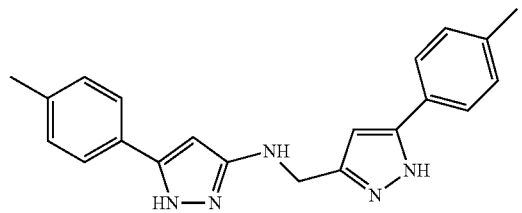 |
| 2c | 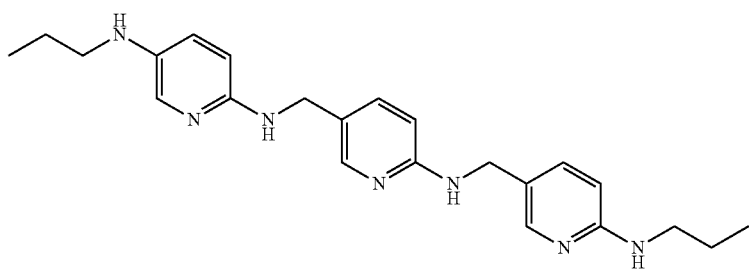 [SMILES: CCCNc1ccc(NCc2ccc(NCc3ccc(NCCC)nc3)nc2)nc1] |
| 2h | 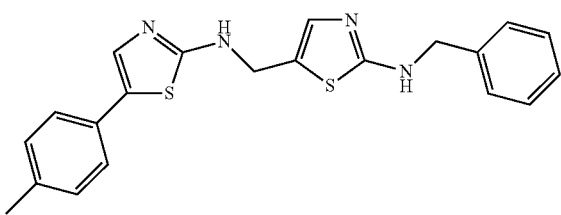 [SMILES: Cc1ccc(-c2cnc(NCc3cnc(NCc4ccccc4)s3)s2)cc1] |
| 2j | 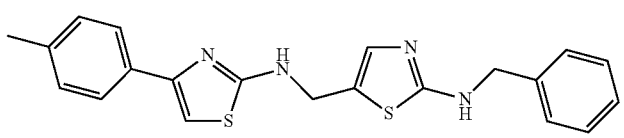 [SMILES: Cc1ccc(-c2csc(NCc3cnc(NCc4ccccc4)s3)n2)cc1] |
| 2k | 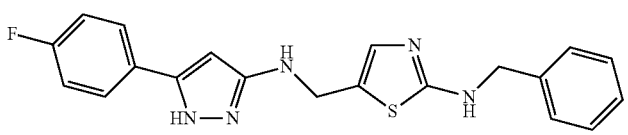 [SMILES: Fc1ccc(-c2cc(NCc3cnc(NCc4ccccc4)s3)n[nH]2)cc1] |
| 2n | 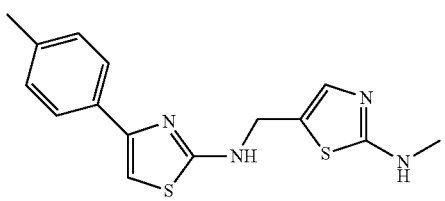 |
| 2o | 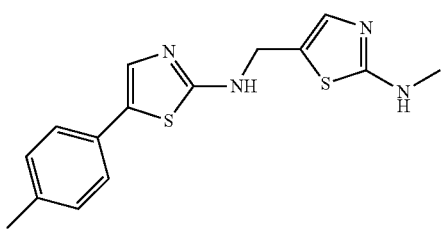 |
| 2p | 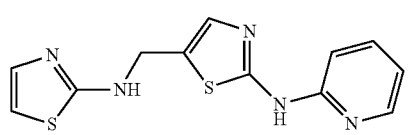 [SMILES: c1ccc(Nc2ncc(CNc3nccs3)s2)nc1] |

-continued
2q 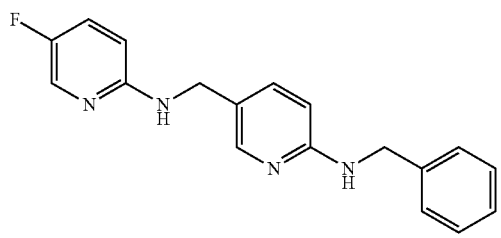 [SMILES: Fc1ccc(NCc2ccc(NCc3ccccc3)nc2)nc1]
2s 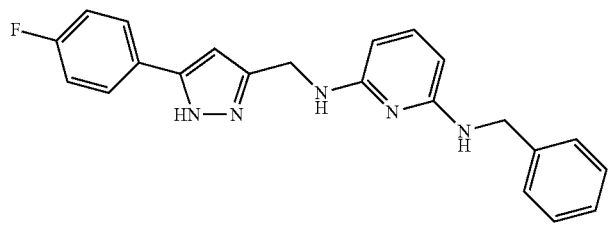 [SMILES: Fc1ccc(-c2cc(CNc3cccc(NCc4ccccc4)n3)n[nH]2)cc1]
2t 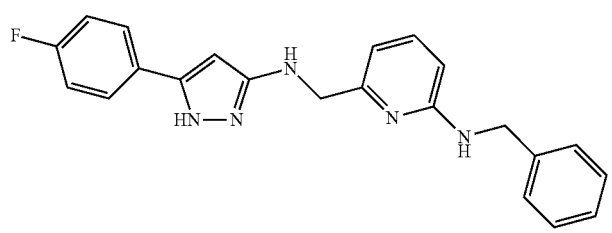 [SMILES: Fc1ccc(-c2cc(NCc3cccc(NCc4ccccc4)n3)n[nH]2)cc1]
2u 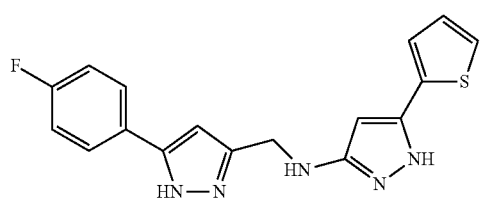 [SMILES: Fc1ccc(-c2cc(CNc3cc(-c4cccs4)[nH]n3)n[nH]2)cc1]
2w 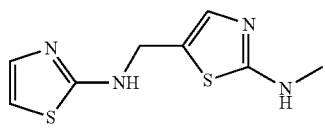
2y 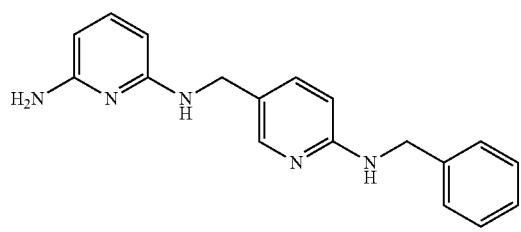 [SMILES: Nc1cccc(NCc2ccc(NCc3ccccc3)nc2)n1]
2z 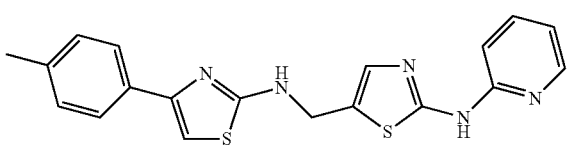 [SMILES: Cc1ccc(-c2csc(NCc3cnc(Nc4ccccn4)s3)n2)cc1]
2aa 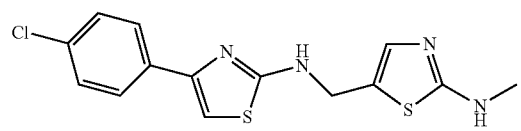 [SMILES: CNc1ncc(CNc2nc(-c3ccc(Cl)cc3)cs2)s1]

-continued
| | |
|---|---|
| 2ab | 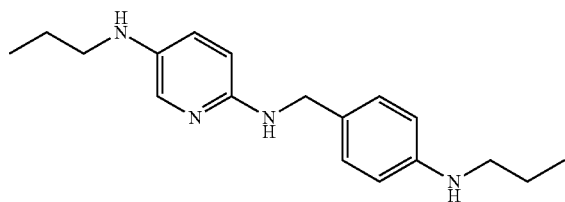 [SMILES: CCCNc1ccc(CNc2ccc(NCCC)cn2)cc1] |
| 2ac | 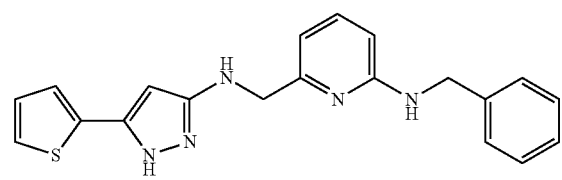 [SMILES: c1ccc(CNc2cccc(CNc3cc(-c4cccs4)[nH]n3)n2)cc1] |
| 2ad | 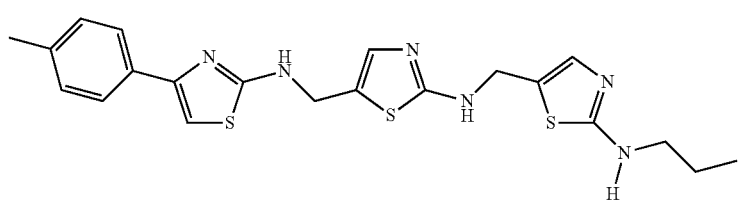 [SMILES: CCCNc1ncc(CNc2ncc(CNc3nc(-c4ccc(C)cc4)cs3)s2)s1] |
| 2ae | 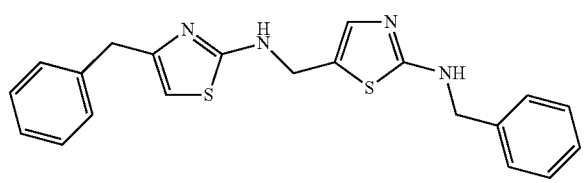 [SMILES: c1ccc(CNc2ncc(CNc3nc(Cc4ccccc4)cs3)s2)cc1] |
| 2af | 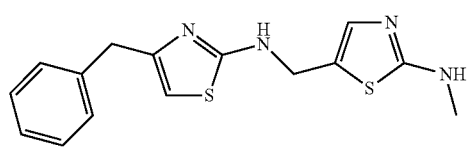 [SMILES: CNc1ncc(CNc2nc(Cc3ccccc3)cs2)s1] |
| 2ag | 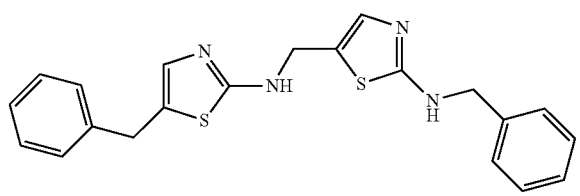 [SMILES: c1ccc(CNc2ncc(CNc3ncc(Cc4ccccc4)s3)s2)cc1] |
| 2ah | 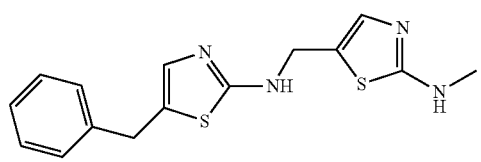 [SMILES: CNc1ncc(CNc2ncc(Cc3ccccc3)s2)s1] |
| 2ai | 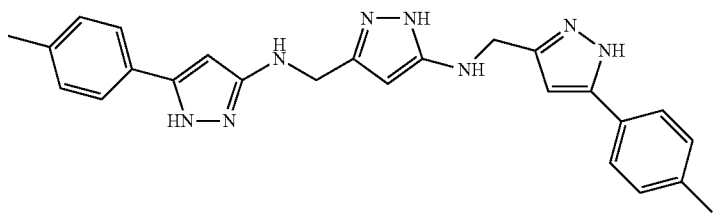 |

2ak 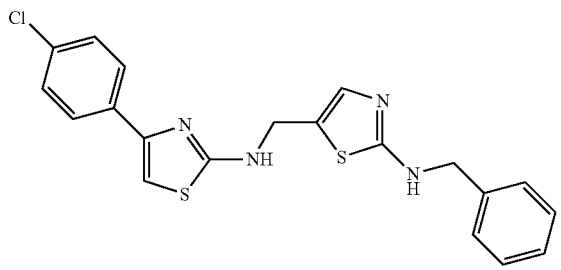 [SMILES: Clc1ccc(-c2csc(NCc3cnc(NCc4ccccc4)s3)n2)cc1]

2al 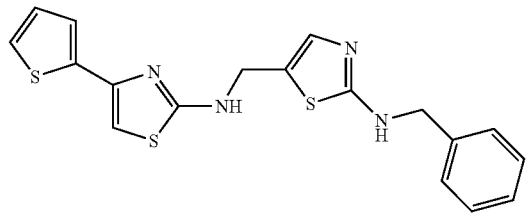 [SMILES: c1ccc(CNc2ncc(CNc3nc(-c4cccs4)cs3)s2)cc1]

2am 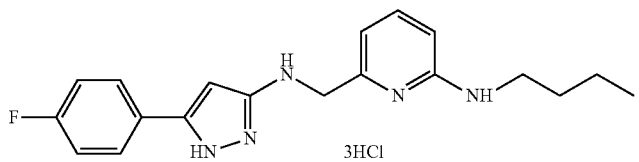 [SMILES: CCCCNc1cccc(CNc2cc(-c3ccc(F)cc3)[nH]n2)n1 ; "3HCl"]

In the compounds of the present invention H-bond donors and H-bond acceptors are preferably arranged in a pattern which is essentially complementary to the pattern of H-bond donors and H-bond acceptors present in the amino acid strands of β-sheet structures as set out in the introductory part. In particular, the distances between neighboring H-bond donors and H-bond acceptors in the compounds of the present invention are preferably within the range of 2.6 to 2.9 Å or 3.5 to 4.0 Å.

The distances between neighboring H-bond donors and H-bond acceptors in the compounds of the present invention can, for example, directly measured from the Dreiding models of the compounds. Alternatively, molecular modeling computer programs, such as MacroModel 7.2, can be used for the distance determination.

The compounds of the present invention do not only feature a H-bond donor/acceptor pattern which promotes their binding to the amino acid strands of β-sheet structures, they also have favorable physicochemical properties which facilitate their use as neurotherapeutics. In particular, their lipophilicity is in a range which should enhance their penetration of the blood-brain barrier. Preferably, the calculated partition coefficient (milogP) between water and n-octanol of the compounds of the present invention is in the range of from 0 and 4, more preferably from 1 to 3.

milogP values can be calculated according to the software available on the world wide web (www.molinspiration.com), provided by P. Ertl of Novartis Pharma AG. A copy of the software is also available from the applicant.

In addition to lipophilicity, the polar surface area (PSA) of a molecule is an important factor for the determination of the suitability of a compound as a neurotherapeutic (H. Pajouhesh et al., NeuroRx®: J. Am. Soc. Exp. Neurother. (2005) Vol. 2, 541). The PSA is defined as the surface area (Å$^2$) occupied by nitrogen and oxygen atoms and the polar hydrogens attached to them. It is strongly reflective of hydrogen bonding capacity and polarity. While PSA takes into account the three-dimensional structure of a molecule, topological PSA (TPSA) is based on the corresponding two-dimensional structure. PSA and TPSA provide similar results, with TPSA enabling a significantly larger throughput due to its computationally less intensive two-dimensional representation. The compounds of the present invention generally have a TPSA which facilitates penetration of the blood-brain barrier. Preferably, the TPSA of the compounds of the present invention is equal to or below 90 Å$^2$.

TPSA values can be calculated according to the software available on the world wide web (www.molinspiration.com), provided by P. Ertl of Novartis Pharma AG. A copy of the software is also available from the applicant.

The compounds of the general formula (II) can be built stepwise via formation of peptide bonds and subsequent reduction with borane dimethylsulfide complex to yield the secondary amines.

While it is possible for the compounds of the present invention to be administered alone, it is preferable to formulate them into a pharmaceutical composition in accordance with standard pharmaceutical practice. Thus the invention also provides a pharmaceutical composition which comprises a therapeutically effective amount of a compound of formula (II) in admixture with a pharmaceutically acceptable excipient.

Pharmaceutically acceptable excipients are well known in the pharmaceutical art, and are described, for example, in Remington's Pharmaceutical Sciences, 15$^{th}$ Ed., Mack Publishing Co., New Jersey (1991). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, and ion exchange resins.

The routes for administration (delivery) of the compounds of the invention include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

A proposed dose of the compounds according to the present invention for administration to a human (of approximately 70 kg body weight) is 0.1 mg to 1 g, preferably 1 mg to 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may also be used in combination with other therapeutic agents. When a compound of the invention is used in combination with a second therapeutic agent active against the same disease the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

Diseases that can be treated with the compounds of the present invention can be associated with the formation of abnormal protein structures, in particular abnormal n-sheet structures. In the context of the present invention, an abnormal protein structure is a protein structure that arises when a protein or peptide refolds from the three-dimensional structure, which it generally adopts in healthy individuals, into a different three-dimensional structure, which is associated with a pathological condition. Likewise, an abnormal β-sheet structure in the context of the present invention is a β-sheet structure that arises when a protein or peptide refolds from the three-dimensional structure, which it generally adopts in healthy individuals, into a β-sheet structure, which is associated with a pathological condition.

In particular, in one embodiment diseases that can be treated with the compounds of the present invention are diseases or conditions associated with amyloid or amyloid-like proteins.

This group of diseases and disorders include neurological disorders such as Alzheimer's Disease (AD), diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidoses; the retina, including primary retinal degenerations and macular degeneration, in particular age-related macular degeneration; the optic nerve, including optic nerve drusen, optic neuropathy and optic neuritis; and the cornea, including lattice dystrophy.

In a preferred embodiment the compounds of the present invention can be employed for the treatment of Alzheimer's disease, mild cognitive impairment (MCI), Lewy body dementia (LBD), amyotropic lateral sclerosis (ALS), inclusion-body myositis (IBM) and age-related macular degeneration (AMD). In a particulary preferred embodiment the compounds of the present invention can be employed for the treatment of Alzheimer's disease.

The ability of a compound to inhibit the aggregation of Aβ can, for example, be determined using fluorescence correlation spectroscopy as described in Rzepecki et al., J. Biol. Chem., 2004, 279(46), 47497-47505 or by using the thioflavin T spectrofluorescence assay.

In another embodiment the compounds of the present invention can be used for treating or alleviating the effects of ocular diseases associated with pathological abnormalities/changes in the tissues of the visual system, particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidoses; the retina leading to primary retinal degeneration and macular degeneration, for example age-related macular degeneration; the optic nerve leading to optic nerve drusen, optic neuropathy and optic neuritis; and the cornea leading to lattice dystrophy.

The compounds according to the present invention can also be provided in the form of a mixture with at least one further biologically active compound and/or a pharmaceutically acceptable carrier and/or a diluent and/or an excipient. The compound and/or the further biologically active compound are preferably present in a therapeutically effective amount.

The nature of the further biologically active compound will depend on the intended use of the mixture. The further biologically active substance or compound may exert its biological effect by the same or a similar mechanism as the compound according to the invention or by an unrelated mechanism of action or by a multiplicity of related and/or unrelated mechanisms of action.

Generally, the further biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the further biologically active compound can be selected from the group consisting of a compound used in the treatment of amyloidoses, compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or tau modifying drug and nutritive supplements, an antibody, including any functionally equivalent antibody or functional parts thereof, an Aβ3 antigenic peptide fragment consisting of a single or repetitive stretch of a plurality of contiguous amino acid residues from the N-terminal part of the Aβ peptide.

In a further embodiment, the mixtures according to the invention may comprise niacin or memantine together with a compound according to the present invention and, optionally, a pharmaceutically acceptable carrier and/or a diluent and/or an excipient.

In still another embodiment of the invention mixtures are provided that comprise as a further biologically active compound "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with a compound according to the invention and, optionally, a pharmaceutically acceptable carrier and/or a diluent and/or an excipient.

Other compounds that can be suitably used in mixtures in combination with the compound according to the present invention are, for example, described in WO 2004/058258 (see especially pages 16 and 17) including therapeutic drug targets (pages 36 to 39), alkanesulfonic acids and alkanolsulfuric acids (pages 39 to 51), cholinesterase inhibitors (pages 51 to 56), NMDA receptor antagonists (pages 56 to 58), estrogens (pages 58 to 59), non-steroidal anti-inflammatory drugs (pages 60 and 61), antioxidants (pages 61 and 62), peroxisome proliferators-activated receptor (PPAR) agonists (pages 63 to 67), cholesterol-lowering agents (pages 68 to 75), amyloid inhibitors (pages 75 to 77), amyloid formation inhibitors (pages 77 to 78), metal chelators (pages 78 and 79), anti-psychotics and anti-depressants (pages 80 to 82), nutritional supplements (pages 83 to 89) and compounds increasing the availability of biologically active substances in the brain (see pages 89 to 3) and prodrugs (pages 93 and 94), which document is incorporated herein by reference.

In one preferred embodiment the further biologically active compound is an antibody including any functionally equivalent antibody or functional parts thereof. The antibody can preferably be monoclonal, chimeric or humanized.

In a further aspect of the invention, a mixture is provided comprising in addition to the compound of the invention an antibody including functional parts thereof, or, more particularly, a monoclonal antibody including functional parts thereof, which recognizes and binds to amyloid β (Aβ), particularly to the native conformation of amyloid β, that is to amyloid oligomers and fibers, but not to not linearized amyloid species.

In particular, said antibodies are capable of inhibiting, in vitro and in vivo, the aggregation of amyloidogenic monomeric peptides, specifically β-amyloid monomeric peptides such as, for example, Aβ monomeric peptides 1-39; 1-40, 1-41, 1-42, or 1-43, but especially $A\beta_{1-42}$ monomeric peptides, into high molecular polymeric amyloid fibrils or filaments. Through the inhibition of the aggregation of amyloidogenic monomeric peptides these antibodies are capable of preventing or slowing down the formation of amyloid plaques, particularly the amyloid form (1-42), which is know to become insoluble by change of secondary conformation and to be the major part of amyloid plaques in brains of diseased animals or humans.

In another aspect of the invention, the mixture comprises antibodies which, upon co-incubation with preformed high molecular polymeric amyloid fibrils or filaments formed by the aggregation of amyloid monomeric peptides, specifically β-amyloid monomeric peptides such as, for example, Aβ monomeric peptides 1-39; 1-40, 1-41, 1-42, or 1-43, but especially $A\beta_{1-42}$ monomeric peptides, are capable of disaggregating said high molecular polymeric amyloid fibrils or filaments. Through the disaggregation of amyloidogenic polymeric fibrils or filaments these antibodies are capable of preventing or slowing down the formation of amyloid plaques which leads to an alleviation of the symptoms associated with the disease and a delay or reversal of its progression.

In still another aspect of the invention, the mixture comprises an antibody, but especially a monoclonal antibody or functional parts thereof, which antibody is bifunctional or bispecific in that it exhibit both an aggregation inhibition property as well as a disaggregation property as defined herein before, particularly paired with a high degree of conformational sensitivity.

In one embodiment, the mixture comprises an antibody which recognizes and binds to a conformational epitope, particularly conformational epitope which is present in the N-terminal part of the amyloid β peptide, particularly embedded into the following core region of the N-terminal part of the amyloid β peptide:

| Val- | His- | His- | Gln- | Lys- | Leu- | Val- | Phe- | Phe- | Ala- |
|------|------|------|------|------|------|------|------|------|------|
| 12   | 13   | 14   | 15   | 16   | 17   | 18   | 19   | 20   | 21   |

| Glu- | Asp- |
|------|------|
| 22   | 23   |

Particularly an epitope localized in a region of the β-amyloid protein between amino acid residue 12 to 24, particularly between residues 14 to 23, more particularly between amino acid residues 14 and 20, comprising three distinct recognition and binding sites which residues are predominantly involved in the binding of the β-amyloid protein and located at position 16, 17, and at position 19 and 20, and at position 14, respectively.

In a specific embodiment the mixture of the present invention comprises, in addition to the compound of the invention, an antibody, particularly a bifunctional antibody, but especially a monoclonal antibody, particularly a bifunctional monoclonal antibody, including any functionally equivalent antibody or functional parts thereof, which antibody has the characteristic properties of an antibody produced by a hybridoma cell line selected from the group consisting of FP 12H3, FP 12H3-G2, and FP 12H3-G2 deposited on Dec. 1, 2005 and Dec. 9, 2005, respectively, as DSM ACC2752, DSM ACC 2750 and DSM ACC2751, respectively, ET 7E3 deposited on Dec. 8, 2005 as DSM ACC2755, and EJ 7H3 deposited on Dec. 8, 2005 as DSM ACC2756.

More particularly, the invention relates to an antibody including any functionally equivalent antibody or functional parts thereof produced by a hybridoma cell line selected from the group consisting of FP 12H3, FP 12H3-G2, and FP 12H3-G2 deposited on Dec. 1, 2005 and Dec. 9, 2005, respectively, as DSM ACC2752, DSM ACC 2750 and DSM ACC2751, respectively, ET 7E3 deposited on Dec. 8, 2005 as DSM ACC2755, and EJ 7H3 deposited on Dec. 8, 2005 as DSM ACC2756.

The above antibodies are described in the published international application WO 2007/068412, which is incorporated herein by reference.

In a further aspect, the antibody which is comprised in the mixture according to the invention is a chimeric antibody or a fragment thereof, or a humanized antibody or a fragment thereof. These and further antibodies that can be suitably used within the mixtures according to the present invention are described, for example, in international application PCT/US2007/073504 filed Jul. 13, 2007.

If the antibody is a humanized antibody, it preferably exhibits a light chain and a heavy chain as depicted in SEQ ID No. 2 and SEQ ID No. 4 of International Application No. PCT/US2007/073504 or exhibits a light chain variable region and a heavy chain variable region as depicted in SEQ ID No. 1 and SEQ ID No. 3 of International Application No. PCT/US2007/073504. These sequences are also shown in the attached sequence listing.

In still another aspect of the invention, a mixture is provided which comprises, in addition to the compound according to the invention and as described herein before, a peptide fragment from the N-terminal part of the Aβ peptide, particularly an Aβ peptide fragment consisting of a single or repetitive stretch of between 13 and 15 contiguous amino acid residues from the N-terminal part of the Aβ peptide, but particularly an Aβ peptide fragment consisting of amino acid residues selected from the group consisting of residues 1-15, 1-14, and 1-13 from the N-terminal part of the Aβ peptide, more particularly of residue 1-15, including functionally equivalent fragments thereof, but especially a Aβ peptide fragment as mentioned herein before attached to, or incorporated or reconstituted in a carrier particle/adjuvant such as, for example, a liposome. The peptide fragment can be comprised in a vaccine composition. In particular, the peptide antigen is modified by a lipophilic or hydrophobic moiety, that facilitates insertion into the lipid bilayer of the liposome carrier/immune adjuvant, particularly by a lipophilic or hydrophobic moiety which functions as an anchor for the peptide in the liposome bilayer and has a dimension that leads to the peptide being positioned and stabilized in close proximity to the liposome surface.

In a further embodiment of the invention, the lipophilic or hydrophobic moiety is a fatty acid, a triglyceride or a phospholipid, but especially a fatty acid, a triglyceride or a phospholipid. In particular, the hydrophobic moiety is palmitic acid and the liposome preparation may in addition contain an adjuvant such as, for example, lipid A, alum, calcium phosphate, interleukin 1, and/or microcapsules of polysaccharides and proteins, but particularly a detoxified lipid A, such as monophosphoryl or diphosphoryl lipid A, or alum.

These and further compositions that can be suitably used in the mixtures of the present invention are described, for example, in the published international application WO 2007/068411.

Diagnosis of an amyloid-associated disease or condition or of a predisposition to an amyloid-associated disease or condition in a patient may be achieved by detecting the specific binding of a compound according to the invention to the amyloid protein in a sample or in situ, which includes bringing the sample or a specific body part or body area suspected to contain the amyloid antigen into contact with a compound of the invention which binds the amyloid protein, allowing the compound of the invention to bind to the amyloid protein to form a compound/protein complex, detecting the formation of the compound/protein complex and correlating the presence or absence of the compound/protein complex with the presence or absence of amyloid protein in the sample or specific body part or area, optionally comparing the amount of said compound/protein complex to a normal control value, wherein an increase in the amount of said aggregate compared to a normal control value may indicate that said patient is suffering from or is at risk of developing an amyloid-associated disease or condition. Monitoring minimal residual disease in a patient following treatment with a compound or a mixture according to the invention may be achieved by detecting the specific binding of a compound according to the invention to the amyloid protein in a sample or in situ, which includes bringing the sample or a specific body part or body area suspected to contain the amyloid antigen into contact with a compound of the invention which binds the amyloid protein, allowing the compound to bind to the amyloid protein to form an compound/protein complex, detecting the formation of the compound/protein complex and correlating the presence or absence of the compound/protein complex with the presence or absence of amyloid protein in the sample or specific body part or area, optionally comparing the amount of said compound/protein complex to a normal control value, wherein an increase in the amount of said aggregate compared to a normal control value may indicate that said patient may still suffer from a minimal residual disease.

Predicting responsiveness of a patient to a treatment with a compound or composition or a mixture according to the invention may be achieved by detecting the specific binding of a compound according to the invention to the amyloid protein in a sample or in situ, which includes bringing the sample or a specific body part or body area suspected to contain the amyloid protein into contact with a compound of the invention which binds the amyloid protein, allowing the compound to bind to the amyloid protein to form an compound/protein complex, detecting the formation of the compound/protein complex and correlating the presence or absence of the compound/protein complex with the presence or absence of amyloid protein in the sample or specific body part or area, optionally comparing the amount of said compound/protein complex before and after onset of the treatment, wherein an decrease in the amount of said aggregate may indicate that said patient has a high potential of being responsive to the treatment.

Biological samples that may be used in the diagnosis of an amyloid-associated disease or condition for diagnosing a predisposition to an amyloid-associated disease or condition or for monitoring minimal residual disease in a patient or for predicting responsiveness of a patient to a treatment with a compound or a composition or a mixture according to the invention and as described herein before are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the amyloid protein in a sample any immunoassay known to those of ordinary skill in the art (see Harlow and Lane, Antibodies: A Laboratory Manual (Cold Spring Harbor Laboratory, New York, 1988, 555 to 612) may be used such as, for example, assays which utilize indirect detection methods using secondary reagents for detection, ELISA's and immunoprecipitation and agglutination assays. A detailed description of these assays is, for example, given in WO96/13590 to Maertens and Stuyver, Zrein et al. (1998) and WO96/29605.

For in situ diagnosis, the compound or composition or mixture according to the invention and as described herein before may be administered to the organism to be diagnosed by methods known in the art such as, for example, intravenous, intranasal, intraperitoneal, intracerebral, intraarterial injection such that a specific binding between the compound according to the invention and the amyloid antigen may occur. The compound/protein complex may be detected through a label attached to the compound.

The immunoassays used in diagnostic applications or in applications for diagnosing a predisposition to an amyloid-associated disease or condition or for monitoring minimal residual disease in a patient or for predicting responsiveness of a patient to a treatment with a compound or composition or a mixture according to the invention and as described herein before, typically rely on labelled antigens, antibodies, or secondary reagents for detection. These proteins or reagents can be labelled with compounds generally known to those skilled in the art including enzymes, radioisotopes, and fluorescent, luminescent and chromogenic substances including colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the compound of the invention may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antibody. For example, the antibody may be conjugated to biotin and the antibody-biotin conjugate detected using labelled avidin or streptavidin. Similarly, the antibody may be conjugated to a hapten and the antibody-hapten conjugate detected using labelled anti-hapten antibody.

Those of ordinary skill in the art will know of these and other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein the antibody is labelled indirectly by reactivity with a second antibody that has been labelled with a detectable label. The second antibody is preferably one that binds to antibodies of the animal from which the monoclonal antibody is derived. In other words, if the monoclonal antibody is a mouse antibody, then the labelled, second antibody is an anti-mouse antibody. For the monoclonal antibody to be used in the assay described below, this label is preferably an antibody-coated bead, particularly a magnetic bead. For the polyclonal antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the amyloid antigen is determined using a pair of antibodies, each specific for amyloid antigen. One of said pairs of antibodies is referred to herein as a "detector antibody" and the other of said pair of antibodies is referred to herein as a "capture antibody". The monoclonal antibody can be used as either a capture antibody or a detector antibody. The monoclonal antibody can also be used as both capture and detector antibody, together in a single assay. One embodiment of the present invention thus uses the double antibody sandwich method for detecting amyloid antigen in a sample of biological fluid. In this method, the analyte (amyloid antigen) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those skilled in the art. More recently, a number of porous material such as nylon, nitrocellulose, cellulose acetate, glass fibers and other porous polymers have been employed as solid supports.

The plaque burden in the tissue and/or body fluid (such as the retinal ganglion cell layer of an animal, particularly a mammal, but especially a human suffering from an ocular disease associated with pathological abnormalities/changes in the tissues of the visual system, particularly associated with amyloid-beta-related pathological abnormalities/changes in the tissues of the visual system) can be calculated by methods known in the art such as that disclosed in Ding, J.-D. et al., "Targeting age-related macular degeneration with Alzheimer's disease based immunotherapies: Anti-amyloid-b antibody attenuates pathologies in an age-related macular degeneration mouse model", Vision Research (2007), doi:10.1016/j.visres.2007.07.025.

A compound according to the present invention can also be incorporated into a test kit for detecting an amyloid protein. The test kit typically comprises a container holding one or more compounds according to the present invention and instructions for using the compound for the purpose of binding to an amyloid protein to form a compound/protein complex and detecting the formation of the compound/protein complex such that presence or absence of the compound/protein complex correlates with the presence or absence of the amyloid protein.

The term "test kit" refers in general to any diagnostic kit known in the art. More specifically, the latter term refers to a diagnostic kit as described in Zrein et al. (1998).

EXAMPLES

The present invention is illustrated by the following non-limiting examples.

Preparation of 2a: 5-p-Tolyl-N-((5-p-tolyl-1H-pyrazol-3-yl)methyl)-1H-pyrazol-3-amine dihydrochloride

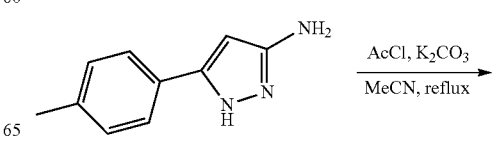

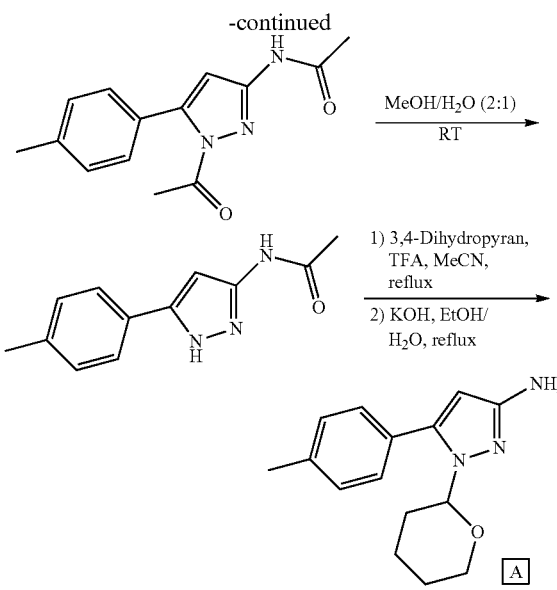

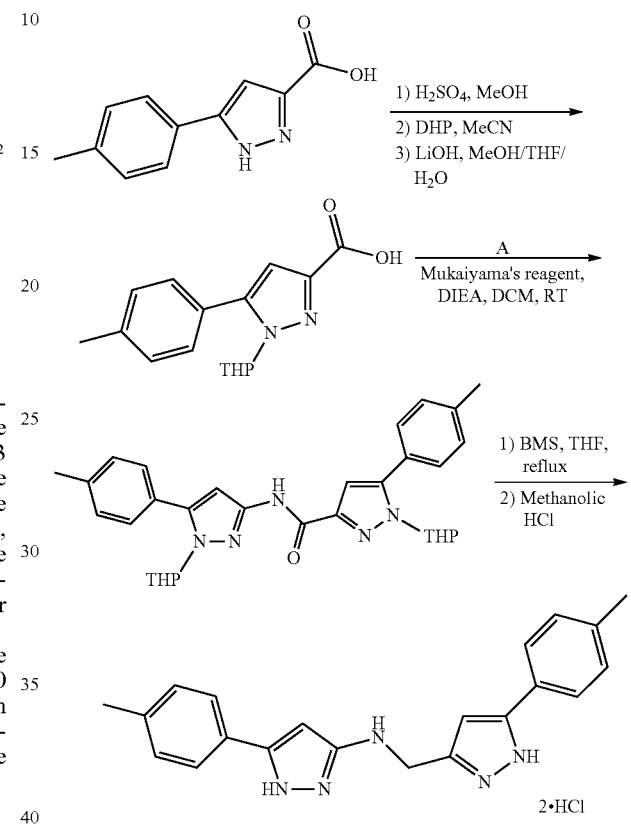

Acetyl chloride (6.16 mL, 86.60 mmol) was added dropwise to a suspension of 5-amino-3-(4-methylphenyl)pyrazole (5 g, 28.86 mmol) and potassium carbonate (14 g, 101.03 mmol) in anhydrous MeCN (100 mL). The reaction mixture was refluxed for 16 hrs. The solvent was evaporated and the residue was resuspended in CHCl$_3$, and washed with 1N HCl, sat. aq. NaHCO$_3$, H$_2$O and brine and dried over Na$_2$SO$_4$. The solvent was evaporated and the crude N-(1-acetyl-5-p-tolyl-1H-pyrazol-3-yl)acetamide was used without any further purification in the next step.

Crude N-(1-acetyl-5-p-tolyl-1H-pyrazol-3-yl)acetamide was dissolved in a mixture of MeOH/THF/H$_2$O (2:2:1, 150 mL) with 2 drops of 33% ammonia solution. The reaction mixture was stirred for 16 hrs, then the solvents were evaporated and the crude N-(5-p-tolyl-1H-pyrazol-3-yl)acetamide was used without any further purification in the next step.

MS (ESI): m/z: 216.29 [MH$^+$].

A mixture of crude N-(5-p-tolyl-1H-pyrazol-3-yl)acetamide (28.86 mmol), 3,4-dihydro-2H-pyran (6.7 mL, 72.15 mmol) and trifluoroacetic acid (43 µL, 0.58 mmol) in anhydrous MeCN (60 mL) was refluxed for 16 hrs. The solvent was evaporated and the residue was resuspended in CH$_2$Cl$_2$ (50 mL), washed with H$_2$O and brine and dried over Na$_2$SO$_4$. The solvent was evaporated and the crude N-(5-tolyl-1-(tetrahydro-2H-pyran-2-yl)-1H-pyrazol-3-yl)acetamide was used without any further purification in the next step.

MS (ESI): m/z: 300.33 [MH$^+$].

Crude N-(5-methyl-1-(tetrahydro-2H-pyran-2-yl)-1H-pyrazol-3-yl)acetamide (28.86 mmol) was dissolved in EtOH/H$_2$O (2:3, 100 mL) together with potassium hydroxide (11 g, 202 mmol) and was refluxed for 16 hrs. The reaction mixture was concentrated and then extracted with CHCl$_3$. The combined organic layers were washed with brine and dried over Na$_2$SO$_4$. Solvent evaporation and purification by silica gel column chromatography (PE-EtOAc, 7:3 to 3:7) gave 5-tolyl-1-(tetrahydro-2H-pyran-2-yl)-1H-pyrazol-3-amine (2.99 g regioisomer A and 4.39 g regioisomer B, 99% over 4 steps).

Regioisomer A:
$^1$H-NMR (400 MHz, CDCl$_3$): δ (ppm)=7.63 (d, J=7.7 Hz, 2H), 7.16 (d, J=8.6 Hz, 2H), 5.81 (s, 1H), 5.38 (dd, J=8.9 Hz, J=2.6 Hz, 1H), 4.01 (bm, 3H), 3.68 (dt, J=11.5 Hz, J=2.6 Hz, 1H), 2.38 (m, 1H), 2.35 (s, 3H), 2.03-2.14 (m, 2H), 1.62-1.71 (m, 3H)

MS (ESI): m/z: 258.37 [MH$^+$]. .

Regioisomer B:
$^1$H-NMR (400 MHz, CDCl$_3$): δ (ppm)=7.36 (d, J=8.0 Hz, 2H), 7.24 (d, J=8.0 Hz, 2H), 5.69 (s, 1H), 5.03 (dd, J=10.2 Hz, J=2.5 Hz, 1H), 4.11 (m, 1H), 3.69 (bs, 2H), 3.54 (dt, J=12.0 Hz, J=2.5 Hz, 1H), 2.46 (m, 1H), 2.41 (s, 3H), 1.70-1.79 (m, 2H), 1.50-1.59 (m, 3H).

MS (ESI): m/z: 258.37 [MH$^+$].

5-p-Tolyl-1H-pyrazole-3-carboxylic acid (250 mg, 1.24 mmol) and sulfuric acid (120 µL, 1.48 mmol) in methanol (5 mL) were heated to reflux for 16 hrs. The solvent was evaporated and the residue was resuspended in CH$_2$Cl$_2$. The residue was filtrated and the filtrate was washed with water and brine and dried over Na$_2$SO$_4$. Solvent was evaporated and the white solid was combined with the precipitate collected previously. Methyl 5-p-tolyl-1H-pyrazole-3-carboxylate (224 mg, 84%) was obtained as a white solid. $^1$H-NMR (400 MHz, CDCl$_3$): δ (ppm)=7.56 (d, J=7.6 Hz, 2H), 7.22 (d, J=8.0 Hz, 2H), 7.02 (s, 1H), 3.91 (s, 3H), 2.36 (s, 3H).

$^{13}$C-NMR (100 MHz, CDCl$_3$): δ (ppm)=129.61, 125.45, 105.03, 52.02, 21.19.

A mixture of methyl 5-p-tolyl-1H-pyrazole-3-carboxylate (224 mg, 1.03 mmol), 3,4-dihydro-2H-pyran (190 µL, 2.07 mmol) and trifluoroacetic acid (2 µL, 0.02 mmol) in anhydrous MeCN (3 mL) was refluxed for 2 hrs. The solvent was evaporated. The residue was resuspended in CH$_2$Cl$_2$ (50 mL) and was washed with H$_2$O and brine. After drying with Na$_2$SO$_4$, solvent evaporation and silica gel column chromatography (PE-EtOAc, 6:4) methyl 1-(tetrahydro-2H-pyran-2-yl)-5-p-tolyl-1H-pyrazole-3-carboxylate (363 mg, 68%) was obtained.

$^1$H-NMR (400 MHz, CDCl$_3$): δ (ppm)=7.40 (d, J=8.0 Hz, 2H), 7.27 (d, J=8.0 Hz, 2H), 6.82 (s, 1H), 5.25 (d, J=10.0 Hz, 1H), 4.11 (m, 1H), 3.92 (s, 3H), 3.57 (t, J=10.8 Hz, 1H), 2.61 (m, 1H), 2.41 (s, 3H), 2.03 (m, 1H), 1.82 (d, J=8.06 Hz, 1H), 1.58-1.52 (m, 3H).

Methyl 1-(tetrahydro-2H-pyran-2-yl)-5-p-tolyl-1H-pyrazole-3-carboxylate (363 mg, 0.70 mmol) was dissolved in a mixture of MeOH/THF/H$_2$O (1:2:1, 4 mL). Lithium hydroxide was added and the reaction mixture was stirred for 16 hrs. The reaction mixture was diluted with water and washed with DCM. The aqueous phase was evaporated. 1-(Tetrahydro-2H-pyran-2-yl)-5-p-tolyl-1H-pyrazole-3-carboxylic acid (205 mg, quantitative) was obtained as a white solid which was used without further purification in the next step.

$^1$H-NMR (400 MHz, CDCl$_3$): δ (ppm)=7.13 (d, J=6.8 Hz, 2H), 7.04 (d, J=6.8 Hz, 2H), 6.60 (s, 1H), 4.92 (d, J=9.6 Hz, 1H), 3.89 (d, J=8.4 Hz, 1H), 3.35 (t, J=10.8 Hz, 1H), 2.40 (m, 1-H), 2.31 (s, 3H), 1.75 (m, 1H), 1.54 (m, 2H), 1.25 (m, 2H).

5-Tolyl-1-(tetrahydro-2H-pyran-2-yl)-1H-pyrazol-3-amine (compound A, 81 mg, 0.31 mmol) was added to a solution of 1-(tetrahydro-2H-pyran-2-yl)-5-p-tolyl-1H-pyrazole-3-carboxylic acid (100 mg, 0.34 mmol), 2-chloro-1-methylpyridinium iodide (122 mg, 0.47 mmol) and N,N'-diisopropylethylamine (163 μL, 0.94 mmol) in DCM (10 mL). The reaction mixture was stirred at RT for 16 hrs. The reaction mixture was diluted with water and extracted with DCM. The organic layer was washed with brine, dried over Na$_2$SO$_4$ and concentrated. The crude product was purified by silica gel column chromatography (PE-EtOAc, 9:1) and gave 1-(tetrahydro-2H-pyran-2-yl)-N-(1-(tetrahydro-2H-pyran-2-yl)-5-p-tolyl-1H-pyrazol-3-yl)-5-p-tolyl-1H-pyrazole-3-carboxamide (70 mg, 43%).

$^1$H-NMR (400 MHz, CDCl$_3$): δ (ppm)=9.37 (s, 0.5H), 9.34 (s, 0.5H), 7.43 (m, 4H), 7.28 (m, 4H), 6.95 (s, 0.5H), 6.94 (s, 0.5H), 6.90 (s, 1H), 5.24 (m, 2H), 4.15 (m, 2H), 3.60 (m, 2H), 2.45 (m, 2H), 2.42 (s, 6H), 1.80 (m, 2H), 1.56 (m, 4H), 1.25 (m, 4H).

1-(Tetrahydro-2H-pyran-2-yl)-N-(1-(tetrahydro-2H-pyran-2-yl)-5-p-tolyl-1H-pyrazol-3-yl)-5-p-tolyl-1H-pyrazole-3-carboxamide (142 mg, 0.27 mmol) was suspended in anhydrous THF (10 mL) and borane dimethylsulfide complex (177 μL, 1.86 mmol) was added dropwise. The reaction mixture was stirred under reflux for 16 hrs. The reaction mixture was then cooled down to 0° C. and MeOH (500 μL) was added. The mixture was then stirred for 10 min. Concentrated hydrochloric acid (12 N) was added, until a pH<2 was obtained, and the resulting mixture was stirred under reflux for 16 hrs. The mixture was cooled to room temperature and the precipitate was filtered and added into an aqueous solution of sodium hydroxide (1M). The aqueous phase was extracted with DCM (3×10 mL) after drying the organic layers with Na$_2$SO$_4$, the solvent was evaporated. The residue was purified by chromatography on silica gel column (eluent: EtOAc); 5-p-tolyl-N-((5-p-tolyl-1H-pyrazol-3-yl)methyl)-1H-pyrazol-3-amine was obtained as a white solid.

5-p-Tolyl-N-((5-p-tolyl-1H-pyrazol-3-yl)methyl)-1H-pyrazol-3-amine (27 mg, 0.078 mmol) was recrystallized in methanolic HCl (3 N, 1 mL). The solid was filtered, washed with Et$_2$O and dried in vacuo; white solid. Mp=132° C.

$^1$H NMR (400 MHz, DMSO-d$_6$): δ=7.73 (d, J=8.0 Hz, 2H), 7.62 (d, J=8.0 Hz, 2H), 7.33 (d, J=8.0 Hz, 2H), 7.22 (d, J=8.0 Hz, 2H), 6.63 (s, 1H), 6.30 (s, 1H), 4.42 (s, 2H), 2.36 (s, 3H), 2.31 (s, 3H).

Preparation of 2c: N$^5$-Propyl-N$^2$-((6-((6-(propylamino)pyridin-3-yl)methylamino)pyridin-3-yl)methyl)pyridine-2,5-diamine

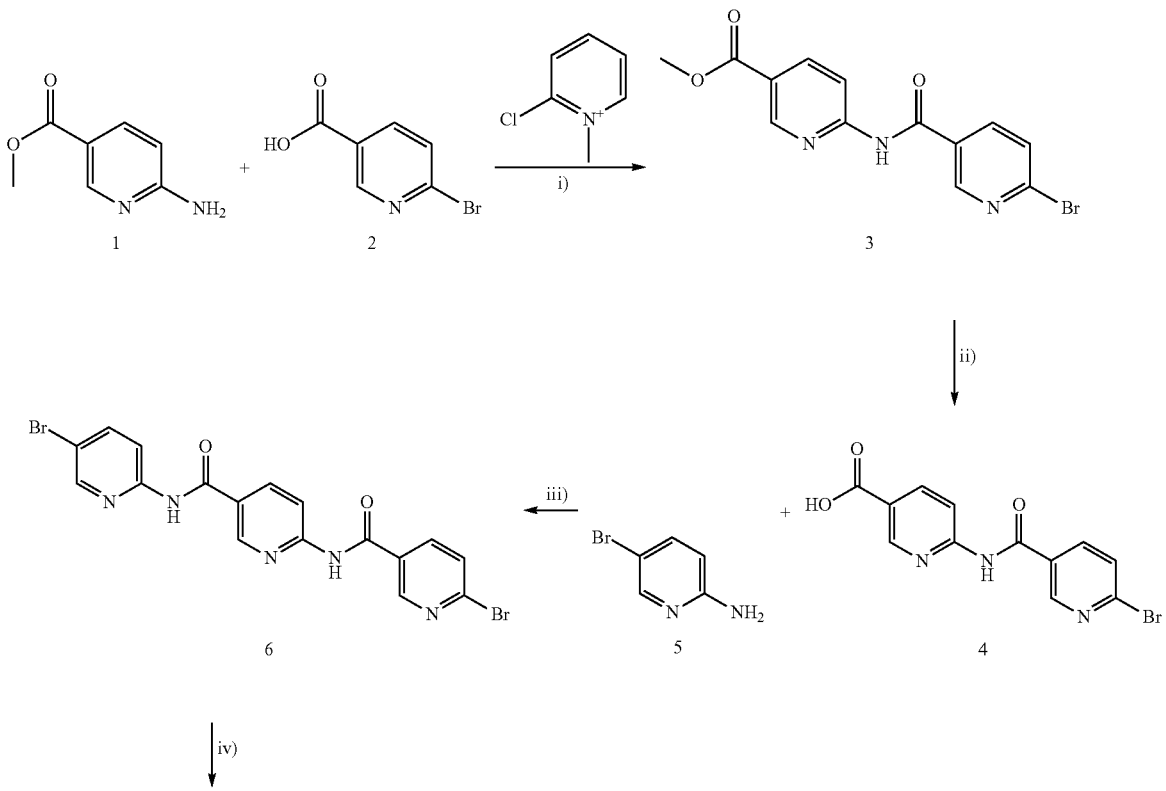

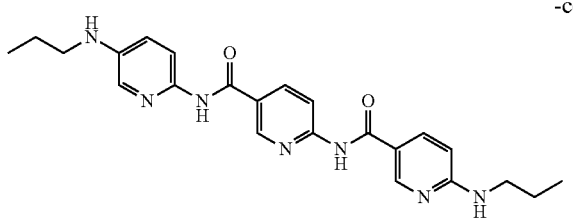 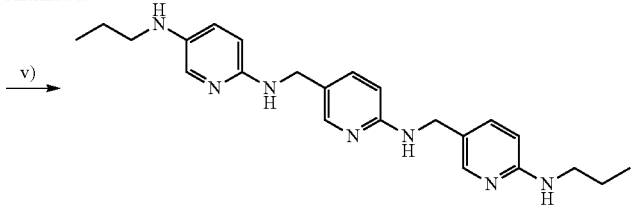

Reagents: i) 2-chloro-1-methylpyridinium iodide ii) KOH/EtOH/H₂O iii) 5/2-chloro-1-methylpyridinium iodide iv) n-propyl amine/reflux, 16 h v) BMS/THF/32 h 2-Chloro-1-methylpyridinium iodide (2.99 g, 10 mmol) and DIPEA (3 mL) were added to a mixture of methyl 6-aminonicotinate 1 (760 mg, 5 mmol) and 6-bromonicotinic acid 2 (1 g, 5 mmol) in THF (150 mL). The reaction mixture was stirred at rt (=room temperature) for 4 days. At the conclusion of the reaction, the reaction mixture was concentrated to ⅓ of its volume and the precipitated product was filtered off. The filtrate was concentrated, diluted with chloroform (100 ml), washed with water and brine and dried over Na₂SO₄. Evaporation of the solvent gave a crude yellow product, which crystallized in EtOAc to give methyl 6-(6-bromonicotinamido)nicotinate 3 as a white solid (1 g, 65.4%). Mp. 234-235° C.

¹H-NMR (400 MHz, CDCl₃): δ=11.5 (s, 1H), 8.96 (d, J=2.0 Hz, 1H), 8.93 (s, 1H), 8.36 (dd, J=2.0 Hz, J=8.0 Hz, 1H), 8.33 (d, J=12 Hz, 1H), 8.28 (dd, J=2.4 Hz, J=8.0 Hz, 1H), 7.83 (d, J=8.4 Hz, 1H), 3.88 (s, 3H).

MS (ESI): m/z=338 (M+2H)

KOH pellets (5 g) were added to a suspension of methyl 6-(6-bromonicotinamido) nicotinate 3 (5 g, 14.8 mmol) in methanol and water (150/50 ml). The reaction mixture was stirred for 4 hours. Then the solvent was evaporated and the pH was adjusted to below 2. The white solid was filtered off and washed with cold water and dried under vacuum to give 6-(6-bromonicotinamido)nicotinic acid 4 (1.8 g, 37%). Mp. 270-272° C.

¹H-NMR (400 MHz, DMSO-d₆): δ=11.52 (s, 1H), 8.95 (s, 1H), 8.91 (s, 1H), 8.29 (m, 3H), 7.83 (d, J=8.0 Hz, 1H). MS (ESI): m/z=322 (M⁺).

2-chloro-1-methylpyridinium iodide (2.37 g, 18.6 mmol) was added to a suspension of 6-(6-bromonicotinamido)nicotinic acid 4 (2 g, 6.21 mmol) and 2-amino-5-bromopyridine 5 (1.07 g, 6.21 mmol) in THF (100 ml), followed by DIPEA (2.4 g, 18.6 mmol). The reaction mixture was stirred for 4 days at RT. The suspension was filtered off and washed with water (25 ml). The filtrate was concentrated, diluted in chloroform, washed with water and brine, and then dried over Na₂SO₄. The product precipitated during evaporation and was dried under vacuum to give 6-bromo-N-(5-(5-bromopyridin-2-ylcarbamoyl)pyridin-2-yl)nicotinamide 6 as a yellow solid (400 mg, 14%). Mp. 245-247° C.

¹H-NMR (400 MHz, DMSO-d₆): δ=11.1 (br s, 1H), 10.8 (br s, 1H), 9.0 (s, 1H), 8.7 (s, 1H), 8.53 (s, 1H), 8.41 (d, J=8.4 Hz, 1H), 8.30 (d, J=8.8 Hz, 1H), 8.21 (d, J=8.4 Hz, 1H), 8.1 (d, J=9.2 Hz, 1H), 8.01 (d, J=8.8 Hz, 1H), 7.32 (br s, 1H), 6.51 (d, J=8.8 Hz), 3.2 (d, J=6.0 Hz, 4H), 1.57 (q, J=7.2 Hz, 4H), 0.92 (t, J=7.2 Hz, 6H)

MS (ESI): m/z=478 (M+H).

6-Bromo-N-(5-(5-bromopyridin-2-ylcarbamoyl)pyridin-2-yl)nicotinamide 6 (350 mg, 0.73 mmol) was dissolved in neat n-propylamine. The reaction mixture was heated for 3 days at reflux temperature. Then the solvent was evaporated to give a crude product, which was crystallized in EtOAc to give 6-(propylamino)-N-(5-(5-(propylamino)pyridin-2-ylcarbamoyl)pyridin-2-yl)nicotinamide 7 (122 mg, 38% yield) as a white solid. Mp. 249-250° C.

¹H-NMR (400 MHz, D₂O+ DMSO-d₆): δ=8.95 (d, J=2.0 Hz, 1H), 8.68 (d, J=2.0 Hz, 1H), 8.50 (d, J=2.0 Hz, 1H), 8.36 (dd, J₁=2.2, J₂=8.8 Hz, 1H), 8.24 (d, J=8.8 Hz 1H), 8.15 (d, J=8.8 Hz, 1H), 8.06 (dd, J₁=2.2, J₂=9.2 Hz, 1H), 7.96 (dd, J₁=1.6, J₂=8.8 Hz 1H), 6.51 (d, J=8.8 Hz, 1H), 3.25 (t, J=4.0 Hz, 4H), 1.54 (m, 4H), 0.90 (t, J=7.3 Hz, 6H).

MS (ESI): m/z=457 (M+Na).

BMS (129 μL 1.73 mmol) was added to a solution of 6-(propylamino)-N-(5-(5-(propylamino)pyridin-2-ylcarbamoyl)pyridin-2-yl)nicotinamide 7 (75 mg, 0.173 mmol) in THF (15 ml). The reaction mixture was refluxed over night and cooled, then MeOH was added followed by conc. HCl. The mixture was refluxed again for another 16 hrs. Then the reaction mixture was concentrated, the residue was diluted in water (5 ml) and the pH was adjusted to 14 using NaOH solution. The aqueous layer was extracted with chloroform (50 ml×3) and the combined organic layers were washed with water and brine and then dried over Na₂SO₄. Evaporation of the solvent yielded a residue that was purified on silica gel (2:98, MeOH:EtOAc) to give a brown sticky material (5 mg, 7%). Then it was treated with HCl/MeOH to give N⁵-propyl-N²-((6-((6-(propylamino)pyridin-3-yl)methylamino)pyridin-3-yl)methyl)pyridine-2,5-diamine hydrochloride salt 8 (5 mg) as a gummy material.

¹H-NMR (400 MHz, D₂O+ DMSO-d₆): δ=8.48 (s, 3H), 7.88 (d, J=8.8 Hz 3H), 6.33 (d, J=8.8 Hz, 3H), 6.08 (brs, 2H) 5.04 (brs, 2H), 3.42 (m, 2H), 3.27 (m, 2H), 1.63 (m, 4H), 1.03 (m, 6H)

MS (ESI): m/z=408 (M+3H)

Preparation of 2h: N-Benzyl-5-((5-p-tolylthiazol-2-ylamino)methyl)thiazol-2-amine dihydrochloride

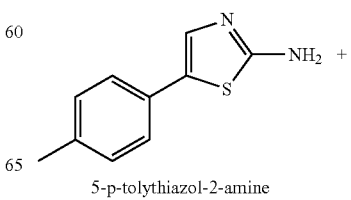

5-p-tolythiazol-2-amine

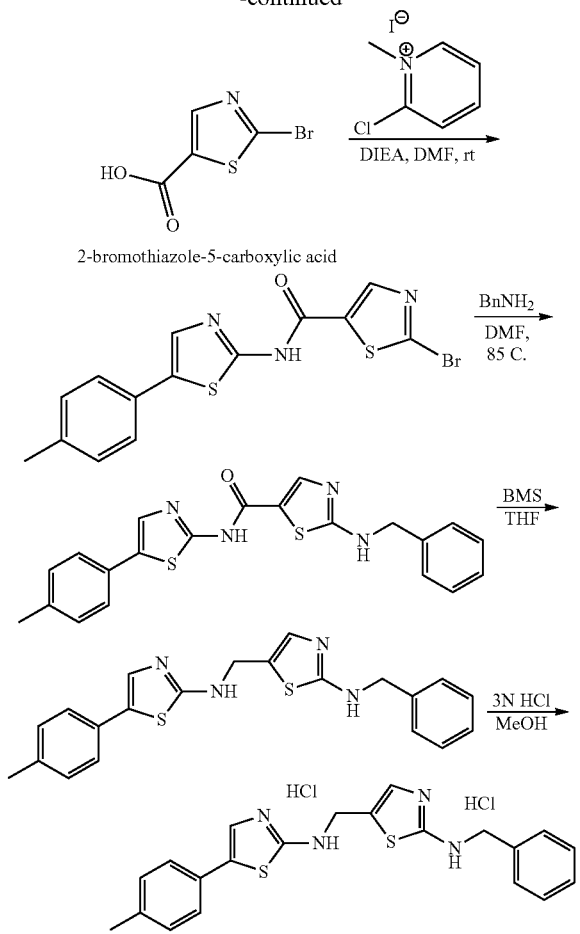

2-bromothiazole-5-carboxylic acid

2-Chloro-1-methylpyridinium iodide (0.55 g, 2.2 mmol), DIEA (0.37 g, 2.9 mmol) and 5-p-tolylthiazol-2-amine (0.27 g, 1.44 mmol) were added to a suspension of 2-bromothiazole-5-carboxylic acid (0.30 g, 1.44 mmol) in DMF (5 mL). The resulting solution was stirred at RT till completion of the reaction. The mixture was then diluted with AcOEt, washed with water, dried with $Na_2SO_4$ and concentrated. The crude product was purified by column (30% AcOEt/PE), yielding 2-bromo-N-(5-p-tolylthiazol-2-yl)thiazole-5-carboxamide (250 mg, 46%) as a solid.

$^1$H-NMR (400 MHz, $CDCl_3$): δ (ppm): 8.19 (s, 1H), 7.6 (d, J=8 Hz, 2H), 7.15 (d, J=8 Hz, 2H), 7.04 (s, 1H), 2.31 (s, 3H).

$^{13}$C-NMR (100 MHz, $CDCl_3$): δ (ppm): 157.89, 149.44, 147.77, 144.33, 143.16, 141.99, 138.10, 137.38, 131.07, 129.32, 125.87, 107.34, 20.93.

MS (ESI): m/z (%): 379.87 [MH$^+$].

Benzylamine (0.143 mL, 1.32 mmol) was added to a solution of 2-bromo-N-(5-p-tolylthiazol-2-yl)thiazole-5-carboxamide (250 mg, 0.66 mmol) in DMF (4 mL). The reaction mixture was stirred at reflux for 2 hrs. Then it was diluted with AcOEt and washed with water, dried with $Na_2SO_4$ and concentrated. The crude product was purified by precipitation (AcOEt/PE), yielding 2-(benzylamino)-N-(5-p-tolylthiazol-2-yl)thiazole-5-carboxamide (190 mg, 71%) as a solid.

$^1$H-NMR (400 MHz, $CDCl_3$): δ (ppm): 8.85 (bs, 1H), 8.25 (s, 1H), 7.80 (d, J=8 Hz, 2H), 7.46 (s, 1H), 7.35 (m, 3H), 7.28, (m, 2H), 7.23 (d, J=8 Hz, 2H), 4.53 (s, 1H), 2.33 (s, 3H).

$^{13}$C-NMR (100 MHz, $CDCl_3$): δ (ppm): 172.44, 158.89, 148.82, 145.74, 145.06, 137.99, 136.75, 131.58, 128.97, 128.15, 127.19, 126.92, 125.46, 118.98, 106.83, 47.44, 20.49.

MS (ESI): m/z (%): 407.36 [MH$^+$].

BMS (0.2 mL, 2.1 mmol) was added to a solution of 2-(benzylamino)-N-(5-p-tolylthiazol-2-yl)thiazole-5-carboxamide (170 mg, 0.42 mmol) in THF (6 mL) at RT. The resulting solution was stirred at reflux overnight. The reaction was then quenched with MeOH (2 mL) and 1N HCl was added until the pH reached 2. After stirring the reaction mixture at reflux temperature for 12 hrs, the organic solvents were evaporated and the aqueous solution was neutralized with 1N NaOH, extracted with $CHCl_3$, dried with $Na_2SO_4$ and concentrated. The crude product was purified by column (AcOEt), yielding N-benzyl-5-((5-p-tolylthiazol-2-ylamino)methyl)thiazol-2-amine (30 mg, 18%).

$^1$H-NMR (400 MHz, $CDCl_3$): δ (ppm): 7.59 (d, J=8 Hz, 2H), 7.23 (m, 5H), 7.11 (d; J=8 Hz, 2H), 6.93 (s, 1H), 6.58 (s, 1H), 4.40 (s, 2H), 4.32 (s, 2H), 3.41 (bs, 2H), 2.29 (s, 3H).

$^{13}$C-NMR (100 MHz, $CDCl_3$): δ (ppm): 197.01, 170.75, 151.05, 137.39, 137.26, 137.03, 131.82, 129.07, 128.48, 127.48, 127.41, 125.75, 121.99, 100.46, 49.30, 41.95, 20.99.

MS (ESI): m/z: 393.28 [MH$^+$].

N-Benzyl-5-((5-p-tolylthiazol-2-ylamino)methyl)thiazol-2-amine (20 mg, 0.05 mmol) was dissolved in methanolic HCl (3 N, 1 mL) and $CHCl_3$/AcOEt was added. The precipitated solid was filtered by decantation and dried in vacuo, yielding N-benzyl-5-((5-p-tolylthiazol-2-ylamino)methyl)thiazol-2-amine dihydrochloride as a white solid (11 mg, 10%). Mp. 105-106° C.

Preparation of 2j: N-Benzyl-5-((4-p-tolylthiazol-2-ylamino)methyl)thiazol-2-amine dihydrochloride

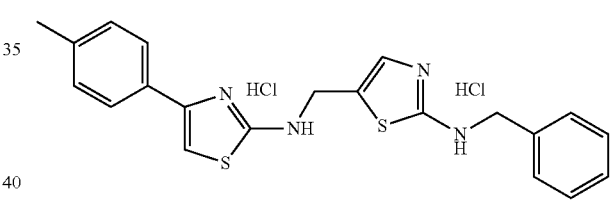

Compound 2j was prepared as described for 2 h starting from 4-p-tolylthiazol-2-amine and 2-bromothiazole-5-carboxylic acid: (3.5 mg, 59%). Mp. 106-108° C.

$^1$H-NMR (400 MHz, $CDCl_3$): δ (ppm): 7.61 (d, J=8 Hz, 2H), 7.28 (m, 5H), 7.13 (d, J=8 Hz, 2H), 6.95 (s, 1H), 6.60 (s, 1H), 4.42 (s, 2H), 4.34 (s, 2H), 3.01 (bs, 2H), 2.31 (s, 3H).

$^{13}$C-NMR (100 MHz, $CDCl_3$): δ (ppm): 170.68, 168.62, 151.11, 138.15, 137.48, 137.23, 131.86, 129.12, 128.55, 127.56, 127.74, 125.80, 122.076, 100.53, 49.33, 40.07, 21.07.

MS (ESI): m/z (%): 393.29 [MH$^+$].

Preparation of 2k: N-Benzyl-5-((5-(4-fluorophenyl)-1H-pyrazol-3-ylamino)methyl)thiazol-2-amine dihydrochloride

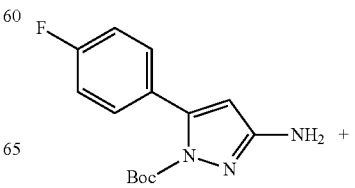

-continued

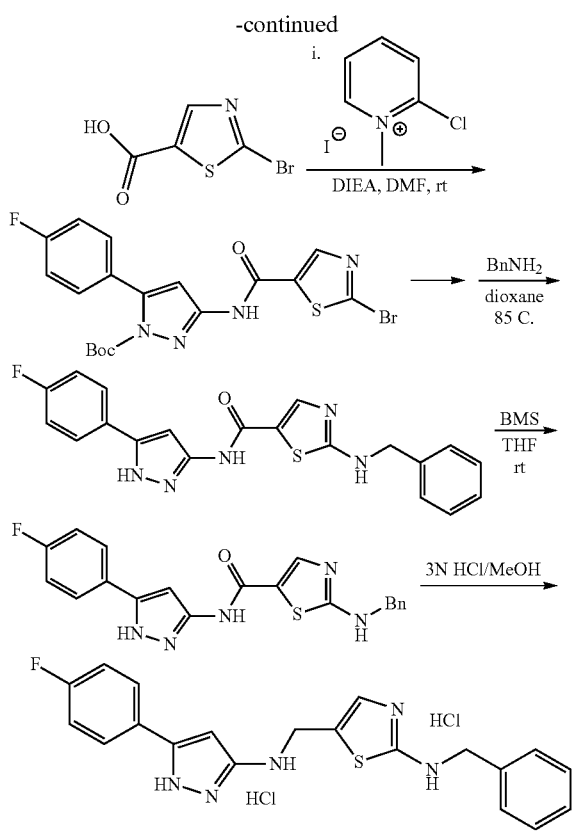

2-Chloro-1-methylpyridinium iodide (0.84 g, 3.3 mmol), DIPEA (0.78 mL, 4.4 mmol) and tert-butyl 3-amino-5-(4-fluorophenyl)-1H-pyrazole-1-carboxylate (0.5 g, 2.2 mmol) were added to a solution of 2-bromothiazole-5-carboxylic acid (0.45 g, 2.2 mmol) in DMF (6 mL). The resulting solution was stirred at RT till completion of the reaction. Then the mixture was diluted with AcOEt, washed with water, dried with $Na_2SO_4$ and concentrated. The crude product was purified by column (50%-100% AcOEt/PE gradient), yielding tert-butyl 3-(2-bromothiazole-5-carboxamido)-5-(4-fluorophenyl)-1H-pyrazole-1-carboxylate (160 mg, 20%) as a white solid.

$^1$H-NMR (400 MHz, $CDCl_3$): δ (ppm): 11.39 (s, 1 NH), 8.56 (s, 1H), 7.79 (t, J=7 Hz, 2H), 7.31 (t, J=8.6 Hz, 2H), 6.96 (s, 1H), 1.71 (s, 9H).

Benzylamine (0.1 mL, 0.87 mmol) was added to a solution of tert-butyl 3-(2-bromothiazole-5-carboxamido)-5-(4-fluorophenyl)-1H-pyrazole-1-carboxylate (160 mg, 0.43 mmol) in dioxane (3 mL). The resulting solution was stirred at 85° C. for 24 hrs. The solvent was evaporated and the crude product was purified by column (0-10% MeOH/AcOEt gradient), yielding 2-(benzylamino)-N-(5-(4-fluorophenyl)-1H-pyrazol-3-yl)thiazole-5-carboxamide (180 mg, 90%) as a solid.

$^1$H-NMR (400 MHz, $CDCl_3$): δ (ppm): 7.85 (s, 1H), 7.64 (s, 2H), 7.34-7.27 (m, 5H), 7.08 (t, J=8.6 Hz, 2H), 6.71 (s, 1H), 4.51 (s, 2H), 4.39 (s, 2H).

MS (ESI): m/z: 394.37 [MH$^+$].

BMS was added to a solution of 2-(benzylamino)-N-(5-(4-fluorophenyl)-1H-pyrazol-3-yl)thiazole-5-carboxamide (50 mg, 0.13 mmol) in THF (1 mL). The resulting solution was stirred at RT overnight. The reaction was then quenched with MeOH (0.5 mL) and 1N HCl was added until pH=2. After stirring the reaction mixture at RT for 3 hrs, the organic solvents were evaporated and the aqueous solution was neutralized with a $NaHCO_3$ saturated aqueous solution, extracted with AcOEt, dried with $Na_2SO_4$ and concentrated. The crude product was purified by column (0-2% MeOH/AcOEt gradient), yielding N-benzyl-5-((5-(4-fluorophenyl)-1H-pyrazol-3-ylamino)methyl)thiazol-2-amine (59 mg, 98%).

$^1$H-NMR (400 MHz, $CDCl_3/CD_3OD$): δ (ppm): 7.49 (s, 2H), 7.30-7.27 (m, 5H), 7.03 (t, J=8 Hz, 2H), 6.94 (s, 1H), 5.82 (s, 1H), 4.35 (s, 2H), 4.28 (s, 2H).

MS (ESI): m/z: 380.34 [MH$^+$].

N-Benzyl-5-((5-(4-fluorophenyl)-1H-pyrazol-3-ylamino) methyl)thiazol-2-amine (59 mg, 0.13 mmol) was dissolved in methanolic HCl (3 N, 1 mL) and AcOEt was added. The precipitated solid was filtered by decantation and dried in vacuo, yielding N-benzyl-5-((5-(4-fluorophenyl)-1H-pyrazol-3-ylamino)methyl)thiazol-2-amine dihydrochloride as a yellow solid (14 mg, 25%).

Mp. 78-80° C.

Preparation of 2n: N-Methyl-5-((4-p-tolylthiazol-2-ylamino)methyl)thiazol-2-amine dihydrochloride

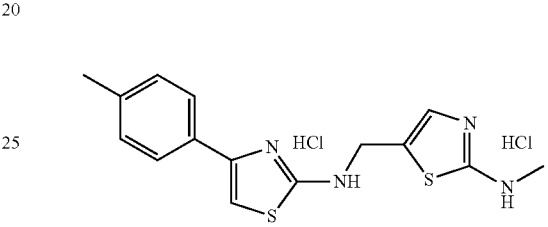

Compound 2n was prepared as described for 2w, starting from 4-p-tolylthiazol-2-amine and 2-(methyl(tetrahydro-2H-pyran-2-yl)amino)thiazole-5-carbaldehyde: (28 mg, 80%). Mp. 114-116° C.

$^1$H-NMR (400 MHz, $CDCl_3$): δ (ppm): 7.97 (t, J=5.6 Hz, 1H), 7.75 (d, J=8 Hz, 2H), 7.33 (m, 1H), 7.18 (d, J=8 Hz, 2H), 6.99 (s, 1H), 6.96 (s, 1H), 4.46 (d, J=5.6 Hz, 2H), 2.76 (d, J=4.3 Hz, 3H), 2.30 (s, 3H).

$^{13}$C-NMR (100 MHz, $CDCl_3$): δ (ppm): 169.73, 167.45, 149.76, 137.43, 136.43, 132.15, 128.97, 125.53, 121.96, 100.52, 40.52, 30.62, 20.76.

MS (ESI): m/z: 317.24 ([MH$^+$].

Preparation of 2: N-Methyl-5-((5-p-tolylthiazol-2-ylamino)methyl)thiazol-2-amine dihydrochloride

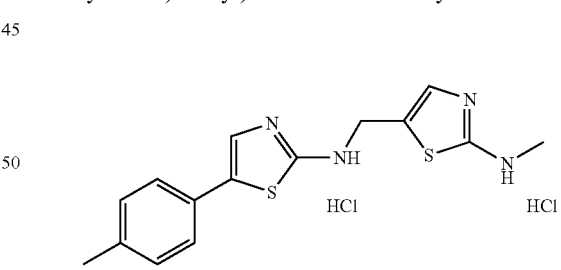

Compound 2o was prepared as described for 2w, starting from 5-p-tolylthiazol-2-amine and 2-(methyl(tetrahydro-2H-pyran-2-yl)amino)thiazole-5-carbaldehyde: (70 mg, 78%). Mp. not determined (it decomposes above 140° C.).

$^1$H-NMR (400 MHz, $CDCl_3$): δ (ppm): 7.97 (t, J=5.6 Hz, 1H), 7.75 (d, J=8 Hz, 2H), 7.33 (m, 1H), 7.19 (d, J=8 Hz, 2H), 7.00 (s, 1H), 6.96 (s, 1H), 4.46 (d, J=5.6 Hz, 2H), 2.75 (d, J=5 Hz, 3H), 2.31 (s, 3H).

$^{13}$C-NMR (100 MHz, $CDCl_3$): δ (ppm): 170.65, 168.37, 150.68, 138.36, 137.35, 133.08, 129.89, 126.45, 122.89, 101.45, 41.44, 31.55, 21.68.

MS (ESI): m/z: 317.38 ([MH$^+$].

Preparation of 2p: N-(Pyridin-2-yl)-5-((thiazol-2-ylamino)methyl)thiazol-2-amine trihydrochloride

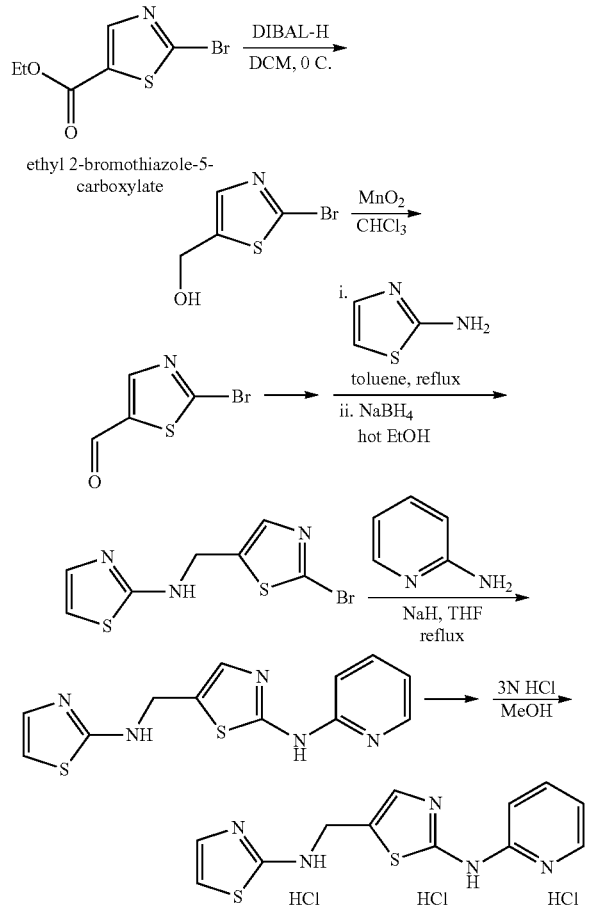

DIBAL-H (1M in hexanes, 16.88 mL, 16.88 mmol) was added to a solution of ethyl 2-bromothiazole-5-carboxylate (2 g, 8.44 mmol) in $CH_2Cl_2$ (16 mL) at 0° C. The mixture was stirred to RT for 6 hrs. After quenching with MeOH (6 mL), $Et_2O$ and a saturated solution of Rochelle's salt were added, the reaction mixture was stirred until the two phases were clearly separated. The organic phase was dried, concentrated and purified by column chromatography (30%-100% AcOEt/PE gradient), yielding (2-bromothiazol-5-yl)methanol (1.44 g, 88%) as an oil.

$^1$H-NMR (400 MHz, $CDCl_3$): δ (ppm): 7.25 (s, 1H), 4.93 (bs, 1H), 4.69 (s, 2H).

$^{13}$C-NMR (100 MHz, $CDCl_3$): δ (ppm): 144.25, 139.58, 136.89, 57.19.

MS (ESI): m/z: 193.83 [MH$^+$].

$MnO_2$ (3.8 g, 37.10 mmol) was added to a solution of (2-bromothiazol-5-yl)methanol (1.44 g, 7.42 mmol) in $CHCl_3$ (20 mL). The resulting mixture was stirred at RT for 3 days. Then the solution was filtered through celite and concentrated, yielding 2-bromothiazole-5-carbaldehyde (870 mg, 61%) as a white solid.

$^1$H-NMR (400 MHz, $CDCl_3$): δ (ppm): 9.95 (s, 1H), 8.16 (s, 1H).

$^{13}$C-NMR (100 MHz, $CDCl_3$): δ (ppm): 180.93, 150.47, 145.48, 142.91.

MS (ESI): m/z: 192.31 ([MH$^+$]).

A solution of 2-bromothiazole-5-carbaldehyde (150 mg, 0.78 mmol) and 2-amino-thiazole (78 mg, 0.78 mmol) in toluene (7 mL) and 3 Å molecules sieves were stirred at reflux overnight. The strong yellow solution of the corresponding imine was then poured over $NaBH_4$ (147 mg, 3.9 mmol) in hot EtOH (50 mL). The colorless solution was filtered, concentrated and purified by column chromatography (30% AcOEt/PE) yielding N-((2-bromothiazol-5-yl)methyl)thiazol-2-amine (110 mg, 51%) as a solid.

$^1$H-NMR (400 MHz, $CD_3OD/CDCl_3$): δ (ppm): 7.33 (s, 1H) 6.95 (d, J=3.7 Hz, 1H), 6.40 (d, J=3.7 Hz, 1H), 4.49 (s, 2H), 2.9 (bs, 1H).

$^{13}$C-NMR (100 MHz, $CD_3OD/CDCl_3$): δ (ppm): 169.00, 140.64, 139.95, 138.38, 136.27, 107.53, 41.29.

MS (ESI): m/z: 276.30 ([MH$^+$]).

2-Aminopyridine (0.150 g, 1.6 mmol) was added to a suspension of NaH (64 mg, 1.6 mmol) in THF (4 mL). The resulting solution was stirred at 65° C. for 45 min. Then N-((2-bromothiazol-5-yl)methyl)thiazol-2-amine (110 mg, 0.4 mmol) was added and the reaction mixture was stirred at 65° C. overnight. The reaction was quenched with water and the reaction mixture was extracted with AcOEt. The organic phase was dried, concentrated and purified by column chromatography (in AcOEt). Precipitation from $CHCl_3$ was conducted to eliminate excess 2-aminopyridine N-(Pyridin-2-yl)-5-((thiazol-2-ylamino)methyl)thiazol-2-amine was obtained as a weakly yellow solid (15 mg, 14%).

$^1$H-NMR (400 MHz, DMSO-$d_6$): δ (ppm): 11.12 (bs, 1H), 8.24 (d, J=4.4 Hz, 1H), 7.97 (s, 1H), 7.67 (t, J=8 Hz, 1H), 7.26 (s, 1H), 7.05 (d, J=3.2 Hz, 1H), 7.02 (d, J=8.4 Hz, 1H), 6.88 (t, J=5.6 Hz, 1H), 6.64 (d, J=4.4 Hz, 1H), 4.53 (d, J=4.8 Hz, 2H).

$^{13}$C-NMR (100 MHz, DMSO-$d_6$): δ (ppm): 168.17, 159.06, 151.41, 146.15, 138.34, 137.51, 135.44, 126.24, 115.52, 110.34, 106.35, 39.96.

MS (ESI): m/z: 290.32 ([MH$^+$].

N-(Pyridin-2-yl)-5-((thiazol-2-ylamino)methyl)thiazol-2-amine (15 mg, 0.05 mmol) was dissolved in methanolic HCl (3 N, 1 mL) and $Et_2O$ was added. The precipitated solid was filtered by decantation and dried in vacuum, yielding N-(pyridin-2-yl)-5-((thiazol-2-ylamino)methyl)thiazol-2-amine trihydrochloride (14 mg, 2%, 95.5% pure by HPLC).

Mp. decomposition >145° C.

Preparation of 2q: N-Benzyl-5-((5-fluoropyridin-2-ylamino)methyl)pyridin-2-amine

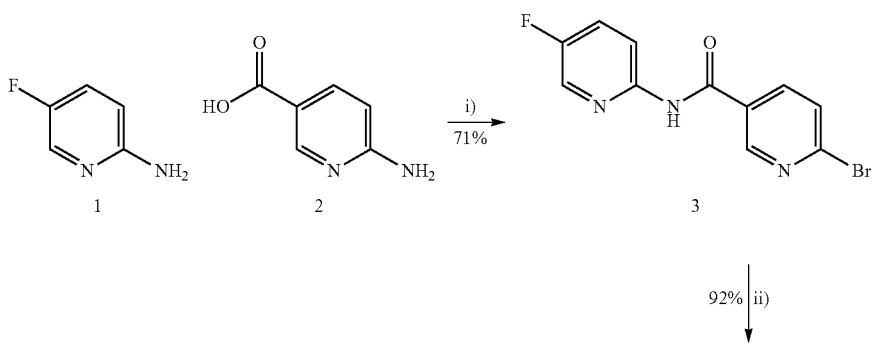

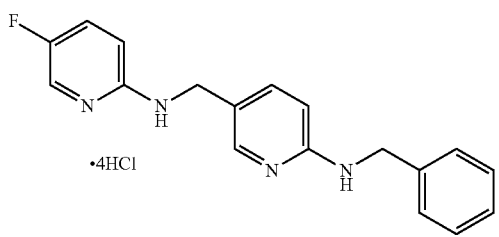

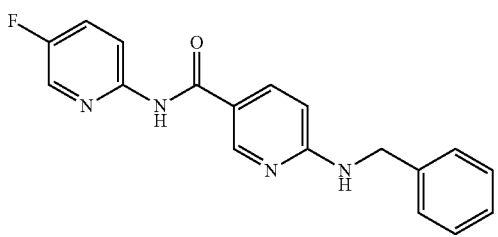

Reagents: i) 2-chloro-1-methylpyridinium iodide/DIPEA/THF/24 h RT ii) Benzylamine/140° C.
iii) BMS/THF/reflux, 24 h iv) MeOH/HCl/RT/1 h 2-Chloro-1-methylpyridinium iodide (2.2 g, 9.8 mmol) and DIPEA (1 ml) were added to a mixture of 5-fluoropyridin-2-amine 1 (554 mg, 4.9 mmol) and 6-bromonicotinic acid 2 (1 g, 4.9 mmol) in THF. The reaction mixture was stirred at rt for 2 days. At the conclusion of the reaction, the reaction mixture was concentrated to ⅓ of its volume and the precipitated product was filtered off. The filtrate was concentrated, diluted with chloroform (100 ml), washed with water and brine and then dried over $Na_2SO_4$. Evaporation of the solvent gave a crude yellow product, which crystallized in EtOAc to give 6-bromo-N-(5-fluoropyridin-2-yl)nicotinamide 3 (1.05 g, 71%) as a white solid. Mp. 173-174° C.

$^1$H-NMR (400 MHz, $CDCl_3$): δ=11.27 (s, 1H), 8.94 (s, 1H), 8.43 (s, 1'H), 8.27 (d, J=8.0 Hz, 1H), 8.2 (d, J=12 Hz, 1H), 7.83 (m, 2H).

MS (ESI): m/z=(297, M+H).

The 6-bromo-N-(5-fluoropyridin-2-yl)nicotinamide 3 (500 mg, 1.68 mmol) was dissolved in benzyl amine (2 ml), and heated at 140° C. for 48 h. Then the reaction mixture was concentrated. The product was recrystallized from ethyl acetate and pet-ether to give 6-(benzylamino)-N-(5-fluoropyridin-2-yl)nicotinamide 4 (500 mg, 92%) as a white solid. Mp. 167-168° C.

$^1$H-NMR (400 MHz, $CDCl_3$): δ=10.5 (s, 1H), 8.69 (s, 1H), 8.36 (s, 1H), 8.17 (s, 1H), 7.79 (s, 1H) 7.24-7.70 (m, 7H), 6.57 (d, J=8.0 Hz, 1H) 4.18 (s, 2H).

MS (ESI): m/z=(323, M+H).

BMS (400 μL) was added to a solution of 6-(benzylamino)-N-(5-fluoropyridin-2-yl)nicotinamide 4 in THF (20 mL). The reaction mixture was refluxed for 16 hrs. Then the reaction mixture was cooled to RT. MeOH (2 mL), followed by conc. HCl were added. The reaction mixture was refluxed for 8 hrs, concentrated and diluted with water (2 mL). The pH was adjusted to 14 and the reaction mixture was extracted with chloroform (50 mL×2). All organic phases were washed with brine and dried over $Na_2SO_4$. Evaporation of the solvent gave a crude product which was purified on silica gel (1:1, EtOAc: Pet-ether) to give N-benzyl-5-((5-fluoropyridin-2-ylamino)methyl)pyridin-2-amine 5. This was treated with HCl/MeOH to give the corresponding salt (50 mg 13%) as a white solid. Mp. 166-168° C.

$^1$H-NMR (400 MHz, $CDCl_3$): δ=8.11 (d, J=1.6, 1H) 7.99 (d, J=2.8, 1H) 7.46 (dd, J=2.4, J=8.4 Hz, 1H) 7.33-7.37 (m, 3H), 7.28 (m, 3H), 7.20 (dt, J=3.2, J=8.0 Hz, 1H) 6.35-6.40 (m, 2H) 4.96 (brs, 1H) 4.61 (s, 1H) 4.53 (d, J=6.0 Hz, 2H), 4.34 (d, J=5.2 Hz 2H)

MS (ESI): m/z=(309, M+H)

Preparation of 2s:

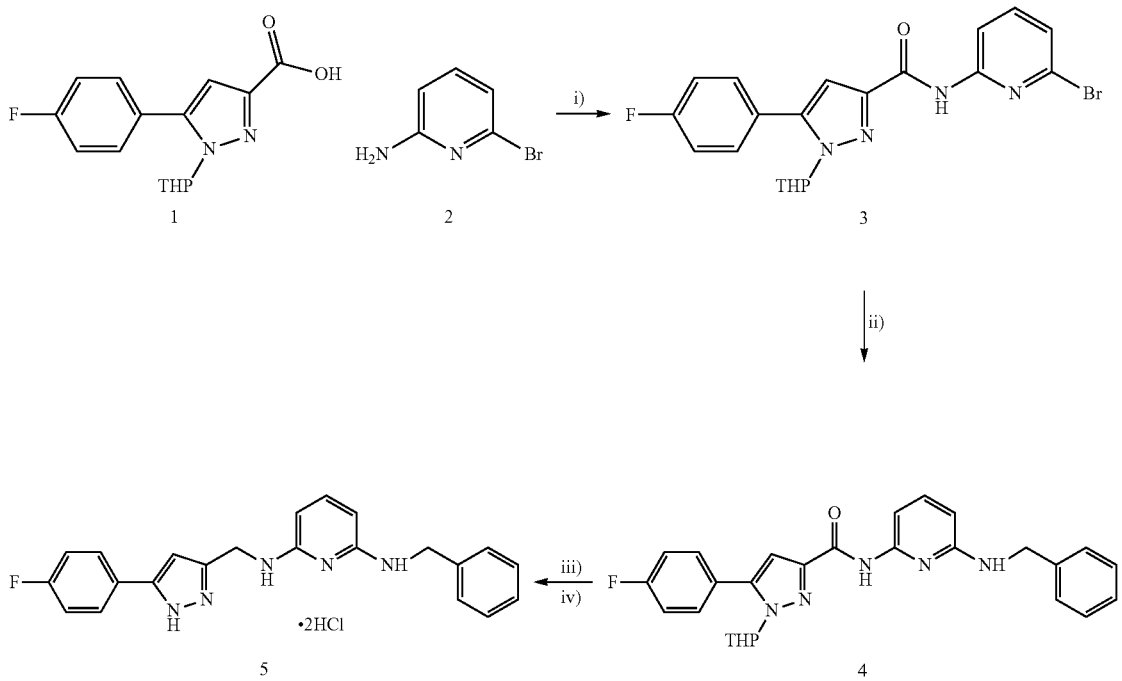

Reagents: i) 2-chloro-1-methylpyridinium iodide/DIPEA/RT/3 days ii) Benzylamine/110° C./overnight iii) BMS/THF/MeOH/HCl iv) MeOH/HCl To a suspension of 5-(4-fluorophenyl)-1-(tetrahydro-2H-pyran-2-yl)-1H-pyrazole-3-carboxylic acid 1 (400 mg, 1.37 mmol) and 2-chloro-1-methylpyridinium iodide (524 mg, 2.0 mmol) in THF (20 ml), DIPEA (0.46 ml) followed by 6-bromopyridin-2-amine 2 (237 mg, 1.37 mmol) were added. The suspension was stirred for 72 hrs. Then the reaction mixture was concentrated, diluted in water (10 ml) and extracted with dichloromethane (50 ml×2). All organic phases were washed with water and brine, dried over $Na_2SO_4$ and concentrated. The residue was purified on a silica gel column (EtOAc: pet-ether 1:4) to give N-(6-bromopyridin-2-yl)-5-(4-fluorophenyl)-1-(tetrahydro-2H-pyran-2-yl)-1H-pyrazole-3-carboxamide 3 (180 mg) as a white solid. Mp. 151-152° C.

$^1$H-NMR (400 MHz, $CDCl_3$): δ=9.53 (s, 1H), 8.31 (d, J=8.0 Hz, 1H), 7.83 (dd, J=5.2, J=8.8 Hz, 2H), 7.64 (t, J=8.0 Hz, 2H), 7.30 (m, 2H) 7.13 (t, J=9.2 Hz, 2H), 6.04 (dd, J=2.4 Hz, J=10 Hz, 1H), 4.26 (d, J=11.0 Hz, 1H), 3.86 (t, J=11.6 Hz, 1H), 2.52-2.60 (m, 1H), 2.11 2.16 (m, 2H), 1.27-1.57 (m, 2H).

N-(6-Bromopyridin-2-yl)-5-(4-fluorophenyl)-1-(tetrahydro-2H-pyran-2-yl)-1H-pyrazole-3-carboxamide 3 (300 mg, 0.67 mmol) was dissolved in benzylamine (3 ml). The reaction mixture was heated for 24 hrs at 130° C. Then the reaction mixture was purified on a silica gel column (1:5 EtOAc: Pet-ether) to give N-(6-(benzylamino)pyridin-2-yl)-5-(4-fluorophenyl)-1-(tetrahydro-2H-pyran-2-yl)-1H-pyrazole-3-carboxamide 4 as a white solid (187 mg, 59%). Mp. 139-140° C.

$^1$H-NMR (400 MHz, $CDCl_3$): δ=7.79 (brs, 2H), 7.18-7.39 (m, 8H), 7.09 (t, J=7.6 Hz, 2H), 6.94 (s, 1H), 6.84 (d, J=8.0 Hz, 1H), 6.43 (d, J=8.0 Hz, 1H), 5.98 (d, J=9.6 Hz, 1H), 4.64 (s, 2H), 3.96 (d, J=10.8 Hz, 1H), 3.54 (t, J=10.4 Hz, 1H), 2.54 (m, 1H), 2.02-2.10 (m, 2H), 1.56-1.67 (m, 3H).

Boran dimethylsufide (50 μL) was added to a solution of N-(6-(benzylamino)pyridin-2-yl)-5-(4-fluorophenyl)-1-(tetrahydro-2H-pyran-2-yl)-1H-pyrazole-3-carboxamide 4 (180 mg, 0.38 mmol) in THF (10 ml). The reaction mixture was refluxed over night and cooled. MeOH was added, followed by conc. HCl and the reaction mixture was heated for 5 hrs. Then the reaction mixture was concentrated in vacuum, diluted with water (5 ml) and extracted with chloroform (50 ml×2). The combined organic layers were washed with water and brine, then dried over $Na_2SO_4$ and concentrated under reduced pressure. The crude product was purified on silica gel (50% EtOAc: pet-ether) to give $N^2$-benzyl-$N^6$-((5-(4-fluorophenyl)-1H-pyrazol-3-yl)methyl)pyridine-2,6-diamine 5 (20 mg) as an oily material, which was treated with methanolic hydrochloric acid for 2 hrs. The solvent was evaporated under reduced pressure to give a gummy material (20 mg).

$^1$H-NMR (400 MHz, $CDCl_3$): δ=7.75 (dd, J=5.6 Hz, J=8.4 Hz, 2H), 7.28-7.37 (m, 8H), 7.11 (t, J=8.8 Hz, 2H), 6.44 (s, 1H), 3.93 (s, 2H), 3.87 (s, 2H).

MS (ESI): m/z=374 (M+H)

Preparation of 2t: N-Benzyl-6-((5-(4-fluorophenyl)-1H-pyrazol-3-ylamino)methyl)pyridin-2-amine

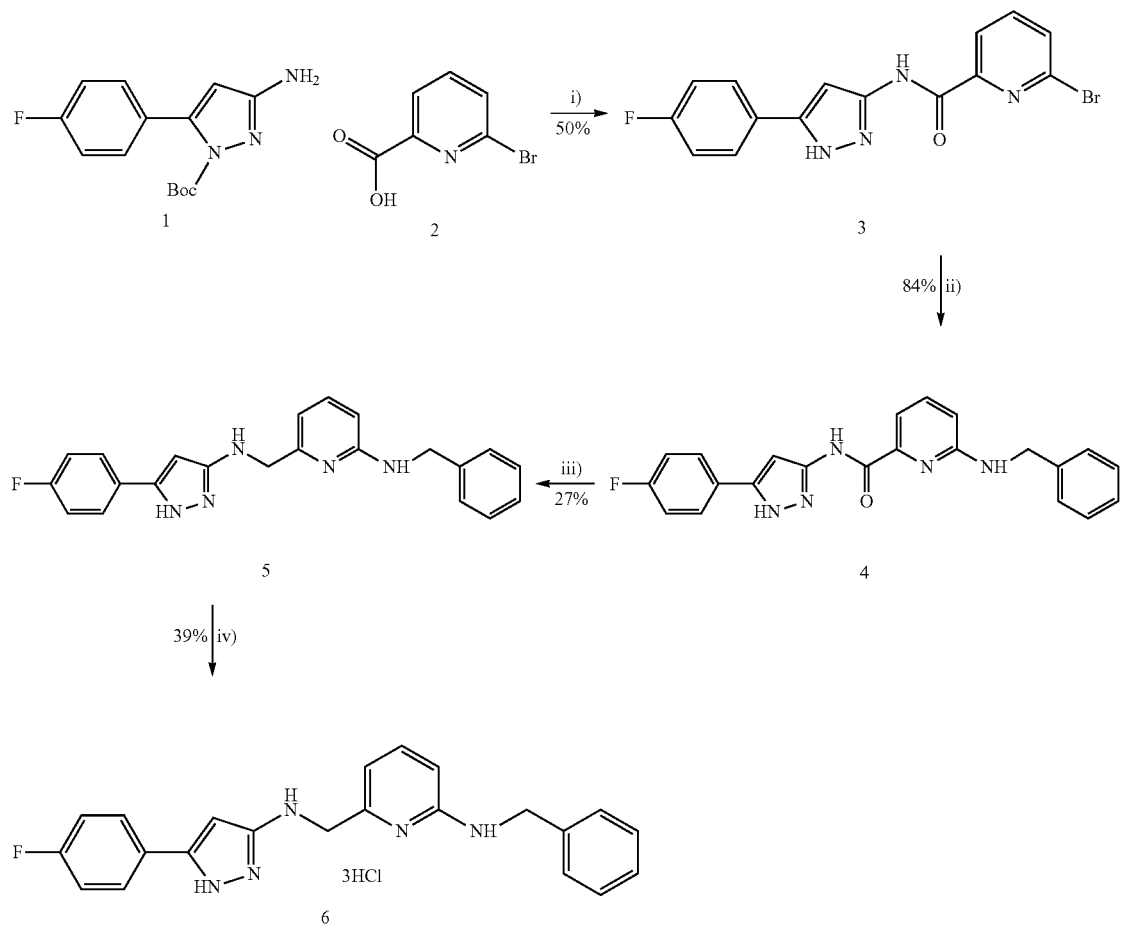

Reagents: i) 2-chloro-1-methylpyridinium iodide/DIPEA/RT/3 days ii) Benzylamine/110° C./overnight iii) BMS/THF/MeOH/HCl 2-Chloro-1-methylpyridinium iodide (950 mg, 3.7 mmol) and DIPEA (0.7 mL) were added to a solution of 6-bromopicolinic acid 2 (500 mg, 2.47 mmol) in dry DCM/DMF (30/5 mL). The reaction mixture was stirred for 1 hr. tert-Butyl 3-amino-5-(4-fluorophenyl)-1H-pyrazole-1-carboxylate 1 was added (650 mg, 2.47 mmol). The resulting yellow reaction mixture was stirred for 3 days. Then the reaction mixture was concentrated under reduced pressure, the residue was diluted in chloroform and washed with water and brine, and then dried over $Na_2SO_4$. The resulting crude mixture was purified on silica gel (EtOAc: pet-ether, 1:3) to give 6-bromo-N-(5-(4-fluorophenyl)-1H-pyrazol-3-yl) picolinamide 3 (450 mg, 50%) as a white solid.

Mp. 245-247° C.

$^1$H-NMR (400 MHz, $CDCl_3$): δ=10.3 (s, 1H), 8.15 (d, J=7.6 Hz, 1H), 8.02 (t, J=7.6 Hz, 1H), 7.95 (d, J=8.0 Hz, 1H), 7.82 (dd, J=5.2 Hz, J=8.0 Hz, 2H), 7.32 (t, J=8.8 Hz 1H), 7.05 (s, 1H).

MS (ESI): m/z=361 (M+H).

6-Bromo-N-(5-(4-fluorophenyl)-1H-pyrazol-3-yl)picolinamide 3 (200 mg, 0.55 mmol) was dissolved in neat benzylamine (5 ml). The reaction mixture was heated for 24 hrs. Then the solvent was evaporated and the residue was purified on silica gel (EtOAc: pet-ether, 1:4) to give 6-(benzylamino)-N-(5-(4-fluorophenyl)-1H-pyrazol-3-yl) picolinamide 4 (180 mg, 84%).

Mp. 185-187° C.

$^1$H-NMR (400 MHz, $CDCl_3$): δ 10.1 (brs, 1H), 7.81 (d, J=5.6, J=8.4 Hz, 2H), 7.60 (t, J=7.6 2H), 7.44 (d, J=7.2 Hz 2H), 7.28-7.36 (m, 5H), 7.23 (t, J=7.2 Hz 1H), 7.02 (brs, 1H), 6.79 (d, J=8.4 Hz 1H), 4.58 (s, 2H).

MS (ESI): m/z=388 (M+H).

Boron dimethylsulfide (50 mg, 0.66 mmol) was added to a solution of 6-(benzylamino)-N-(5-(4-fluorophenyl)-1H-pyrazol-3-yl)picolinamide 4 (150 mg, 0.37 mmol). The reaction mixture was refluxed for 16 hrs. After cooling the reaction mixture to RT MeOH (2 mL), followed by conc. HCl were added. The reaction mixture was refluxed for another 12 hrs. The reaction mixture was concentrated and diluted with water (4 ml) and the pH was adjusted to 12 using NaOH solution. The reaction mixture was extracted with chloroform (40×3 mL). All organic layers were then washed with water and brine, then dried over $Na_2SO_4$, and the crude product was purified on silica gel column (100% EtOAc) to give an oily material (40 mg, 27%), which was then treated with HCl/MeOH to give N-benzyl-6-((5-(4-fluorophenyl)-1H-pyrazol-3-ylamino)methyl)pyridin-2-amine hydrochloride salt 6 (20 mg, 39%).

Mp. 133-134° C.

$^1$H-NMR (400 MHz, $CDCl_3$): δ=8.88 (br, 1H) 7.82 (brs, 2H), 7.40 (m, 5H), 6.99 (d, J=5.2 Hz 1H), 6.87 (brs, 1H), 6.2 (brs, 1H), 5.76 (brs, 1H), 4.69 (brs, 2H), 4.52 (brs, 2H).

MS (ESI): m/z=374 (M+H).

Preparation of 2u

Preparation of 3-(2,3-dihydrothiophen-2-yl)-N-((5-(4-fluorophenyl)-1H-pyrazol-3-yl)methyl)-1H-pyrazol-5-amine (7)

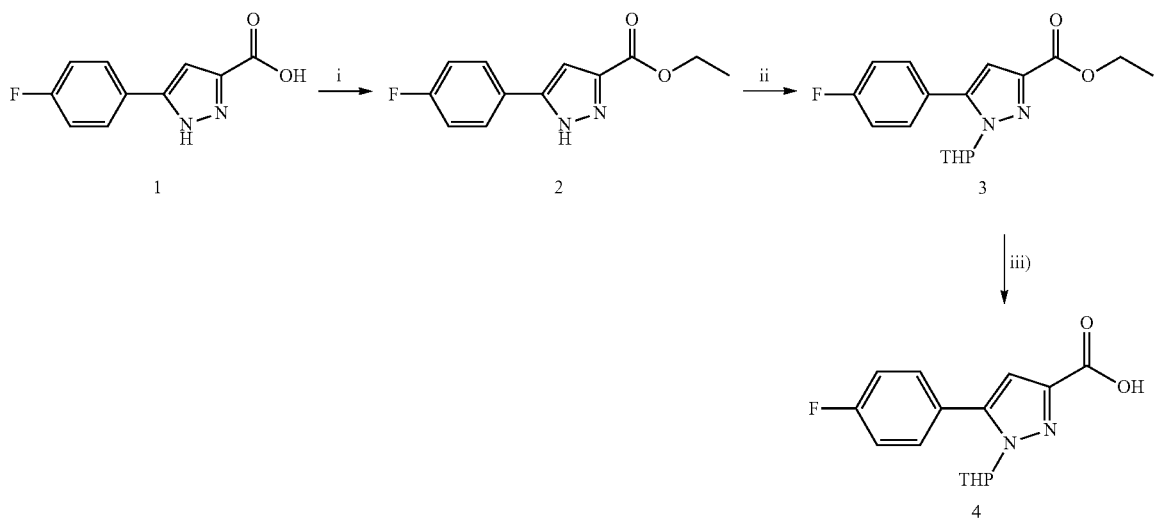

Reagents: i) EtOH, $H_2SO_4$/Reflux 16 h ii) DHP/TFA/THF/Reflux 16 h iii) LiOH/$H_2O$/MeOH

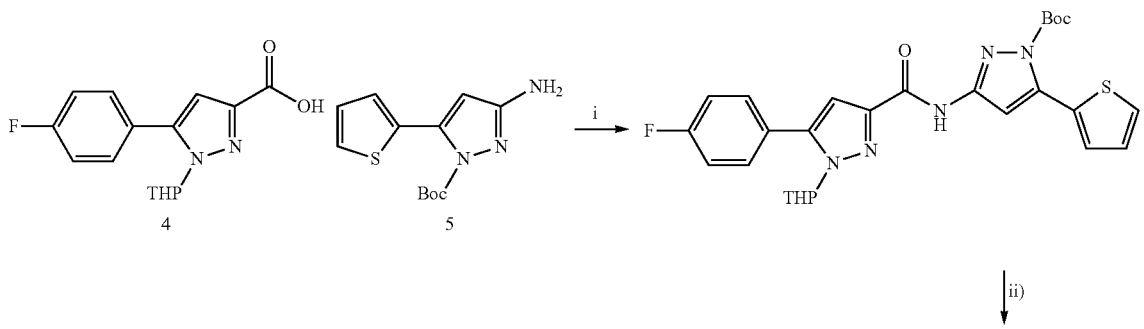

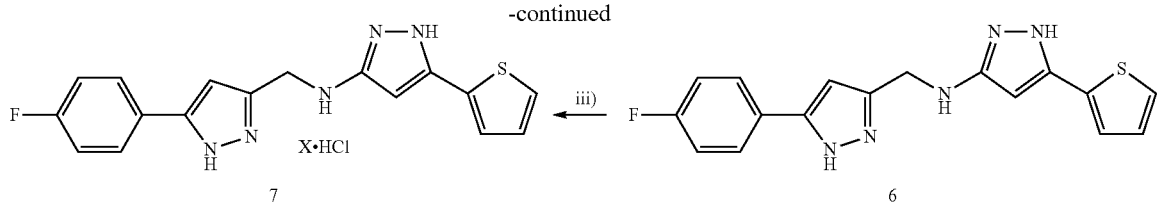

Reagents: i) 2-chloro-1-methylpyridinium iodide/DCM/DIPEA ii) BMS/THF/reflux iii) HCl/MeOH 3-4 Drops of conc. $H_2SO_4$ were added to a solution of 5-(4-fluorophenyl)-1H-pyrazole-3-carboxylic acid 1 in EtOH. The reaction mixture was refluxed for 2 days. The reaction mixture was concentrated and diluted with chloroform (100 ml) and washed with saturated $NaHCO_3$ solution, water and brine, and dried over $Na_2SO_4$. Evaporation of the solvent under vacuum gave ethyl 5-(4-fluorophenyl)-1H-pyrazole-3-carboxylate 2 as a brown solid (1.05 g, 93%).
Mp. 148-150° C.
$^1$H-NMR (400 MHz, $CDCl_3$): δ=7.77 (dd, J=5.6 Hz, J=8.4 Hz, 2H), 7.13 (t, J=8.4 Hz, 2H), 7.06 (s, 1H), 4.41 (q, J=7.2 Hz, 2H), 1.40 (t, J=7.2 Hz, 3H).
$^{13}$C-NMR (100 MHz, $CDCl_3$): δ 164.5, 162.1, 160.6, 127.9, 127.8, 116.3, 116.1, 105.8, 61.8, 14.6.
MS (ESI): m/z=235 (M+H).

DHP (20.4 mmol, 1.7 ml) was added to a solution of ethyl 5-(4-fluorophenyl)-1H-pyrazole-3-carboxylate 2 (800 mg, 3.4 mmol) in dry THF (50 ml), followed by a catalytic amount of TFA (20 µL). Then the reaction mixture was refluxed for 2 days. The reaction mixture was concentrated, diluted with chloroform (100 ml), washed with water and brine, and dried over $Na_2SO_4$. Purification of the crude product on silica gel (Pet-ether:EtOAc, 9:1) gave ethyl 5-(4-fluorophenyl)-1-(tetrahydro-2H-pyran-2-yl)-1H-pyrazole-3-carboxylate 3 (600 mg, 55.5%) as a white solid. Mp. 95-96° C.
$^1$H-NMR (400 MHz, $CDCl_3$): δ=7.84 (dd, J=5.6, J=8.4 Hz, 2H), 7.15 (s, 1H), 7.10 (1, J=8.8 Hz, 2H), 6.33 (dd, J=2.4, J=9.6 Hz, 1H), 4.40 (q, J=7.2 Hz 2H), 4.09-4.16 (m, 2H), 3.75-3.80 (m, 1H), 2.56-2.61 (m, 1H), 2.15 (m, 1H), 2.0 (d, J=12.8 Hz, 1H), 1.56-1.78 (m, 2H), 1.42 (t, J=7.2 Hz, 3H).

LiOH (120 mg, 5 mmol) was added to a solution of ethyl 5-(4-fluorophenyl)-1-(tetrahydro-2H-pyran-2-yl)-1H-pyrazole-3-carboxylate 3 (1.1 g 3.4 mmol) in THF/$H_2O$ (1:1, 5 ml). The reaction mixture was stirred over night. The clear solution was concentrated, and suspended in chloroform (25 ml), The solid was filtered off and dried under vacuum to give 5-(4-fluorophenyl)-1-(tetrahydro-2H-pyran-2-yl)-1H-pyrazole-3-carboxylic acid 4 (987 mg, 99%) as a white solid. Mp. 188-190° C.
$^1$H-NMR (400 MHz, $CDCl_3$): δ=7.88 (dd, J=5.6 Hz, J=8.8 Hz, 2H), 7.20 (t, J=8.8 Hz, 2H), 6.82 (d, J=8.8 Hz, 1H), 6.71 (s, 1H), 3.90 (d, J=11.2 Hz, 1H), 3.55 (m, 1H), 2.31 (m, 1H), 2.02 (d, J=12 Hz, 1H), 1.76 (d, J=12.8 Hz, 1H), 1.52-1.65 (m, 2H).
MS (ESI): m/z=291 ($M^+$).

2-Chloro-1-methylpyridinium iodide (650 mg, 2.5 mmol) was added to a solution of 5-(4-fluorophenyl)-1-(tetrahydro-2H-pyran-2-yl)-1H-pyrazole-3-carboxylic acid 4 (500 mg, 1.72 mmol) in THF/DMF (20/2 ml), followed by DIPEA (0.5 ml). The reaction mixture was stirred for 30 min, then tert-butyl 3-amino-5-(thiophen-2-yl)-1H-pyrazole-1-carboxylate 5 (456 mg, 1.72 mmol) was added. The reaction mixture was stirred for 2 days. The reaction mixture was concentrated, diluted with chloroform (100 ml) and washed with water and brine, dried over $Na_2SO_4$ and the solvent was evaporated. The crude product was dried well and dissolved in THF (10 ml), subsequently BMS (0.3 ml) was added. The reaction mixture was heated for overnight and cooled, then MeOH and conc. HCl were added. The reaction mixture was again heated for another 5 hrs. The reaction mixture was cooled, concentrated and diluted with water (5 ml), the pH was adjusted to 14 with NaOH pellets, and extracted with chloroform (50 ml×2). All organic layers were washed with water and brine, dried over $Na_2SO_4$ and the solvent was evaporated. The crude product was purified on a silica gel column (4:1, EtOAc: pet-ether) to give N-((5-(4-fluorophenyl)-1H-pyrazol-3-yl)methyl)-5-(thiophen-2-yl)-1H-pyrazol-3-amine 7 (66 mg, 11% overall). Mp. 128-130° C.
$^1$H-NMR (400 MHz, $CDCl_3$): δ=4.76 (s, 2H), 6.33 (s, 2H), 7.02-7.06 (m, 3H), 7.28-7.50 (m, 2H), 7.73-7.74 (m, 2H).
MS (ESI): m/z=340 (M+H)

Preparation of 2w: N-Methyl-5-((thiazol-2-ylamino)methyl)thiazole-2-amine dihydrochloride

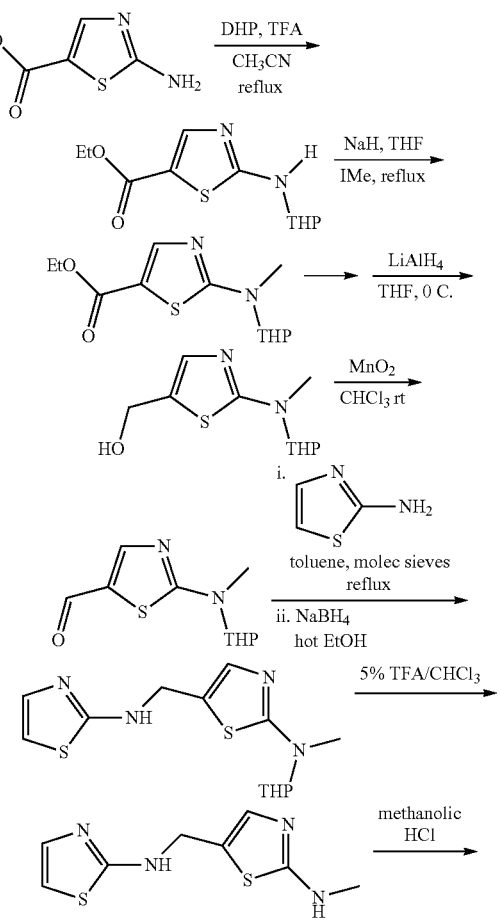

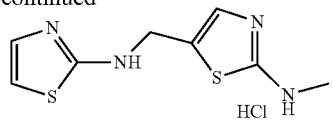

TFA (22 μL, 0.3 mmol) and DHP (3.9 mL, 43.5 mmol) were added to a suspension of ethyl 2-aminothiazole-5-carboxylate (5 g, 29 mmol) in CH$_3$CN (40 mL) at RT. The resulting mixture was stirred at reflux overnight. The reaction mixture was concentrated and dissolved in AcOEt/PE and kept at 4 C overnight. The resultant white solid was filtered and washed with PE, yielding ethyl 2-(tetrahydro-2H-pyran-2-ylamino)thiazole-5-carboxylate (4.73 g, 64%).

$^1$H-NMR (400 MHz, CDCl$_3$): δ (ppm): 7.85 (s, 1H), 6.69 (bs, 1H), 4.75 (t, J=3.5 Hz, 1H), 4.29 (q, J=4.5 Hz, 2H), 3.97 (m, 1H), 3.60 (m, 1H), 1.96 (m, 2H), 1.58 (m, 4H), 1.34 (t, J=4.5 Hz, 3H).

$^{13}$C-NMR (100 MHz, CDCl$_3$): δ (ppm): 173.26, 161.98, 145.98, 117.41, 83.63, 65.19, 60.82, 30.39, 24.88, 21.62, 14.33.

MS (ESI): m/z (%): 257.31 ([MH$^+$], 100%)

Ethyl 2-(tetrahydro-2H-pyran-2-ylamino)thiazole-5-carboxylate (4.73 g, 18.5 mmol) was added to a suspension of NaH (740 mg, 18.5 mmol) in THF (20 mL) at 0° C., followed by methyl iodide (1.15 mL, 18.5 mmol). The resulting mixture was heated at reflux during 3 hrs. After quenching with water and extracting with AcOEt, the crude product was purified by column chromatography (50% AcOEt/PE), yielding ethyl 2-(methyl(tetrahydro-2H-pyran-2-yl)amino)thiazole-5-carboxylate (2.02 g, 40%) as an oil.

$^1$H-NMR (400 MHz, CDCl$_3$): δ (ppm): 7.89 (s, 1H), 5.29 (t, J=3.8 Hz, 1H), 4.29 (q, J=4.5 Hz, 2H), 4.07 (d, J=7.3 Hz, 1H), 3.65 (td, J=7 Hz, 2 Hz, 1H), 3.09 (s, 3H), 1.96 (m, 1H), 1.75-1.55 (m, 5H), 1.34 (t, J=4.5 Hz, 3H).

$^{13}$C-NMR (100 MHz, CDCl$_3$): δ (ppm): 174.19, 162.02, 147.40, 116.83, 87.06, 68.37, 60.61, 32.47, 28.69, 24.97, 23.03, 14.30.

MS (ESI): m/z (%): 271.38 ([MH$^+$], 100%).

LiAlH$_4$ (425 mg, 11.20 mmol) was added to a solution of ethyl 2-(methyl(tetrahydro-2H-pyran-2-yl)amino)thiazole-5-carboxylate (2.02 g, 7.47 mmol) in THF (20 mL) at 0° C. in small portions. After stirring at 0° C. for 30 min, the reaction was quenched slowly by H$_2$O (1 mL), 5% NaOH (3 mL) and again H$_2$O (5 mL). Then AcOEt was added. The reaction mixture was dried with Na$_2$SO$_4$ and filtered through celite. The filtrate was concentrated and purified by column chromatography (30%-50% AcOEt/PE gradient), yielding (2-(methyl-(tetrahydro-2H-pyran-2-yl)amino)thiazol-5-yl) methanol (1.5 g, 93%) as an oil.

$^1$H-NMR (400 MHz, CDCl$_3$): δ (ppm): 7.00 (s, 1H), 5.16 (m, 1H), 4.65 (s, 2H), 4.06 (d, J=7 Hz, 1H), 3.63 (td, J=7.3 Hz, 2 Hz, 1H), 3.46 (s, 1H), 3.04 (s, 3H), 1.95-1.52 (m, 6H).

$^{13}$C-NMR (100 MHz, CDCl$_3$): δ (ppm): 171.68, 137.27, 126.45, 87.64, 68.308, 57.61, 32.34, 28.91, 25.11, 23.30.

MS (ESI): m/z (%): 229.29 ([MH$^+$], 100%).

MnO$_2$ (3 g, 34.82 mmol) was added to a solution of (2-(methyl(tetrahydro-2H-pyran-2-yl)amino)thiazol-5-yl) methanol (1.59 g, 6.96 mmol) in CHCl$_3$ (50 mL). The resulting mixture was stirred at RT for 2 days. Then the solution was filtered through celite and concentrated, yielding 2-(methyl-(tetrahydro-2H-pyran-2-yl)amino)thiazole-5-carbaldehyde (1.5 g, 96%) as a yellow oil.

$^1$H-NMR (400 MHz, CDCl$_3$): δ (ppm): 9.70 (s, 1H), 7.88 (s, 1H), 5.35 (t, J=3.8 Hz, 1H), 4.08 (d, J=7 Hz, 1H), 3.65 (td, J=7.3 Hz, 2 Hz, 1H), 3.12 (s, 3H), 1.97-1.55 (m, 6H).

$^{13}$C-NMR (100 MHz, CDCl$_3$): δ (ppm): 180.21, 175.18, 152.36, 128.35, 86.66, 67.92, 32.38, 28.11, 24.44, 22.44.

MS (ESI): m/z (%): 227.31 ([MH$^+$], 100%).

A solution of 2-(methyl(tetrahydro-2H-pyran-2-yl)amino) thiazole-5-carbaldehyde (250 mg, 1.10 mmol) and 2-aminothiazole (110 mg, 1.10 mmol) in toluene (11 mL) and molecular sieves 3 Å were stirred at reflux overnight. The strongly yellow solution of the corresponding imine was then poured over NaBH$_4$ (212 mg, 5.61 mmol) in hot EtOH (80 mL). The colorless solution was filtered, concentrated and purified by column chromatography yielding N-methyl-N-(tetrahydro-2H-pyran-2-yl)-5-((thiazol-2-ylamino)methyl) thiazol-2-amine (50 mg, 17%) as a solid.

$^1$H-NMR (400 MHz, CD$_3$OD/CDCl$_3$): δ (ppm): 7.11 (d, J=2.5 Hz, 2H), 6.50 (d, J=2.3 Hz, 1H), 5.73 (bs, 1H), 5.14 (dd, J=5.8 Hz, 1.8 Hz, 1H), 4.50 (s, 2H), 4.03 (d, J=7.3 Hz, 1H), 3.61 (td, J=7.0 Hz, 2 Hz, 1H), 3.02 (s, 3H), 1.97-1.52 (m, 6H).

$^{13}$C-NMR (100 MHz, CD$_3$OD/CDCl$_3$): δ (ppm): 171.31, 169.33, 138.83, 138.08, 122.57, 106.98, 87.54, 68.32, 42.34, 32.31, 28.89, 25.11, 23.28.

MS (ESI): m/z (%): 311.35 ([MH$^+$], 100%).

A solution of N-methyl-N-(tetrahydro-2H-pyran-2-yl)-5-((thiazol-2-ylamino)methyl) thiazol-2-amine (50 mg, 0.16 mmol) in 10% TFA in CHCl$_3$ (5 mL) was stirred at RT overnight. After evaporating the solvent, the residue was dissolved in MeOH, neutralized with Na$_2$CO$_3$ and extracted with CHCl$_3$. The organic phase was dried, concentrated and purified by column chromatography yielding N-methyl-5-((thiazol-2-ylamino)methyl)thiazol-2-amine (28 mg, 77%) as a solid.

$^1$H-NMR (400 MHz, CD$_3$OD/CDCl$_3$): δ (ppm): 7.02 (d, J=2.3 Hz, 1H), 6.92 (s, 1H), 6.44 (d, J=2.3 Hz, 1H), 4.38 (s, 2H), 3.37 (bs, 2H), 2.84 (s, 3H).

$^{13}$C-NMR (100 MHz, CD$_3$OD/CDCl$_3$): δ (ppm): 171.95, 169.74, 138.18, 137.23, 121.48, 106.87, 42.08, 31.6.

MS (ESI): m/z (%): 227.29 ([MH$^+$], 100%).

N-Methyl-5-((thiazol-2-ylamino)methyl)thiazol-2-amine (28 mg, 0.12 mmol) was dissolved in methanolic HCl (3 N, 1 mL) and Et$_2$O was added. The precipitated solid was filtered by decantation and dried in vacuo, yielding N-methyl-5-((thiazol-2-ylamino)methyl)thiazol-2-amine dihydrochloride as a white solid (29 mg, 79%). Mp. 128-130° C.

Preparation of 2y: N$^2$-((6-(benzylamino)pyridin-3-yl)methyl)pyridine-2,6-diamine

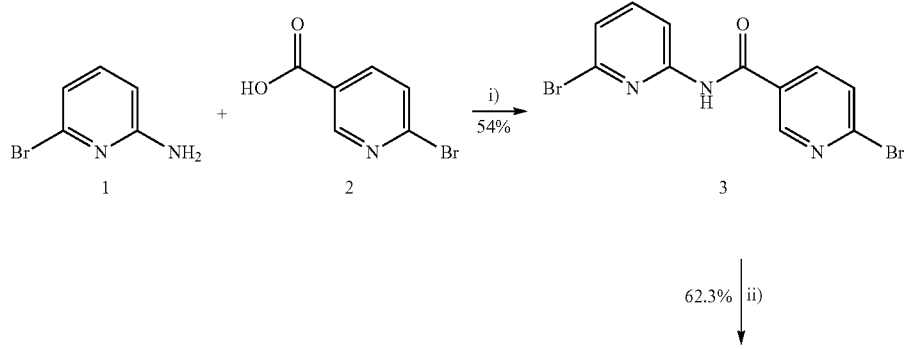

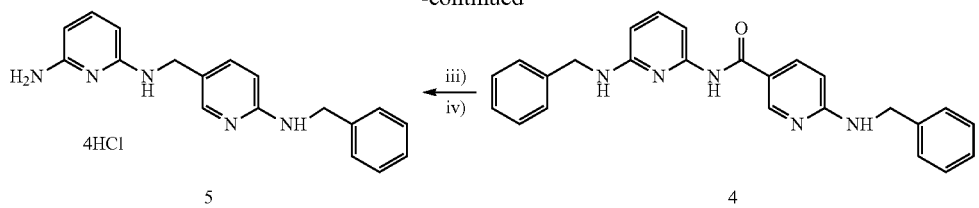

Reagents: i) Mukayama reagent/THF/DIPEA/RT 2 days ii) Benzylamine/140° C. 16 h iii) BMS/THF/24 h iv) HCl/MeOH/RT/3 h 2-Chloro-1-methylpyridinium iodide (2.18 g, 9.8 mmol) and DIPEA (2.1 ml 11.5 mmol) were added to a mixture of 6-bromo pyridin-2-amine 1 (1 g, 5.7 mmol) and 6-bromonicotinic acid 2 (1.16 g, 5.7 mmol) in THF. The reaction mixture was stirred at RT for 2 days. At the conclusion of the reaction, the reaction mixture was concentrated, diluted with chloroform (150 ml) and washed with water and brine, and then dried over $Na_2SO_4$. Evaporation of the solvent gave a crude yellow product, which crystallized in EtOAc to give 6-bromo-N-(6-bromopyridin-2-yl)nicotinamide 3 (1.1 g, 54%) as a white solid.

Mp. 171-173° C.

$^1$H-NMR (400 MHz, DMSO-$d_6$): δ=8.94 (d, J=2.0 Hz, 1H), 8.26 (dd, J=2.4, J=8.0 Hz, 2H), 7.80-7.84 (m, 2H), 7.45 (d, J=7.6 Hz, 1H).

MS (ESI): m/z=(357 M+H)

6-Bromo-N-(6-bromopyridin-2-yl)nicotinamide (650 mg, 1.8 mmol) 3 was dissolved in benzylamine (2 ml) and was heated at 140° C. for 24 hrs. Then the reaction mixture was concentrated, and the product was recrystallized from ethyl acetate and pet-ether to give 6-(benzylamino)-N-(6-(benzylamino)pyridine-2-yl)nicotinamide 4 (450 mg, 62%) as a white solid. Mp. 132-133° C.

$^1$H-NMR (400 MHz, DMSO-$d_6$): δ=8.72 (bs, 1H), 8.54 (s, 1H), 7.86 (s, 1H), 7.61 (d, J=8.4 Hz, 11H), 7.61 (s, 1H) 7.23-7.32 (m, 11H), 6.53 (d, J=8.8 Hz 1H), 4.53 (s, 2H), 4.44 (s, 2H).

MS (ESI): m/z=410 (M+H).

BMS (2.2 mmol, 165 μL) (400 μL) was added to a solution of 6-bromo-N-(6-bromopyridin-2-yl)nicotinamide 4 (300 mg, 0.73 mmol) in THF (20 ml). The reaction mixture was refluxed for 16 hrs. Then the reaction mixture was cooled to RT, MeOH (2 mL) was added, followed by conc. HCl. and the reaction mixture was refluxed for 8 hrs. The reaction mixture was concentrated and diluted with water (2 ml), the pH adjusted to 14 and the reaction mixture was extracted with chloroform (50 ml×2). The combined organic phases were washed with brine, dried over $Na_2SO_4$. Evaporation of the solvent gave a crude product that was purified on silica gel (1:1, EtOAc: pet-ether) to give a white solid which was treated with MeOH/HCl to give $N^2$-((6-(benzylamino)pyridin-3-yl)methyl)pyridine-2,6-diamine 5, hydrochloride salt (50 mg, 49%) as a white solid. Mp. 261-262° C.

$^1$H-NMR (400 MHz, CDCl$_3$): δ=9.62 (brs, 1H), 8.1 (s, 1H), 7.86 (brs, 1H), 7.54 (m, 2H), 7.28-7.37 (m, 7H), 6.89 (brs, 1H), 4.61 (brs, 2H), 4.13 (brs, 2H), 4.06 (brs, 2H).

MS (ESI): m/z=304 (M+H).

Preparation of 2z: N-(Pyridin-2-yl)-5-((4-p-tolylthiazol-2-ylamino)methyl)thiazol-2-amine trihydrochloride

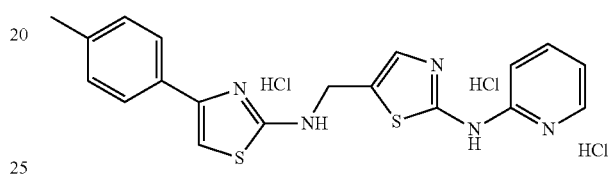

Compound 2z was prepared as described for 2p starting from 2-bromothiazole-5-carbaldehyde and 4-p-tolylthiazol-2-amine: (29 mg, 38%). Mp. 169-170° C.

$^1$H-NMR (400 MHz, DMSO-$d_6$): δ (ppm): 11.13 (s, 1H), 8.19 (d, J=4.83 Hz, 1H), 8.09 (t, J=6.4 Hz, 1H) 7.79 (d, J=8 Hz, 2H), 7.67 (t, J=8 Hz, 1H), 7.32 (s, 1H), 7.20 (d, J=8 Hz, 2H), 7.05 (s, 1H), 7.02 (s, 1H), 6.88 (t, J=6.4 Hz, 1H), 4.60 (d, J=4.8 Hz, 2H), 2.33 (s, 3H).

MS (ESI): m/z (%): 380.34 ([MH$^+$], 100%).

Preparation of 2aa: 4-(4-Chlorophenyl)-N-((2-(methylamino)thiazol-5-yl)methyl)thiazol-2-amine dihydrochloride

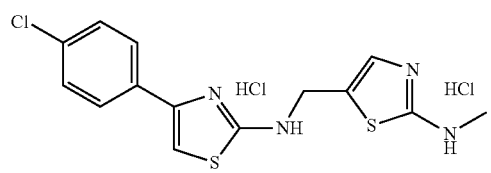 [SMILES: CNc1ncc(CNc2nc(-c3ccc(Cl)cc3)cs2)s1 ; Cl ; Cl]

Compound 2aa was prepared as described for 2w starting from 2-(methyl-(tetrahydro-2H-pyran-2-yl)amino)thiazole-5-carbaldehyde and 4-(4-chloro phenyl)thiazol-2-amine: (30 mg, 77%). Mp. 122-123° C.

$^1$H-NMR (400 MHz, CDCl$_3$): δ (ppm): 7.65 (d, J=8 Hz, 1H), 7.27 (d, J=8 Hz, 2H), 6.93 (s, 1 H), 6.63 (s, 1H), 4.43 (s, 2H), 2.8 (s, 3H).

$^{13}$C-NMR (100 MHz, CDCl$_3$): δ (ppm): 172.03, 168.77, 149.84, 136.63, 133.19, 133.11, 128.52, 127.13, 121.69, 101.67, 41.84, 31.65.

MS (ESI): m/z (%): 337.38 ([MH$^+$], 100%)

Preparation of 2ab N⁵-Propyl-N²-((6-(propylamino)pyridin-3-yl)methyl)pyridine-2,5-diamine

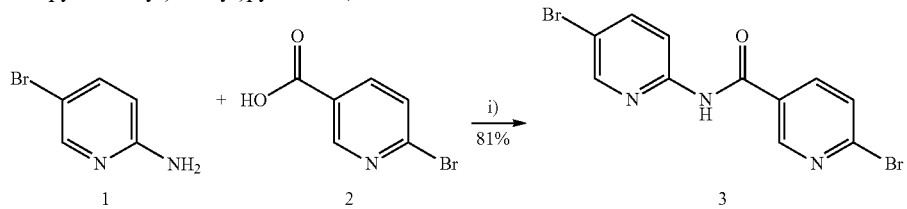

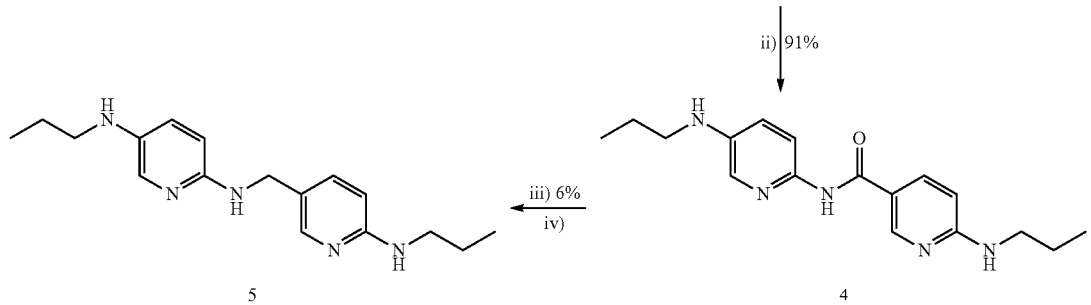

Reagents: i) 2-chloro-1-methylpyridinium iodide/DIPEA/RT/4 days ii) n-propylamine THF/DMSO/60-70° C./2d iii) BMS/THF/HCl 24 hours iv) MeOH/HCl rt/3 h DIPEA (5.5 ml, 29 mmol) and 2-chloro-1-methylpyridinium iodide (8 g, 26 mmol) were added to a solution of 5-bromopyridin-2-amine 1 (2.56 g, 14.8 mmol) and 6-bromonicotinic acid (3 g, 14.8 mmol) 2 in THF (150 ml). The reaction mixture was stirred at RT for 4 days. Then the precipitate was filtered off. The filtrate was concentrated and dissolved in chloroform (250 ml), washed with water and brine and dried over $Na_2SO_4$. The solvent was evaporated to give a crude product, which was recrystallized from ethyl acetate to give 6-bromo-N-(5-bromopyridin-2-yl)nicotinamide 3 (4.3 g, 81%) as a white solid. Mp. 204-205° C.

¹H-NMR (400 MHz, CDCl₃): δ=11.33 (s, 1H), 8.93 (s, 1H), 8.54 (s, 1H), 8.25 (d, J=8.8 Hz 1H), 8.17 (d, J=8.8 Hz 1H), 8.11 (d, J=6.4 Hz, 1H), 7.82 (d, J=8.4 Hz 1H).

MS (ESI): m/z=357 (M⁺)

A solution of 6-bromo-N-(5-bromopyridin-2-yl)nicotinamide 3 (1.1 g, 3.0 mmol) in n-propylamine (neat, 5 ml) was heated at 80° C. for 2 days. Then the solvent was evaporated to give 6-(propylamino)-N-(5-(propylamino)pyridin-2-yl)nicotinamide 4 as a white solid (880 mg, 91%). Mp. 134-135° C.

¹H-NMR (400 MHz, DMSO-d₆): δ=10.6 (s, 1H), 8.69 (d, J=2.4 Hz, 1H), 8.47 (d, J=2.4 Hz, 1H), 8.16 (d, J=8.8 Hz, 1H), 8.03 (dd, J1=2.4, J2=8.8 Hz, 1H), 7.97 (d, J=8.8 Hz, 1H), 7.67 (brs, 2H), 7.30 (t, J=5.2 Hz, 1H), 6.5 (d, J=8.8 Hz, 1H), 3.27 (q, J=6.8 Hz, 2H), 2.74 (t, J=7.2 Hz, 2H), 1.54 (m, 4H), 0.91 (t, J=5.6 Hz, 6H).

MS (ESI): m/z=335 (M+Na)

BMS (215 µL) was added to a solution of 4 (180 mg, 0.575 mmol) in THF (10 ml). The reaction mixture was stirred at reflux temperature over night. The reaction mixture was cooled to RT. Then methanol (2 ml) was added slowly followed by conc. HCl (3 mL). The reaction mixture was refluxed for another 5 hrs. Then the reaction mixture was cooled, concentrated under reduced pressure, and diluted with cold water and the pH was adjusted to 14 with KOH pellets and extracted with chloroform (50 ml×3). The organic phase was washed with brine solution and dried over $Na_2SO_4$. The solvent was evaporated to give a crude product, which was purified on a silica gel column (EtOAc: PE, 80:20) to give the product (10 mg, 6.3%).

Mp. 129-130° C.

¹H NMR (400 MHz, DMSO-d₆): δ=8.14 (d, J=1.6 Hz, 1H), 8.0 (s, 1H), 6.42 (d, J=8.8 Hz, 1H), 6.32 (d, J=8.8 Hz, 1H), 5.0 (br s, 1H), 4.9 (br s, 1H), 4.33 (d, J=5.2 Hz, 2H), 3.25 (q, J=6.4 Hz, 4H), 1.66 (q, J=7.2 Hz, 4H), 1.01 (t, J=7.2 Hz 6H).

MS (ESI): m/z=321 (M+Na).

Preparation of 2ac: Preparation of N-benzyl-6-((5-(thiophen-2-yl)-1H-pyrazol-3-ylamino)methyl)pyridin-2-amine (5)

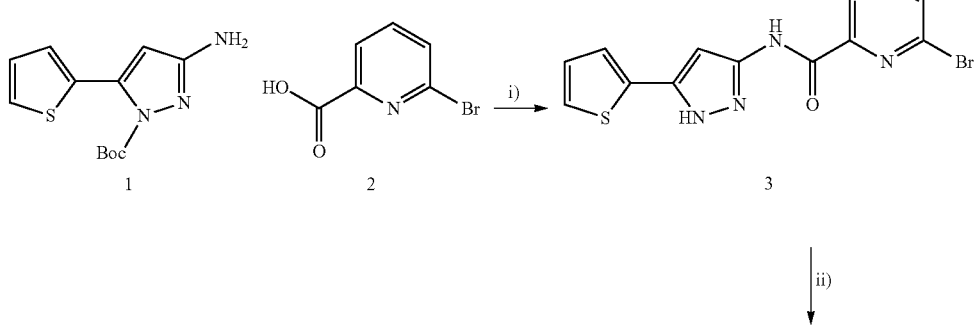

ii)

-continued

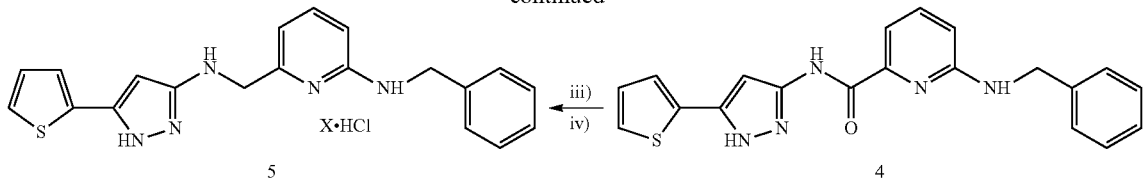

Reagents: i) 2-chloro-1-methylpyridinium iodide/DIPEA/RT/3 days ii) Benzylamine/120° C./ 16 h iii) BMS/THF/MeOH/HCl iv) HCl/MeOH 2-Chloro-1-methylpyridinium iodide (580 mL, 2.2 mmol) and DIPEA (0.4 mL) were added to a solution of 6-bromopicolinic acid 2 (304 mg, 1.5 mmol) in a mixture of dry DCM/DMF (20/2 mL). The reaction mixture was stirred for 1 hr before tert-butyl 3-amino-5-(thiophen-2-yl)-1H-pyrazole-1-carboxylate 1 (400 mg, 1.5 mmol) was added. The resulting yellow reaction mixture was stirred for 3 days. Then the reaction mixture was concentrated under reduced pressure. The residue was diluted in chloroform and washed with water and brine, and dried over $Na_2SO_4$. After evaporation of the solvent, the crude product was purified on a silica gel column (EtOAc: pet-ether, 1:1) to give 6-bromo-N-(5-(thiophen-2-yl)-1H-pyrazol-3-yl)picolinamide 3, (307 mg, 58%).

MS (ESI): m/z=349 (M+H) 350.8 (M+2H)

The 6-bromo-N-(5-(4-fluorophenyl)-1H-pyrazol-3-yl)picolinamide 3 (307 mg, 0.88 mmol) was dissolved in neat benzylamine (3 mL) without further characterization. The reaction mixture was heated at 130° C. for 24 hrs. Then the solvent was evaporated and the residue was purified on silica gel (EtOAc: pet-ether, 1:4) to give 6-(benzylamino)-N-(5-(thiophen-2-yl)-1H-pyrazol-3-yl)picolinamide 4 as a sticky solid (200 mg, 58%).

$^1$H-NMR (400 MHz, $CDCl_3$): δ=10.1 (s, 1H), 7.59 (m, 2H), 7.33 (m, 5H), 7.09 (s, 1H), 6.64 (d, J=8.0 Hz, 1H), 5.11 (brs, 1H), 4.60 (s, 2H).

MS (ESI): m/z=376 (M+H).

Borane dimethylsulfide (85 μL, 1.06 mmol) was added to a solution of 6-(benzylamino)-N-(5-(4-fluorophenyl)-1H-pyrazol-3-yl)picolinamide 4 (200 mg, 0.53 mmol). The reaction mixture was refluxed for 16 hrs. The reaction mixture was cooled to RT and MeOH (2 mL) followed by conc. HCl (2 mL) were added and the reaction mixture was refluxed for another 4 hrs. The reaction mixture was concentrated and diluted with water (4 ml) and the pH was adjusted to 14 using NaOH solution and subsequently the reaction mixture was extracted with chloroform (40 ml×3). All organic layers were then washed with water and brine, dried over $Na_2SO_4$. After evaporating the solvent, the crude product was recrystallized from EtOAc and pet-ether to give N-benzyl-6-((5-(4-fluorophenyl)-1H-pyrazol-3-ylamino)methyl)pyridin-2-amine, (80 mg, 41%). Mp. 117-118° C.

20 mg of the composition were then treated with HCl/MeOH to give 5, N-benzyl-6-((5-(4-fluorophenyl)-1H-pyrazol-3-ylamino)methyl)pyridin-2-amine hydrochloride salt. Mp. 120-122° C.

$^1$H-NMR (400 MHz, $CDCl_3$): δ=7.23-7.42 (m, 8H) 7.06 (d, J=1.6 Hz, 1H), 6.63 (d, J=6.8 Hz, 1H), 6.30 (d, J=8.0 Hz, 1H), 5.79 (s, 1H), 5.11 (brs, 1H), 4.74 (brs, 1H), 4.52 (brs, 2H), 4.30 (s, 2H).

MS (ESI): m/z=362 (M+H)

Preparation of 2ad: N-Propyl-5-((5-((4-p-tolylthiazol-2-ylamino)methyl)thiazol-2-ylamino)methyl)thiazol-2-amine trihydrochloride

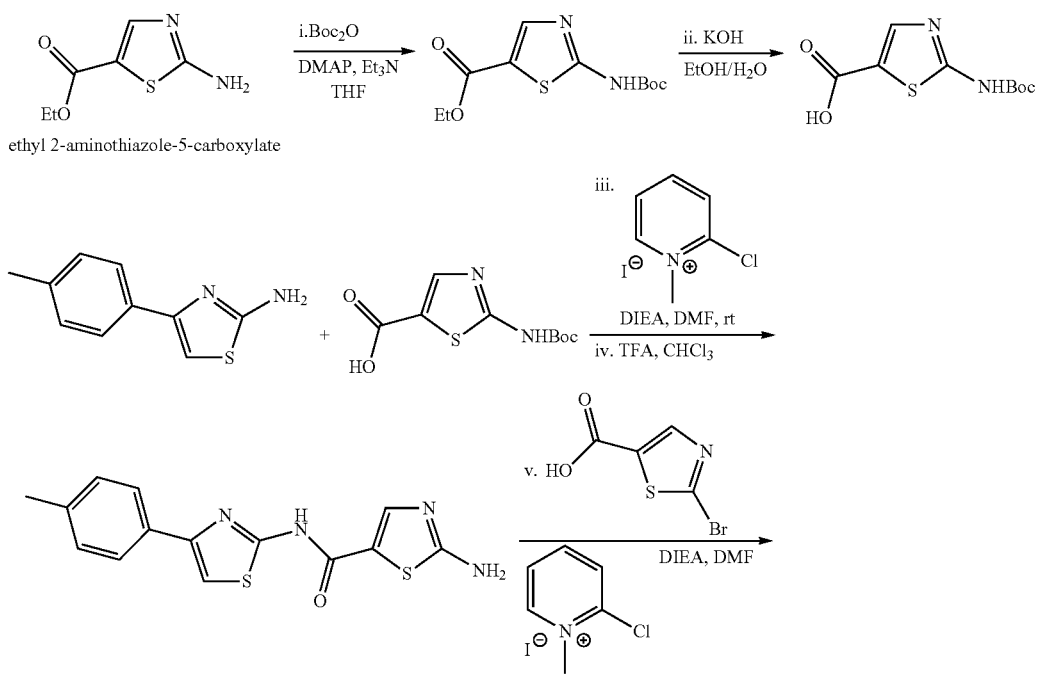

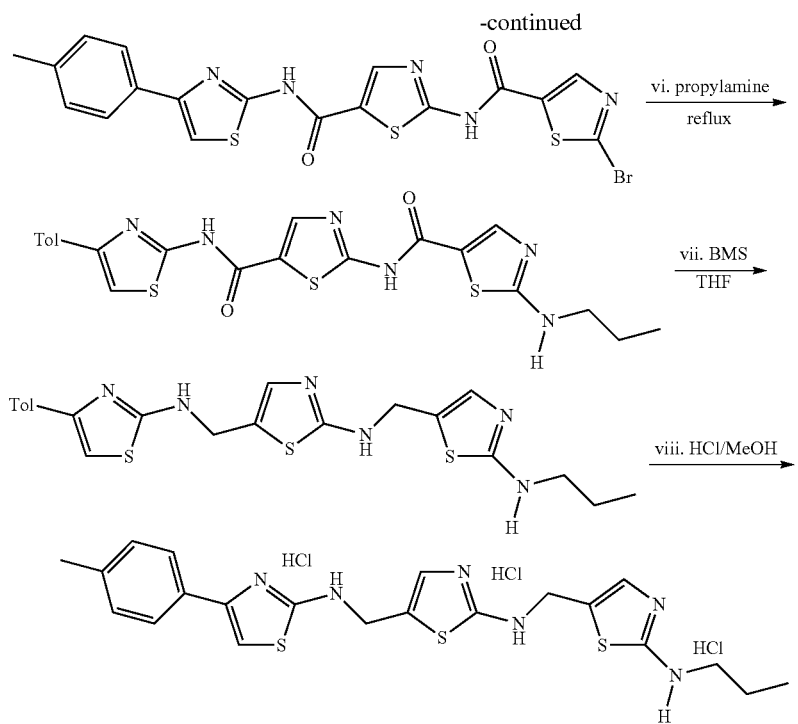

DMAP (35 mg, 0.29 mmol), Et₃N (16 mL, 116 mmol) and di-tert-butyl dicarbonate (13 mL, 58 mmol) were added to a solution of ethyl 2-aminothiazole-5-carboxylate (10 g, 58.1 mmol) in THF (100 mL). The resulting solution was stirred at RT until completion of the reaction. The solvents were evaporated and the crude product was purified by precipitation with PE, yielding ethyl 2-(tert-butoxycarbonylamino)thiazole-5-carboxylate (14.2 g, 90%) as a white solid.

$^1$H-NMR (400 MHz, CDCl$_3$): δ (ppm): 8.03 (s, 1H), 4.32 (q, J=7.2 Hz, 2H), 1.597 (s, 9H), 1.35 (t, J=6.8 Hz, 3H).

MS (ESI): m/z (%): 273.37 [MH⁺].

A solution of ethyl 2-(tert-butoxycarbonylamino)thiazole-5-carboxylate (5 g, 18.36 mmol) and KOH (10.3 g, 184 mmol) in EtOH/H$_2$O (1:1) (60 mL) was stirred at RT for 12 hrs. The solution was acidified with 1N HCl and the precipitate was filtered and dried, yielding 2-(tert-butoxycarbonylamino)thiazole-5-carboxylic acid (3.84 g, 86%) as a white solid.

$^1$H-NMR (400 MHz, DMSO-d$_6$): δ (ppm): 12.0 (bs, 1H), 7.94 (s, 1H), 1.5 (s, 9H).

MS (ESI): m/z (%): 245.35 [MH⁺].

2-Chloro-1-methylpyridinium iodide (0.47 g, 1.84 mmol), DIEA (0.44 mL, 2.5 mmol) and 4-p-tolylthiazol-2-amine (0.24 g, 1.23 mmol) were added to a solution of 2-(tert-butoxycarbonylamino)thiazole-5-carboxylic acid (0.30 g, 1.23 mmol) in DMF (5 mL). The resulting solution was stirred at RT until completion of the reaction. Then the reaction mixture was diluted with AcOEt, washed with water, dried with Na$_2$SO$_4$ and concentrated. The crude product was purified by column (100% AcOEt), yielding tert-butyl 5-(4-p-tolylthiazol-2-ylcarbamoyl)thiazol-2-ylcarbamate (80 mg, 17%) as a solid.

$^1$H-NMR (400 MHz, CDCl$_3$): δ (ppm): 10.8 (bs, 2H), 7.76 (s, 1H), 7.61 (d, J=8 Hz, 2H), 7.15 (d, J=8 Hz, 2H), 7.09 (s, 1H), 2.35 (s, 3H), 1.42 (s, 9H).

MS (ESI): m/z (%): 417.32 [MH⁺].

TFA (0.100 mL) was added to a solution of tert-butyl 5-(4-p-tolylthiazol-2-ylcarbamoyl)thiazol-2-ylcarbamate (80 mg, 0.19 mmol) in CHCl$_3$ (1 mL). The resulting solution was stirred at RT overnight. Then the solvents were evaporated and the crude product was dissolved in H$_2$O. After neutralization with NaHCO$_3$ saturated aqueous solution, it was extracted with AcOEt, dried and concentrated. Purification by column chromatography (100% AcOEt) yielded 2-amino-N-(4-p-tolylthiazol-2-yl)thiazole-5-carboxamide (40 mg, 67%) as a white solid.

$^1$H-NMR (400 MHz, CDCl$_3$/CD$_3$OD): δ (ppm): 7.67 (s, 1H), 7.47 (d, J=8 Hz, 2H), 6.97 (d, J=8 Hz, 2H), 6.87 (s, 1H), 2.13 (s, 3H).

$^{13}$C-NMR (100 MHz, CDCl$_3$/CD$_3$OD): δ (ppm): 173.92, 159.45, 158.36, 149.58, 143.45, 137.53, 131.35, 129.00, 125.59, 119.89, 106.58, 20.60.

MS (ESI): m/z (%): 317.33 [MH⁺].

2-Chloro-1-methylpyridinium iodide (0.048 g, 0.18 mmol), DIEA (0.045 mL, 0.25 mmol) and 2-amino-N-(4-p-tolylthiazol-2-yl)thiazole-5-carboxamide (0.04 g, 0.126 mmol) were added to a solution of 2-bromothiazole-5-carboxylic acid (26 mg, 0.126 mmol) in DMF (1 mL). The resulting solution was stirred at RT until completion of the reaction. Then a solid was precipitated with AcOEt and the solid was separated by centrifugation, yielding 2-bromo-N-(5-(4-p-tolylthiazol-2-ylcarbamoyl)thiazol-2-yl)thiazole-5-carboxamide (20 mg, 30%) as a solid that was used in the following step without further purification.

$^1$H-NMR (400 MHz, DMSO-d$_6$): δ (ppm): 8.65 (s, 1H), 7.95 (s, 1H), 7.82 (d, J=8 Hz, 2H), 7.61 (s, 1H), 7.25 (d, J=8 Hz, 2H), 2.33 (s, 3H).

A solution of 2-bromo-N-(5-(4-p-tolylthiazol-2-ylcarbamoyl)thiazol-2-yl)thiazole-5-carboxamide (15 mg, 0.03 mmol) in neat propylamine (0.5 mL) was stirred at reflux for 24 hrs. The solvent was evaporated and the crude product was purified by column chromatography (0%-5% MeOH/AcOEt) yielding 2-(propylamino)-N-(5-(4-p-tolylthiazol-2-ylcarbamoyl)-thiazol-2-yl)thiazole-5-carboxamide (15 mg, 17%).

$^1$H-NMR (400 MHz, CDCl$_3$/CD$_3$OD): δ (ppm): 8.12 (s, 1H), 7.86 (s, 1H), 7.56 (d, J=8 Hz, 2 H), 7.08 (d, J=8 Hz, 2H), 6.98 (s, 1H), 3.63 (bs, 1H), 3.13 (t, J=6.4 Hz, 2H), 2.23 (s, 3H), 1.55 (q, J=6.4 Hz, 2H), 0.86 (t, J=6.4 Hz, 3H)

MS (ESI): m/z (%): 485.33 [MH⁺]. .

BMS (0.015 mL, 0.15 mmol) was added to a solution of 2-(propylamino)-N-(5-(4-p-tolylthiazol-2-ylcarbamoyl)thiazol-2-yl)thiazole-5-carboxamide (15 mg, 0.03 mmol) in THF (1 mL) at RT. The resulting solution was stirred at RT overnight. The reaction was then quenched with MeOH (0.5 mL). 1N HCl was added until pH=2. After stirring the reaction mixture at RT for 12 hrs, the organic solvents were evaporated and the aqueous solution was neutralized with a NaHCO₃ saturated aqueous solution, extracted with AcOEt, dried with Na₂SO₄ and concentrated. The crude product was purified by column chromatography (0%-5% MeOH/AcOEt), yielding N-propyl-5-((5-((4-p-tolylthiazol-2-ylamino)methyl)thiazol-2-ylamino)methyl)thiazol-2-amine (5 mg, 32%).

¹H-NMR (400 MHz, CDCl₃/CD₃OD): δ (ppm): 7.68 (d, J=8 Hz, 2H), 7.17 (d, J=8 Hz, 2H), 7.05 (s, 1H), 6.96 (s, 1H), 6.66 (s, 1H), 4.52 (s, 2H), 4.42 (s, 2H), 3.41 (bs, 1H), 3.15 (t, J=6.4 Hz, 2H), 2.34 (s, 3H), 1.62 (m, 2H), 0.96 (t, J=6.4 Hz, 3H).

MS (ESI): m/z (%): 457.29 [MH⁺].

N-Propyl-5-((5-((4-p-tolylthiazol-2-ylamino)methyl)thiazol-2-ylamino)methyl)-thiazl-2-amine (5 mg, 0.01 mmol) was dissolved in methanolic HCl (3 N, 0.5 mL) and Et₂O was added. The precipitated solid was filtered by decantation and dried in vacuo, yielding N-propyl-5-((5-((4-p-tolylthiazol-2-ylamino)methyl)thiazol-2-ylamino)methyl)thiazol-2-amine trihydrochloride as a white solid (1.6 mg, 32%).

Mp.>135° C. decomposition.

Preparation of 2ae: 4-Benzyl-N-((2-(benzylamino)thiazol-5-yl)methyl)thiazol-2-amine dihydrochloride

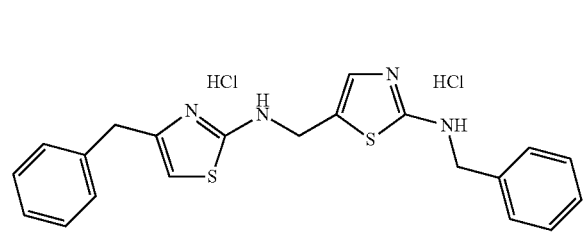 [SMILES: c1ccc(CNc2ncc(CNc3nc(Cc4ccccc4)cs3)s2)cc1 ; Cl ; Cl]

Compound 2ae was prepared as described for 2 h, starting from 4-benzylthiazol-2-amine and 2-bromothiazole-5-carboxylic acid: (10 mg, 29%). Mp. 78-79° C.

¹H-NMR (400 MHz, CDCl₃/CD₃OD): δ (ppm): 7.34-7.20 (m, 10H), 6.99 (s, 1H), 5.99 (s, 1H), 4.42 (s, 4H), 3.88 (s, 2H).

MS (ESI): m/z (%): 393.30 ([MH⁺], 100%).

Preparation of 2af: 4-Benzyl-N-((2-(methylamino)thiazol-5-yl)methyl)thiazol-2-amine dihydrochloride

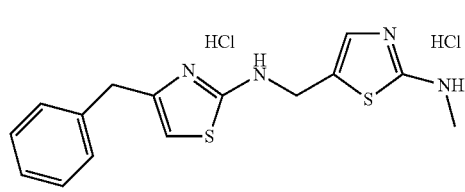 [SMILES: CNc1ncc(CNc2nc(Cc3ccccc3)cs2)s1 ; Cl ; Cl]

Compound 2af was prepared as described for 2w starting from 4-benzylthiazol-2-amine and 2-(methyl(tetrahydro-2H-pyran-2-yl)amino)thiazol-5-carbaldehyde: (50 mg, 46%). Mp. 126-127° C.

¹H-NMR (400 MHz, CDCl₃): δ (ppm): 7.19-7.13 (m, 5H), 6.85 (s, 1H), 5.87 (s, 1H), 4.28 (s, 2H), 3.81 (s, 2H), 3.76 (s, 2H), 2.78 (s, 2H).

MS (ESI): m/z (%): 317.30 ([MH⁺], 100%).

Preparation of 2ag: 5-Benzyl-N-((2-(benzylamino)thiazol-5-yl)methyl)thiazol-2-amine dihydrochloride

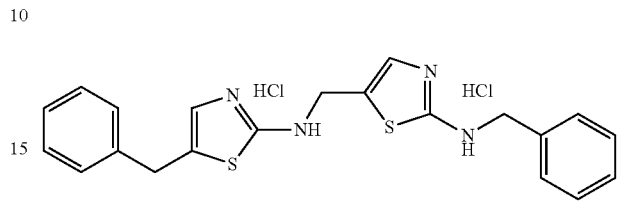

Compound 2ag was prepared as described for 2 h, starting from 5-benzylthiazol-2-amine and 2-bromothiazole-5-carboxylic acid: (25 mg, 69%). Mp. 96-97° C.

¹H-NMR (400 MHz, CDCl₃/CD₃OD): δ (ppm): 7.27-7.14 (m, 10H), 6.88 (s, 1H), 6.73 (s, 1H), 4.33 (s, 2H), 4.29 (s, 2H), 3.88 (s, 2H).

MS (ESI): m/z (%): 393.30 ([MH⁺], 100%).

Preparation of 2ah: 5-Benzyl-N-((2-(methylamino)thiazol-5-yl)methyl)thiazol-2-amine dihydrochloride

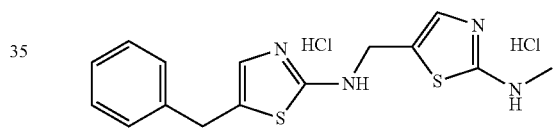

Compound 2ah was prepared as described for 2w starting from 5-benzylthiazol-2-amine and 2-(methyl-(tetrahydro-2H-pyran-2-yl)amino)thiazole-5-carbaldehyde (55 mg, 69%). Mp. 76-77° C.

¹H-NMR (400 MHz, CDCl₃): δ (ppm): 7.20-7.13 (m, 5H), 6.84 (s, 1H), 6.71 (s, 1H), 4.28 (s, 2 H), 3.85 (s, 4H), 2.78 (s, 3H).

¹³C-NMR (100 MHz, CDCl₃): δ (ppm): 171.79, 168.97, 139.47, 136.87, 134.74, 128.30, 128.08, 126.35, 125.83, 121.50, 41.65, 33.01, 31.38.

MS (ESI): m/z (%): 317.30 ([MH⁺], 100%).

Preparation of 2ai: 5-p-Tolyl-N-((5-((5-p-tolyl-1H-pyrazol-3-yl)methylamino)-1H-pyrazol-3-yl)methyl)-1H-pyrazol-3-amine trihydrochloride 1. Synthesis of 1-(tetrahydro-2H-pyran-2-yl)-5-p-tolyl-1H-pyrazol-3-amine 1-(tetrahydro-2H-pyran-2-yl)-5-p-tolyl-1H-pyrazol-3-amine was prepared as described for compound 2a.

1-(tetrahydro-2H-pyran-2-yl)-5-p-tolyl-1H-pyrazole-3-carboxylic acid was prepared as described previously for 2a.

2. Synthesis of 5-p-tolyl-N-((5-((5-p-tolyl-1H-pyrazol-3-yl)methylamino)-1H-pyrazol-3-yl)methyl)-1H-pyrazol-3-amine trihydrochloride
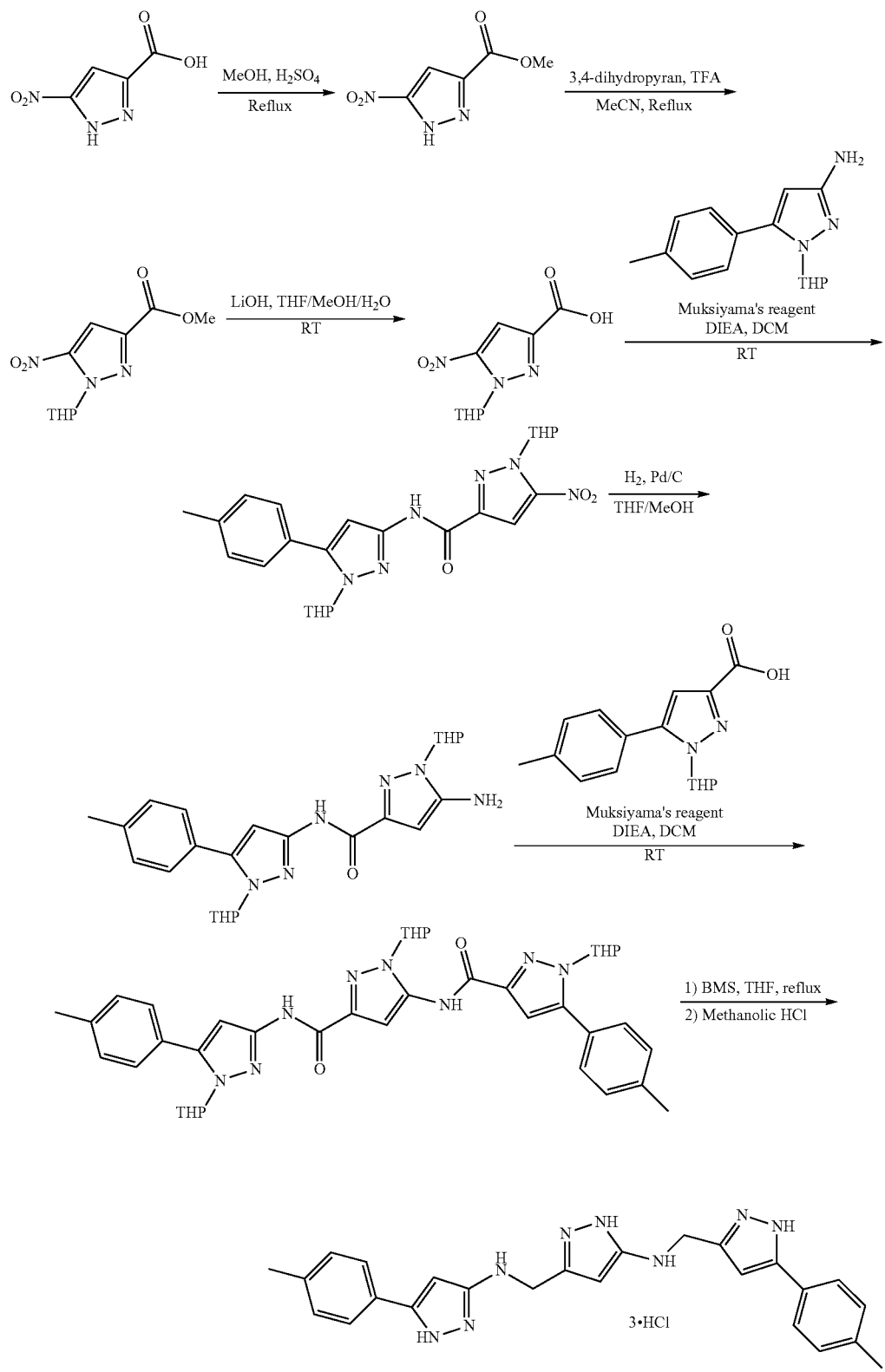

5-Nitro-3-pyrazole-carboxylic acid (8 g, 50.90 mmol) and sulfuric acid (5 mL, 1.48 mmol) in methanol (200 mL) were heated to reflux for 4 hrs. The solvent was evaporated and the residue was resuspended in $CH_2Cl_2$ and washed with water and brine and dried $Na_2SO_4$. Methyl 5-nitro-1H-pyrazole-3-carboxylate (7.5 g, 86%) was obtained as a white solid.

$^1$H-NMR (400 MHz, $CDCl_3$): δ (ppm)=7.40 (s, 1H), 4.00 (s, 3H).

A mixture of methyl 5-nitro-1H-pyrazole-3-carboxylate (7.5 g, 43.8 mmol), 3,4-dihydro-2H-pyran (8 mL, 87.7 mmol) and trifluoroacetic acid (65 μL, 0.9 mmol) in anhydrous MeCN (100 mL) was refluxed for 16 hrs. The solvent was evaporated and the residue was resuspended in $CH_2Cl_2$ (50 mL) and washed with $H_2O$ and brine. After drying with $Na_2SO_4$, solvent evaporation and silica gel column chromatography (PE-EtOAc, 9:1) methyl 1-(tetrahydro-2H-pyran-2-yl)-5-nitro-1H-pyrazole-3-carboxylate (3.71 mg, 33%) was obtained.

$^1$H-NMR (400 MHz, $CDCl_3$): δ (ppm)=7.41 (s, 1H), 6.35 (dd, J=9.2 Hz, J=2.4 Hz, 1H), 4.01 (d, J=9.6 Hz, 1H), 3.94 (s, 3H), 3.73 (t, J=8.0 Hz, 1H), 2.43 (m, 1H), 2.13 (m, 1H), 2.01 (m, 1H), 1.74-1.62 (m, 3H).

Methyl 1-(tetrahydro-2H-pyran-2-yl)-5-nitro-1H-pyrazole-3-carboxylate (500 mg, 0.70 mmol) was dissolved in a mixture of MeOH/THF/$H_2O$ (1:2:1, 20 mL). Lithium hydroxide (56.3 mg, 2.35 mmol) was added and the reaction mixture was stirred for 16 hrs. The reaction mixture was diluted with water and washed with DCM. The aqueous phase was evaporated which gave 1-(tetrahydro-2H-pyran-2-yl)-5-nitro-1H-pyrazole-3-carboxylic acid (300 mg, 64%) as a white solid which was used without further purification in the next step.

$^1$H-NMR (400 MHz, $CDCl_3$): δ (ppm)=7.22 (s, 1H), 6.61 (dd, J=9.2 Hz, J=2.4 Hz, 1H), 3.94 (d, J=11.2 Hz, 1H), 3.65 (t, J=10.4 Hz, 1H), 2.35 (m, 1H), 2.09 (m, 1H), 1.92 (m, 1H), 1.71-1.54 (m, 3H).

5-Tolyl-1-(tetrahydro-2H-pyran-2-yl)-1H-pyrazol-3-amine (97 mg, 0.38 mmol) was added to a solution of 1-(tetrahydro-2H-pyran-2-yl)-5-nitro-1H-pyrazole-3-carboxylic acid (100 mg, 0.41 mmol), 2-chloro-1-methylpyridinium iodide (145 mg, 0.56 mmol) and N,N'-diisopropylethylamine (193 L, 1.13 mmol) in DCM (10 mL). The reaction mixture was stirred at room temperature for 16 hrs. The reaction was diluted with water and extracted with DCM. The organic layer was washed with brine, dried with $Na_2SO_4$ and concentrated. The crude product was purified by silica gel column chromatography (PE-EtOAc, 8:2) and gave 5-nitro-1-(tetrahydro-2H-pyran-2-yl)-N-(1-(tetrahydro-2H-pyran-2-yl)-5-p-tolyl-1H-pyrazol-3-yl)-1H-pyrazole-3-carboxamide (60 mg, 33%).

$^1$H-NMR (400 MHz, $CDCl_3$): δ (ppm)=9.50 (s, 0.5H), 9.39 (s, 0.5H), 7.43 (d, J=6.4 Hz, 2H), 7.38 (s, 0.5H), 7.34 (s, 0.5H), 7.28 (d, J=8.0 Hz, 2H), 6.87 (s, 1H), 6.16 (dd, J=10.0 Hz, J=2.4 Hz, 1H), 6.14 (dd, J=10.0 Hz, J=2.0 Hz, 1H), 5.17 (d, J=10.4 Hz, 1H), 5.16 (dd, J=8.4 Hz, 1H), 3.80 (m, 2H), 3.60 (m, 2H), 2.42 (s, 3H), 2.13 (m, 2H), 1.78-1.56 (m, 8H).

Methanol (5 mL) and Pd/C were added to a solution of 5-nitro-1-(tetrahydro-2H-pyran-2-yl)-N-(1-(tetrahydro-2H-pyran-2-yl)-5-p-tolyl-1H-pyrazol-3-yl)-1H-pyrazole-3-carboxamide (183 mg, 0.38 mmol) in THF. The flask was then evacuated and filled with hydrogen. The reaction mixture was stirred for 16 hrs. The catalyst was filtered on celite and the solution was concentrated and dried to give 5-amino-1-(tetrahydro-2H-pyran-2-yl)-N-(1-(tetrahydro-2H-pyran-2-yl)-5-p-tolyl-1H-pyrazol-3-yl)-1H-pyrazole-3-carboxamide (170 mg, quantitative).

$^1$H-NMR (400 MHz, $CDCl_3$): δ (ppm)=8.94 (s, 0.5H), 8.83 (s, 0.5H), 7.43 (d, J=6.8 Hz, 2H), 7.28 (d, J=8.0 Hz, 2H), 6.95 (s, 1H), 6.41 (s, 1H, 1H), 6.06 (m, 2H), 5.17 (d, J=10.0 Hz, 2H), 3.73 (m, 2H), 3.59 (t, J=11.2 Hz, 2H), 2.42 (s, 3H), 2.05 (m, 2H), 1.80-1.54 (m, 8H).

MS (ESI): m/z: 451.32 [MH$^+$].

5-Amino-1-(tetrahydro-2H-pyran-2-yl)-N-(1-(tetrahydro-2H-pyran-2-yl)-5-p-tolyl-1H-pyrazol-3-yl)-1H-pyrazole-3-carboxamide (102 mg, 0.23 mmol) was added to a solution of 1-(tetrahydro-2H-pyran-2-yl)-5-p-tolyl-1H-pyrazole-3-carboxylic acid (59 mg, 0.20 mmol), 2-chloro-1-methylpyridinium iodide (79 mg, 0.31 mmol) and N,N'-diisopropylethylamine (105 μL, 0.62 mmol) in DCM (10 mL). The reaction mixture was stirred at room temperature for 16 hrs. The reaction mixture was diluted with water and extracted with DCM. The organic layer was washed with brine, dried with $Na_2SO_4$ and concentrated. The crude product was purified by silica gel column chromatography (PE-EtOAc, 7:3) and gave 1-(tetrahydro-2H-pyran-2-yl)-N-(1-(tetrahydro-2H-pyran-2-yl)-3-(1-(tetrahydro-2H-pyran-2-yl)-5-p-tolyl-1H-pyrazol-3-ylcarbamoyl)-1H-pyrazol-5-yl)-5-p-tolyl-1H-pyrazole-3-carboxamide (25 mg, 15%).

$^1$H-NMR (400 MHz, $CDCl_3$): δ (ppm)=9.42 (s, 1H), 9.40 (s, 1H), 7.43 (m, 4H), 7.37 (s, 0.5H, 0.5H), 7.28 (m, 4H), 6.93 (s, 1H), 6.88 (s, 1H), 5.20 (m, 3H), 4.14 (m, 3H), 3.77 (t, J=11.2 Hz, 1H), 3.62 (t, J=11.6 Hz, 1H), 3.59 (t, J=10.0 Hz, 1H), 2.43 (s, 6H), 2.06 (m, 3H), 1.74 (m, 3H), 1.54 (m, 6H), 1.24 (m, 6H).

MS (ESI): m/z: 719.39 [MH$^+$].

1-(Tetrahydro-2H-pyran-2-yl)-N-(1-(tetrahydro-2H-pyran-2-yl)-3-(1-(tetrahydro-2H-pyran-2-yl)-5-p-tolyl-1H-pyrazol-3-ylcarbamoyl)-1H-pyrazol-5-yl)-5-p-tolyl-1H-pyrazole-3-carboxamide (28 mg, 0.04 mmol) was suspended in anhydrous THF (500 μL) and borane dimethylsulfide complex (26 μL, 0.27 mmol) was added dropwise. The reaction mixture was stirred under reflux for 16 hrs. The reaction mixture was then cooled down to 0° C. and MeOH (50 μL) was added and the mixture was stirred for 10 min. Concentrated hydrochloric acid (12 N) was added until pH<2 was obtained The resulting mixture was stirred at 50° C. for 16 hrs. The mixture was cooled to room temperature and the solvent was evaporated. The residue was resuspended in THF and the precipitate was filtrated and washed with cold THF. 5-p-Tolyl-N-((5-((5-p-tolyl-1H-pyrazol-3-yl)methylamino)-1H-pyrazol-3-yl)methyl)-1H-pyrazol-3-amine was obtained as a white solid.

5-p-Tolyl-N-((5-((5-p-tolyl-1H-pyrazol-3-yl)methylamino)-1H-pyrazol-3-yl)methyl)-1H-pyrazol-3-amine (10 mg, 0.023 mmol) was recrystallized in methanolic HCl (3 N, 0.5 mL). The solid was filtered, washed with $Et_2O$ and dried in vacuo to give a white solid. Mp.=167° C.

$^1$H NMR (400 MHz, DMSO-$d_6$): δ=7.68 (d, J=8.0 Hz, 2H), 7.60 (d, J=8.0 Hz, 2H), 7.29 (d, J=8.0 Hz, 2H), 7.21 (d, J=8.0 Hz, 2H), 6.57 (s, 1H), 6.23 (s, 1H), 5.80 (s, 1H), 4.40 (s, 2H), 4.34 (s, 2H), 2.34 (s, 3H), 2.31 (s, 3H)

MS (ESI): m/z: 439.36 [MH$^+$]. .

Preparation of 2ak: N-Benzyl-5-((4-(4-chlorophenyl)thiazol-2-ylamino)methyl)thiazol-2-amine

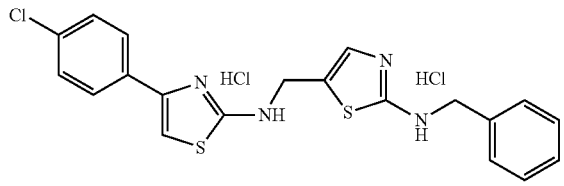 [SMILES: Clc1ccc(-c2csc(NCc3cnc(NCc4ccccc4)s3)n2)cc1 ; Cl ; Cl]

Compound 2ak was prepared as described for 2 h starting from 4-(4-chlorophenyl)thiazol-2-amine and 2-bromothiazole-5-carboxylic acid (31 mg, 49%). Mp. 105-106° C.

$^1$H-NMR (400 MHz, CDCl$_3$): ꟈ (ppm): 7.64 (d, J=8 Hz, 2H), 7.27-7.24 (m, 7H), 6.91 (s, 1 H), 6.63 (s, 1H), 4.42 (s, 2H), 4.33 (s, 1H), 4.21 (bs, 4H).

MS (ESI): m/z (%): 413.35 ([MH$^+$], 100%).

Preparation of 2al: N-Benzyl-5-((4-(thiophen-2-yl)thiazol-2-ylamino)methyl)thiazol-2-amine dihydrochloride

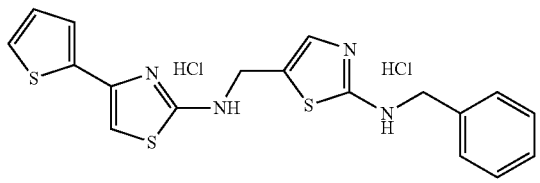 [SMILES: c1ccc(CNc2ncc(CNc3nc(-c4cccs4)cs3)s2)cc1 ; Cl ; Cl]

Compound 2al was prepared as described for 2 h, starting from 4-(thiophen-2-yl)thiazol-2-amine and 2-bromothiazole-5-carboxylic acid (6 mg, 50%); mp 97-99° C.

$^1$H-NMR (400 MHz, CDCl$_3$): δ (ppm): 7.29-7.25 (m, 6H), 7.17 (d, J=4.8 Hz, 1H), 6.98 (d, J=5.2 Hz, 2H), 6.56 (s, 1H), 4.42 (s, 2H), 4.36 (s, 2H).

MS (ESI): m/z (%): 385.38 ([MH$^+$], 100%).

Preparation of 2am: N-Butyl-6-((5-(4-fluorophenyl)-1H-pyrazol-3-ylamino)methyl)pyridin-2-amine

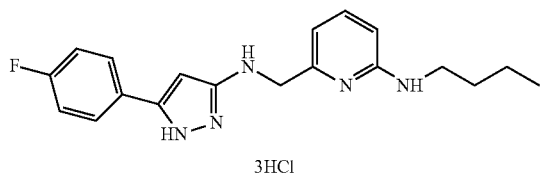 [SMILES: CCCCNc1cccc(CNc2cc(-c3ccc(F)cc3)[nH]n2)n1]

Compound 2am was synthesized as described for 2 s (59%). Mp. 93-94° C.

$^1$H-NMR (500 MHz, CDCl$_3$): δ=7.57 (dd, J=7.0 Hz, J=11 Hz 2H), 7.40 (t, J=10.5 Hz, 1H), 7.05 (t, 10.5 Hz, 2H), 6.58 (d, J=9.0 Hz, 1H), 6.58 (d, J=9.0, 1H), 6.26 (d, J=10.5 Hz, 1H), 5.81 (s, 1H), 4.72 (brs, 1H), 4.29 (s, 2H) 3.22 (m, 2H), 1.60 (m, 2H), 1.43 (m, 2H), 0.95 (t, J=9.5 Hz 3H).

MS (ESI): m/z=340 (M+H)

Example 1

The milogP and TPSA values of various compounds are indicated in table 1. milogP and TPSA values were calculated according to the software available on the world wide web (www.molinspiration.com), provided by P. Ertl of Novartis Pharma AG.

TABLE 1

| Compound | milogP | TPSA |
|---|---|---|
| 2a | 4.56 | 69.39 |
| 2c | 3.40 | 86.78 |
| 2h | 5.16 | 49.84 |
| 2j | 4.92 | 49.84 |
| 2k | 4.08 | 65.63 |
| 2n | 3.52 | 49.84 |
| 2o | 3.77 | 49.84 |
| 2p | 2.63 | 62.73 |
| 2q | 2.99 | 49.84 |
| 2s | 4.35 | 65.63 |
| 2t | 3.96 | 65.63 |
| 2u | 3.61 | 69.39 |
| 2w | 1.40 | 49.84 |
| 2y | 2.48 | 75.86 |
| 2z | 4.75 | 62.73 |
| 2aa | 3.75 | 49.84 |
| 2ab | 3.04 | 61.86 |
| 2ac | 3.58 | 65.63 |
| 2ad | 4.95 | 74.76 |
| 2ae | 4.99 | 49.84 |
| 2af | 3.60 | 49.84 |
| 2ag | 4.99 | 49.84 |
| 2ah | 3.60 | 49.84 |
| 2ai | 4.56 | 110.10 |
| 2aj | 4.44 | 61.87 |
| 2ak | 5.15 | 49.84 |
| 2al | 4.25 | 49.84 |
| 2am | 4.00 | 65.63 |

Example 2

A number of the small molecules were tested for their capacity to inhibit the aggregation of amyloid beta (Aβ) 1-42 peptide using a thioflavin T spectrofluorescence assay.

Preparation of (Aβ) Peptide Film

Aβ1-42 lyophilized powder (Bachem) was reconstituted in hexafluoroisopropanol (HFIP) to 1 mM. The peptide solution was sonicated for 15 min at room temperature, agitated overnight, and aliquots were placed into non-siliconized microcentrifuge tubes. The HFIP was then evaporated under a stream of argon. The resulting peptide film was dried under vacuum for 10 min, tightly sealed and stored at −80° C. until used.

Inhibition of Aβ1-42 Aggregation

To assay for the small molecule-mediated inhibition of Aβ1-42 aggregation, the small molecules were dissolved before each experiment in anhydrous dimethyl sulfoxide (DMSO, Sigma-Aldrich) to reach a concentration of 7.4 mM. Aβ1-42 peptide film was dissolved in DMSO to reach 400 µM. Assay solution in PBS buffer was prepared in non-siliconized incubation tubes to reach the following concentrations: 330 µM small molecule, 33 µM Aβ1-42, 10 µM thioflavin T (ThT), and 12.8% DMSO. Therefore, the final molar ratio of small molecule to Aβ1-42 was 10:1. A positive control without a small molecule was prepared to measure maximum RFU. A negative control without Aβ1-42 was prepared for each small molecule. 3-Aminopyrazole trimer (Trimer) was tested in all assays to ascertain reproducibility between independent experiments. The solutions were incubated for 24 hrs at 37° C., and the spectrofluorescence (relative fluorescence units; RFU) was read in six replicates in black 384-well assay plates (Perkin-Elmer) on a Perkin-Elmer Fluoro-Count spectrofluorometer. Inhibition of aggregation is expressed as mean % inhibition or ±1 standard deviation (SD) according to the following equation:

$$\% \text{ inhibition} = \frac{(RFU \text{ of positive control} - RFU \text{ of negative control}) - (RFU \text{ of sample with } A\beta1\text{-}42 - RFU \text{ of sample without } A\beta1\text{-}42)}{(RFU \text{ of positive control} - RFU \text{ of negative control})} \times 100$$

Cut-off criterium for the selection of functional molecules was defined at 50% inhibition capacity.

Results

The small molecules were tested for their capacity to inhibit aggregation of Aβ1-42 in the ThT assay. The results for the molecules are summarized in the following table. All the small molecules synthesized inhibited the aggregation of Aβ1-42 in the ThT assay to some extent and a number of the molecules tested demonstrated an inhibition capacity over 50%.

TABLE

Inhibition of Aβ1-42 aggregation and disaggregation of preformed Aβ1-42 fibers by small molecules

| Compound | % inhibition |
|---|---|
| 2a* | 65.3 ± 2.6 |
| 2c | 77.0 ± 5.3 |
| 2h | 31.9 ± 10.1 |
| 2j | 70.7 ± 6.8 |
| 2k | 81.2 ± 7.3 |
| 2n | 27.8 ± 9.9 |
| 2o | 39.6 ± 2.8 |
| 2p | 43.6 ± 2.1 |
| 2q | 45.0 ± 8.3 |
| 2s* | 55.1 ± 6.4 |
| 2t | 86.8 ± 2.9 |
| 2u | 55.3 ± 1.0 |
| 2w | 13.9 ± 12.9 |
| 2y | 57.0 ± 15.9 |
| 2z | 58.7 ± 3.0 |
| 2aa | 41.5 ± 9.6 |
| 2ab | 1.7 ± 11 |
| 2ac | 78.5 ± 1.3 |
| 2ad | 82.1 ± 2.2 |
| 2ae | 51.2 ± 1.5 |
| 2af | 41.3 ± 9.2 |
| 2ag | 34.2 ± 1.6 |
| 2ah | 35.7 ± 5.6 |
| 2ai | 84.8 ± 0.0 |
| 2ak | 37.2 ± 14.8 |
| 2al | 66.1 ± 15.4 |
| 2am | 68..2 ± 9.7 |

*Fluorescent compound in absence of Amyloid β1-42

The small molecules were evaluated for their capacity to mediate inhibition of Aβ1-42 aggregation at a 10:1 small molecule to Aβ1-42 molar ratio. The results are expressed as mean±standard deviation of two independent experiments.

Example 3

FCS-Assay with 5 nM Oregon Green Labelled Aβ-Peptide

In order to analyse for the disaggregating properties of the compounds, preformed aggregates were used, which were induced straight before the FCS-measurement by diluting 500 nM DMSO-stock solutions of Oregon Green labelled Aβ1-42 1:1 with deionized water. The final concentration of Oregon Green labelled Aβ-peptide was 5 nM in 1×PBS and 3% DMSO. In order to improve the reproducibility of the measurements of the concentration dependencies of all samples were prepared fourfold.

TABLE

FCS-Measurements: percentage of the "number of peaks" value obtained for the control reaction without added compound.

| Compound | 200 nM | 100 nM |
|---|---|---|
| 2t | 67.2 | nd |
| 2c | 51.2 | 29.4 | nd: not done

TABLE

FCS-Measurements: percentage of the "peaks x height" value obtained for the control reaction without added compound.

| Compound | 200 nM | 100 nM |
|---|---|---|
| 2t | 53.3 | nd |
| 2c | 45.1 | 26.6 | nd: not done

Example 4

Effect of a Compound of the Invention on Cultured Retinal Ganglion Cell (RGC) Apoptosis To assess the in vitro capacity of a compound of the invention to reduce retinal ganglion cell (RGC) death related to ocular diseases associated with pathological abnormalities/changes in the tissues of the visual system, particularly associated with amyloid-beta-related pathological abnormalities/changes in the tissues of the visual system, such as, for example, neuronal degradation, cultured RGCs from rats and mice are used.

To isolate the cells, at sacrifice the animals are anesthesized, their eyes are removed and the retina is dissected and incubated in 2 mg/ml papain solution for 25 minutes at 37° C. to break down the extracellular matrix. At the end of treatment, the cells are washed three times with RCG medium in the presence of a protease inhibitor to stop the papain action. The tissue is then triturated by passing it quickly up and down through a Pasteur pipette until the cells are dispersed. A commercially available Coulter counter is used to determine cell density in the cell suspension, before culturing the cells in 95% air/5% $CO_2$ at 37° C.

In order to mimic the damage from ocular diseases associated with pathological abnormalities/changes in the tissues of the visual system, particularly associated with amyloid-beta-related pathological abnormalities/changes in the tissues of the visual system, such as, for example, neuronal degradation, and assess the preventive effect of a compound of the invention, the cells are incubated with L-glutamate for three days in the presence or absence of a compound of the invention. Cells cultured in buffer alone serve as control.

To determine RGC survival, at the end of the incubation period the cells are fixed with 3.7% formaldehyde in phosphate buffered saline (PBS) at room temperature for 30 minutes, rinsed three times in PBS and incubated for 1 hour in PBS containing RGC specific markers Thy1.1 or NF-L antibody. The antibody is then removed by washing and the cells are incubated for 30 minutes with fluorescence-labeled secondary antibodies goat anti-mouse IgG, goat anti-rabbit IgG or rabbit anti-goat IgG. At the end of the incubation, the cells are washed, stained for 5 minutes with DAPI solution and rinsed. Surviving RGCs are counted by fluorescence microscopy.

Example 5

Effect of a Compound of the Invention on Retinal Ganglion Cell (RGC) Apoptosis In Vivo To assess the in vivo capacity of a compound of the invention to reduce retinal ganglion cell (RGC) death in individuals affected by ocular diseases associated with pathological abnormalities/changes in the tissues of the visual system, particularly associated with amyloid-beta-related pathological abnormalities/changes in the tissues of the visual system, such as, for example, neuronal degradation, rats and mice are used for a 2 to a 16 week long induced intra-ocular pressure (IOP) study. Retinal ganglion cell death is measured at the end of the study by both in vivo imaging and histological endpoint analysis.

In order to mimic the increase in intra-ocular pressure associated with certain ocular diseases associated with pathological abnormalities/changes in the tissues of the visual system, particularly associated with amyloid-beta-related pathological abnormalities/changes in the tissues of the visual system, such as, for example, neuronal degradation, glaucoma in particular, the animals are first anesthetized with intraperitoneal ketamine (75 mg/kg) and xylazine (5 mg/kg) and topical proparacaine 1% eye drops. Two alternative methods are then used to artificially elevate IOP in one eye (unilaterally) in rats and mice. In the first method, the anesthetized animals receive laser-induced injury to the trabecular meshwork by treating the aqueous outflow area with a 532-nm diode laser at the slit lamp perpendicular to the trabeculae and parallel to the iris. The animals receive an initial treatment of 40 to 50 spots of 50-μm size, 0.4 W, and 0.6 second duration.

In the second method to artificially increase IOP, the anesthetized animals receive a 501 injection of hypertonic saline solution into the episcleral veins in one eye using a microneedle with a force just sufficient to blanch the vein.

To measure IOP, a commercially available handheld tonomer (Tonopen XL-VET) is used. The measurements are taken while the animals are under anesthesia as the average of 10 readings immediately before laser treatment, 1 day after, and then weekly for the duration of the experiment. If, at an interval of one week, the difference in the IOP between the two eyes of the animals is less than 6 mm Hg, the animals are not further included in the study.

In order to evaluate the preventive effect of a compound of the invention on RGC apoptosis, half of the animals receiving the IOP-inducing treatment receive an intravitreal or intravenous injection of a compound of the invention at the time of IOP elevation. Half of the animals serve as control. The number of RGCs is measured by both in vivo imaging and histological endpoint analysis at 2, 4, 8 and 16 weeks after induced elevation of IOP. Analysis of RGCs undergoing apoptosis in vivo is performed by the DARC method. The DARC method consists in administering intravitreally fluorophore-conjugated Annexin 5, which specifically binds to apoptotic cells, to the animals and visualizing the RCGs undergoing apoptosis in vivo. If necessary, this method may be used in conjunction with backlabelling of the optic nerve from the SCN to identify live RCGs which no longer possess an intact axon and have lost connectivity with their targets.

In addition, in order to measure the total number of RCGs, endpoint histological analysis of the retina and optic nerve is performed at sacrifice. The retinas of the animals are fixed in 4% paraformaldehyde and stained in sections or whole mount using the RGC specific markers, such as Thy1.1, NF-L and SMI 32, as well as antibodies specific for cells undergoing apoptosis. In each of these methods, the total number of RGCs is measured at 2, 4, and 8, and 16 weeks after surgical elevation of IOP.

To measure the number of RGC axons remaining in the optic nerve after IOP elevation, the optic nerves of the animals are dissected and the nerves are fixed in 4% paraformaldehyde, sectioned, and stained with toluidine blue for analysis.

We claim:

1. A compound having the general formula (IIa)

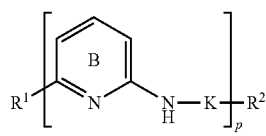

wherein
p is 2 or 3;
each linker K is independently $C_{1-3}$ alkylene which is optionally substituted by one or more $C_{1-4}$ alkyl groups;
the heterocyclic ring B is optionally substituted by one or more substituents selected from $C_{1-4}$ alkyl, $C_{1-4}$ alkoxy, mono- and di-$C_{1-4}$ alkyl amino, $C_{3-7}$ cycloalkyl amino, and 5- or 6-membered saturated heterocyclyl, or two substituents may be joined to form a saturated, unsaturated or aromatic 5- to 7-membered ring which is fused with the heterocyclic ring B;
$R^1$ is selected from —H, -halogen, —$C_{1-4}$ alkyl, —$NH_2$, —NH—$C_{1-4}$ alkyl, —$C_{1-4}$ alkylene-$NH_2$, —$C_{1-4}$ alkylene-NH—$C_{1-4}$ alkyl, -aryl, -aryl-$R^3$, —$C_{1-4}$ alkylene-aryl, —$C_{1-4}$ alkylene-aryl-$R^3$, -heteroaryl, -heteroaryl-$R^3$, —NH—$C_{1-4}$ alkylene-aryl, —NH—$C_{1-4}$ alkylene-aryl-$R^3$, —OH and —O—$C_{1-4}$ alkyl; and
$R^3$ is $C_{1-4}$ alkyl, halogen, OH or O—$C_{1-4}$ alkyl;

$R^2$ is —H, —$C_{1-4}$ alkyl, -aryl or a group of the formula (IIIa)

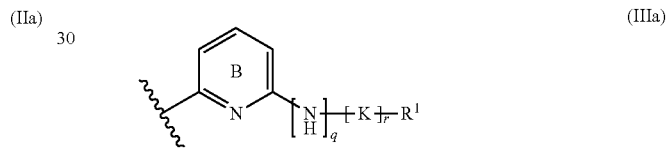

wherein B, K and $R^1$ are as defined above, q is 0 or 1 and r is 0 or 1.

2. The compound according to claim 1, wherein each linker K is independently —$CH_2$—, —$CH_2CH_2$— or —$CH_2CH_2CH_2$—.

3. The compound according to claim 1, wherein $R^1$ is —H, —$CH_3$, —NH—$C_{1-4}$ alkyl or —$CH_2$—NH—$CH_3$.

4. The compound according to claim 1, wherein $R^2$ is a group of the formula (IIa).

5. A composition comprising a compound as defined in claim 1.

6. A composition comprising the compound as defined in claim 1 and at least one further biologically active compound optionally in combination with a pharmaceutically acceptable carrier, a diluent, or an excipient.

7. A test kit for detection and/or diagnosis of an amyloid-associated disease or condition comprising the compound according to claim 1.

* * * * *

SEQUENCE LISTING

```
<160> NUMBER OF SEQ ID NOS: 4

<210> SEQ ID NO 1
<211> LENGTH: 112
<212> TYPE: PRT
<213> ORGANISM: Artificial Sequence
<220> FEATURE:
<223> OTHER INFORMATION: Artificial Humanized C2 HuVK 1 Variable Light
      Chain

<400> SEQUENCE: 1

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Ser Gln Ser
                    85                  90                  95

Thr His Val Pro Trp Thr Phe Gly Gln Gly Thr Lys Val Glu Ile Lys
                100                 105                 110

<210> SEQ ID NO 2
<211> LENGTH: 219
<212> TYPE: PRT
<213> ORGANISM: Artificial Sequence
<220> FEATURE:
<223> OTHER INFORMATION: Artificial Humanized C2 Light Chain

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 3
<211> LENGTH: 112
<212> TYPE: PRT
<213> ORGANISM: Artificial Sequence
<220> FEATURE:
<223> OTHER INFORMATION: Artificial Humanized C2 HuVH AF 4 Variable
      Heavy Chain

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45
```

```
Ala Ser Ile Asn Ser Asn Gly Gly Ser Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
               100                 105                 110

<210> SEQ ID NO 4
<211> LENGTH: 439
<212> TYPE: PRT
<213> ORGANISM: Artificial Sequence
<220> FEATURE:
<223> OTHER INFORMATION: Artificial Humanized C2 Heavy Chain

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Gly Met Ser Trp Val Arg Gln Ala Pro Gly Lys Gly Leu Glu Leu Val
            35                  40                  45

Ala Ser Ile Asn Ser Asn Gly Gly Ser Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
               100                 105                 110

Ala Ser Thr Lys Gly Pro Ser Val Phe Pro Leu Ala Pro Cys Ser Arg
               115                 120                 125

Ser Thr Ser Glu Ser Thr Ala Ala Leu Gly Cys Leu Val Lys Asp Tyr
           130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
               165                 170                 175

Leu Ser Ser Val Val Thr Val Pro Ser Ser Ser Leu Gly Thr Lys Thr
           180                 185                 190

Tyr Thr Cys Asn Val Asp His Lys Pro Ser Asn Thr Lys Val Asp Lys
       195                 200                 205

Arg Val Glu Ser Lys Tyr Gly Pro Pro Cys Pro Pro Cys Pro Ala Pro
   210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
               245                 250                 255

Asp Val Ser Gln Glu Asp Pro Glu Val Gln Phe Asn Trp Tyr Val Asp
           260                 265                 270

Gly Val Glu Val His Asn Ala Lys Thr Lys Pro Arg Glu Glu Gln Phe
       275                 280                 285

Asn Ser Thr Tyr Arg Val Val Ser Val Leu Thr Val Leu His Gln Asp
   290                 295                 300

Trp Leu Asn Gly Lys Glu Tyr Lys Cys Lys Val Ser Asn Lys Gly Leu
```

-continued

```
305             310             315             320
Pro Ser Ser Ile Glu Lys Thr Ile Ser Lys Ala Lys Gly Gln Pro Arg
                325             330             335
Glu Pro Gln Val Tyr Thr Leu Pro Pro Ser Gln Glu Glu Met Thr Lys
                340             345             350
Asn Gln Val Ser Leu Thr Cys Leu Val Lys Gly Phe Tyr Pro Ser Asp
        355             360             365
Ile Ala Val Glu Trp Glu Ser Asn Gly Gln Pro Glu Asn Asn Tyr Lys
        370             375             380
Thr Thr Pro Pro Val Leu Asp Ser Asp Gly Ser Phe Phe Leu Tyr Ser
385             390             395             400
Arg Leu Thr Val Asp Lys Ser Arg Trp Gln Glu Gly Asn Val Phe Ser
                405             410             415
Cys Ser Val Met His Glu Ala Leu His Asn His Tyr Thr Gln Lys Ser
                420             425             430
Leu Ser Leu Ser Leu Gly Lys
                435
```